(12) United States Patent
Kim et al.

(10) Patent No.: US 7,601,736 B2
(45) Date of Patent: Oct. 13, 2009

(54) PYRIDINE DERIVATIVES, A PROCESS FOR THEIR PREPARATION AND A PHARMACEUTICAL COMPOSITION CONTAINING THE SAME

(75) Inventors: Hyung Ook Kim, Suwon-si (KR); Nam Kyu Lee, Suwon-si (KR); Joo Hyon Kim, Seongnam-si (KR); Hae In Rhee, Seoul (KR); Yong-Baik Cho, Anyang-si (KR); Je Ho Ryu, Seoul (KR); Nam Ho Kim, Seongnam-si (KR); Keun Ho Ryu, Seoul (KR); Jung Bum Yi, Suwon-si (KR); Jae Yoon Jung, Namyangju-si (KR)

(73) Assignee: SK Chemicals Co., Ltd., Kyungki-Do (KR)

( * ) Notice: Subject to any disclaimer, the term of this patent is extended or adjusted under 35 U.S.C. 154(b) by 116 days.

(21) Appl. No.: 10/585,029

(22) PCT Filed: Dec. 30, 2004

(86) PCT No.: PCT/KR2004/003545

§ 371 (c)(1),
(2), (4) Date: Apr. 16, 2007

(87) PCT Pub. No.: WO2005/063768

PCT Pub. Date: Jul. 14, 2005

(65) Prior Publication Data

US 2007/0254909 A1 Nov. 1, 2007

(30) Foreign Application Priority Data

Dec. 30, 2003 (KR) .................. 10-2003-0100132

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)

(52) U.S. Cl. .............. 514/300; 514/302; 546/116; 546/122

(58) Field of Classification Search .......... 546/115, 546/122, 116; 514/300, 302
See application file for complete search history.

(56) References Cited

OTHER PUBLICATIONS

Van Allan et al., Journal of Heterocyclic Chemistry (1970), 7(3), 495-507.*
Elmaati et al., Journal of the Chinese Chemical Society (Taipei, Taiwan) (2002), 49(6), 1045-1050.*
Eugster et al., Helvetica Chimica Acta (1957), 40, 69-79.*
Govindachari et al., Journal of the Chemical Society (1957) 551-6.*
Birkofer et al., Chemische Berichte (1957), 90, 2933-40.*
Trommer et al., Tetrahedron Letters (1973), (17), 1447-8.*
Rygg M et al., Scandinavian journal of immunology, (Jun. 2001), vol. 53, No. 6, pp. 588-595.*
Kametani, Tetsuji et al. Studies on the Syntheses of Heterocyclic Compounds, 657.[1a]"Total Synthesis of Angustine, Nauclefine, and Gentianine [1b], J. Org. Chem., vol. 41, No. 15, 1976, pp. 2542-2545.
Oehlke, J. et al.: 'Darstellung einiger 4- und 5-substituierter Pyridin-2-carbonsauren als Fusarsaureanaloga', Pharmazie, 38 (1983) pp. 591-596.
Dondoni, Alessandro et al.: Model Studies toward the Synthesis of Dihydropyrimidinyl and Pyridyl α-Amino Acids via Three-Component Biginelli and Hantzsch Cyclocondensations, J. Org. Chem., 2003, 68, pp. 6172-6183.
El-Sedawy, Adel I. et al.: "Metabolism of Swertiamarin from *Swertia japonica* by Human Intestinal Bacteria", Planta Medica 55 (1989), pp. 147-150.
Tada, Masaru et al.: 'Modification of Pyridine-3-carboxamide (Nicotinamide) by Radical Substitution', J. Heterocyclic Chem., 26, 45 (1989), pp. 45-48.
Popov, S.S. et al.: "In Vitro Transformations of Gentiopicroside and Swertiamarin", Journal of Natural Products, vol. 51, No. 4, Jul.-Aug. 1988, pp. 765-768.
Itoh, Atsuko et al.: "Biogenetic Conversion of Tetrahydroisoquinoline-Monoterpene Glucosides into Benzopyridoquinolizine Alkaloids of *Alangium lamarckii*", J. Nat. Prod., 1996, 59, pp. 535-538.
Jahangir et al.: "A New Route to the Indolopyridonaphthyridine Ring System: Synthesis of N-Benzyl-13b, 14-Dihydronauclefine and N-Benzyl-13b, 14-Dihydroangustine", Tetrahedron, vol. 43, No. 24, 1987, pp. 5761-5768.

* cited by examiner

*Primary Examiner*—D. Margaret Seaman
*Assistant Examiner*—Niloofar Rahmani
(74) *Attorney, Agent, or Firm*—Frommer Lawrence & Haug LLP; Ronald R. Santucci

(57) ABSTRACT

The invention relates to novel pyridine derivatives having an inhibitory effect on production of cytokines, which are involved in inflammatory responses, thus suggesting its usefulness as therapeutic agents for treating diseases related to inflammation, immune, chronic inflammation as well as an agent having an anti-inflammatory and analgesic effect. Further, this invention relates to a method of manufacturing the same and a pharmaceutical composition containing the same.

13 Claims, No Drawings

PYRIDINE DERIVATIVES, A PROCESS FOR THEIR PREPARATION AND A PHARMACEUTICAL COMPOSITION CONTAINING THE SAME

This application is a 371 of PCT/KR2004/003545 filed on Dec. 30, 2004, published on Jul. 14, 2005 under publication number WO 2005/063768 A1 which claims priority benefits from Korean Patent Application No. 10-2003-0100132 filed Dec. 30, 2003.

TECHNICAL FIELD OF THE INVENTION

This invention relates to novel pyridine derivatives having an inhibitory effect on production of cytokines, which are known to be involved in inflammatory responses, thus being useful as therapeutic agents for treating diseases related to inflammation, immune, chronic inflammation as well as an agent having an anti-inflammatory and analgesic effect. Further, this invention relates to a method of manufacturing the same and a pharmaceutical composition containing the same.

BACKGROUND OF THE INVENTION

An inflammatory response, a defensive mechanism of the body, consists of a highly sophisticated biological signal transduction triggered upon immonological perception of inflammations or injuries and is mediated by various inflammatory cytokines. In general, a disease that disrupts normal tissues as a result of abnormality in such an inflammatory response is called 'an inflammatory disease' and extensive researches have been performed worldwide to elucidate the details of its mechanism. Further, the increase of inflammatory cytokines is related to various autoimmune diseases.

Inflammation-related signal transduction system is a series of phosphorylation-dephosphorylation chain reaction and is largely divided into three stages: 1) the initial stage of binging of an inflammation signal in a biomembrane with a biomembrane receptor thereby triggering a series of signal transduction chain reaction; 2)the terminal stage of controlling expression of a gene encoding an inflammation-related protein by means of transcription factors within a nucleus; and 3) an intermediate stage which consists of a series of signal transduction chain reactions that link between the intial stage and the terminal stage.

Examples of well-known inflammation signal factor at the initial stage are tumor necrosis factor (TNF; also referred to as TNF-α) and interleukin-1 (IL-1). Examples of well-known inflammation signal factor at the terminal stage are activating protein-1 (AP-1; activating protein-1), nuclear transcription factor kappa B (NFkB) and nuclear factor of activated T cells (NFAT). The chain reactions at the intermediate stage are not well identified but it appears that lipocortin, cyclooxygenase-1, 2, and PLA$_2$ are involved in this stage.

Referring to inflammation-causing factors, TNF-α, produced mainly in activated macrophage and T cells, is the most powerful inflammatory cytokine and stimulates the production of other inflammatory cytokines such as IL-1, IL-6 and IL-8 as well as transcription factors such as NK-kB and c-jun/Ap-1. In fact, TNF-α is related with the development of inflammatory diseases or immune-related diseases such as toxic shock syndrome, insulin-dependent diabetes, multiple sclerosis, rheumatic arthritis, osteoarthritis, Crohn's disease and ulcerative colitis. In particular, TNF-α is also related with chronic inflammatory diseases such as psoriatic arthritis, psoriatis, ankylosing spondylitis, adult-onset Still's disease, polymyositis, dermatomyositis, and vasculitis such as Behcet disease and Wegener's granulomatosis Behcet disease and Wegener's granulomatosis. IL-1 is also a powerful inflammatory cytokine comparable to TNF-α and increases the expression of genes of PLA$_2$ 2 type, COX-2 and iNOS, and as a result, elevates the production of PAF, PGE$_2$ and NO, thereby inducing inflammatory responses. IL-1α and IL-1β are both related with auto-immune diseases such as rheumatic arthritis and insulin-dependent diabetes. IL-1β, like the TNF-α, is also an important mediator of septic shock and cardioopulmonary failure, acute respiratory syndrome and multiple organ failure. IL-6 is a multi-functional cytokine produced in various cells, and is related with diseases such as multiple myeloma, psoriatis, post-menopausal osteoporosis, CNS trauma, viral and bacterial meningitis, Castleman's disease, glomerulonephritis, AIDS dementia complex, a particular neuronal disease such as Altzheimer's disease, a particular leukemia, and systemic erythematosus lupus. IFN-γ is primarily produced by T cells and NK cells and is related with Graft-versus-Host disease, asthma, and other inflammatory diseases such as atopic disease. Further, IL-8 is related with diseases such as stroke, cardiac infarction, acute respiratory distress syndrome, post-injury multiple organ, acute glomerulonephritis, dermatitis, purulent meningitis, or other CNS failure, parahemodialysis, and necrotizing enterocolitis.

In addition, prostaglandins are known to play an important role in an inflammatory response. Inhibition of production of prostaglandins, especially PGG$_2$, PGH$_2$ and PGE$_2$, plays a key role in developing an anti-inflammatory agent. For example, production of prostaglandins can be inhibited by inhibiting the cyclooxygenase (COX), which is induced by inflammatory cytokines. Therefore, the production of prostaglandins can be inhibited by inhibiting cytokines.

Accordingly, as stated above, the decrease in cytokines can be a good method to treat inflammatory diseases as well as immune-related diseases.

Recently, the inventors of the present invention succeeded in synthesizing pyridine derivatives with a novel structure and also discovered that these novel derivatives inhibit the production of cytokines involved in inflammatory responses, in particular, they have a superior inhibitory effect on the production of TNF-α, IL-1, IL-6, IFN-γ and PGE$_2$, Consequently, the inventors of the present invention found that the novel compounds synthesized by the present inventors have superior therapeutic effects on diseases such as inflammatory diseases, immune-related diseases, and chronic inflammatory diseases as well as being useful as an agent having an anti-inflammatory and analgesic effect thereby completing the present invention.

Accordingly, in a preferred embodiment, this invention provides novel pyridine derivatives.

In another preferred embodiment, this invention provides a method to prepare the above-mentioned pyridine derivatives.

In another still preferred embodiment, this invention provides a pharmaceutical composition for treating diseases related with cytokines such as inflammatory diseases, immune-related diseases, chronic inflammatory diseases which is also useful as an anti-inflammatory and analgesic agent.

DETAILED DESCRIPTION OF THE INVENTION

This invention relates to pyridine derivatives of the following formula 1 and their pharmaceutically acceptable salts thereof,

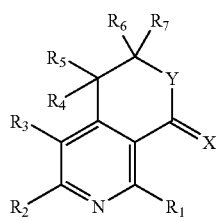

(1)

wherein $R_1$, $R_2$, $R_3$, $R_4$, $R_5$, $R_6$ and $R_7$ are independently selected from the group consisting of a hydrogen atom, a halo, a cyano, a nitro, an acyl, a hydroxy, an amino, a $C_1$-$C_6$ low alkyl, a $C_2$-$C_6$ low alkenyl, a $C_1$-$C_6$ low alkoxy, a $C_1$-$C_6$ alkylthio, a $C_1$-$C_{10}$ alkylamino, a $C_4$-$C_9$ cycloalkylamino, a $C_4$-$C_9$ heterocycloalkylamino, a $C_1$-$C_{10}$ aralkylamino, an arylamino, an acylamino, a saturated heterocyclic, an acyloxy, a $C_1$-$C_6$ alkylsulfinyl, a $C_1$-$C_6$ alkylsulfonyl, a $C_1$-$C_6$ alkylsulfonylamino, an arylsulfinyl, an arylsulfonyl, an arylsulfonylamino, an aryl, a heteroaryl, a $C_1$-$C_{10}$ aralkyl, a $C_1$-$C_{10}$ heteroaralkyl, an aryloxy and a heteroaryloxy group; or $R_1$, $R_2$, $R_3$, $R_4$, $R_5$, $R_6$ and $R_7$ independently form a ring by binding with a neighboring substitution group;

X is an oxygen or sulfur atom;

Y is an oxygen atom or N—$R_8$, wherein $R_8$ is selected from the group consisting of a hydrogen atom, a $C_1$-$C_6$ low alkyl, an acyl, an aryl, a heteroaryl, a $C_1$-$C_{10}$ aralkyl and a $C_1$-$C_{10}$ heteroaralkyl group; or forms a ring by binding with a neighboring substitution group of $R_6$ or $R_7$;

the above aryl group is selected from a phenyl, a naphthyl and a fused phenyl group;

the above heteroaryl and saturated heterocyclic groups are a heterocyclic ring with a pentagonal or hexagonal shape having 1 to 3 heteroatoms selected from an oxygen, a nitrogen, and a sulfur atom; or a fused heterocyclic ring; and the above aryl and heteroaryl groups are such that 1 to 4 substitution groups selected from the group consisting of a halo, a hydroxy, a $C_1$-$C_6$ low alkyl, a $C_1$-$C_6$ low alkoxy, an amino, a cyano, a nitro, a carbonyl and a carboxyl group are substituted.

The pyridine compounds of the above formula 1 can form their pharmaceutically acceptable salts by reacting with an acid such as hydrochloric acid, bromic acid, sulfuric acid, phosphoric acid, methane sulfonic acid, acetic acid, citric acid, fumaric acid, lactic acid, maleic acid, succinic acid, and tartaric acid.

Further, the pyridine compounds of the above formula 1 can form their pharmaceutically acceptable salts by reacting with an alkali metal ion such as sodium and potassium, or an ammonium ion. Therefore, the novel compounds prepared according to the present invention also include the pharmaceutically acceptable salts of the pyridine compounds of the above formula 1.

In a preferred embodiment of the present invention, the pyridine compounds of the above formula 1 are as follows:

that is, in the above formula 1, $R_1$, $R_2$ and $R_3$ are independently selected from the group consisting of a hydrogen atom, a halo, a hydroxy, a $C_1$-$C_6$ low alkyl, a $C_2$-$C_6$ low alkenyl, a $C_1$-$C_6$ low alkoxy, an aryloxy, an amino, a $C_1$-$C_6$ alkylamino, a $C_1$-$C_{10}$ aralkylamino, an arylamino, an acylamino, a saturated heterocyclic, an aryl, a heteroaryl, and a $C_1$-$C_{10}$ heteroaralkyl group; or neighboring $R_2$ and $R_3$ form a ring by binding with each other;

$R_4$, $R_5$, $R_6$ and $R_7$ are independently selected from the group consisting of a hydrogen atom, a $C_1$-$C_6$ low alkyl and an aryl group; or $R_4$, $R_5$, $R_6$ and $R_7$ independently form a ring by binding with a neighboring substitution group;

X is an oxygen or sulfur atom;

Y is an oxygen atom or N—$R_8$, wherein $R_8$ is selected from the group consisting of a hydrogen atom, a $C_1$-$C_6$ low alkyl, an aryl, and a $C_1$-$C_{10}$ aralkyl group;

the aryl group is a phenyl group;

the heteroaryl and saturated heterocyclic groups are selected from furan, thiophene, pyridine, piperidine, piperazine, morpholine, pyrolidine and benzodioxol; and the aryl and heteroaryl groups are such that 1 to 4 substitution groups selected from the group consisting of a halo, a hydroxy, a $C_1$-$C_6$ low alkyl, a $C_1$-$C_6$ low alkoxy, an amino, a cyano, a nitro, a carbonyl and a carboxyl group are substituted.

More specifically, the pyridine compounds of the above formula 1 can be further delineated as follows. That is, the pyridine compounds of the above formula 1 are:

3,4-dihydro-pyrano[3,4-c]pyridine-1-on,
6-methyl-3,4-dihydro-pyrano[3,4-c]pyridine-1-on,
5-vinyl-3,4-dihydro-pyrano[3,4-c]pyridine-1-on,
6,8-dichloro-3,4-dihydro-pyrano[3,4-c]pyridine-1-on,
6,8-dihydroxy-3,4-dihydro-pyrano[3,4-c]pyridine-1-on,
8-hydroxy-6-methyl-3,4-dihydro-pyrano[3,4-c]pyridine-1-on,
8-chloro-6-methyl-3,4-dihydro-pyrano[3,4-c]pyridine-1-on,
6-methyl-1-oxo-3,4-dihydro-1H-pyrano[3,4-c]pyridine-8-yl acetic ester,
8-methoxy-6-methyl-3,4-dihydro-pyrano[3,4-c]pyridine-1-on,
6,8-dimethyl-3,4-dihydro-pyrano[3,4-c]pyridine-1-on,
6-methyl-8-furan-2-yl-3,4dihydro-pyrano[3,4-c]pyridine-1-on,
6-methyl-8-thiophene-2-yl-3,4-dihydro-pyrano[3,4-c]pyridine-1-on,
6-methyl-8-pyridine-2-yl-3,4-dihydro-pyrano[3,4-c]pyridine-1-on,
8-(4-fluoro-phenyl)-6-methyl-3,4-dihydro-pyrano[3,4-c]pyridine-1-on,
8-(4-chloro-phenyl)-6-methyl-3,4-dihydro-pyrano[3,4-c]pyridine-1-on,
6-methyl-8-piperidine-1-yl-3,4-dihydro-pyrano[3,4-c]pyridine-1-on,
6-methyl-8-morpholine4-yl-3,4-dihydro-pyrano[3,4-c]pyridine-1-on,
6-methyl-8-(4-methyl-piperazine-1-yl)-3,4-dihydro-pyrano[3,4-c]pyridine-1-on,
6-methyl-8-(4-pyrimidine-2-yl-piperazine-1-yl)-3,4-dihydro-pyrano[3,4-c]pyridine-1-on,
8-(4-fluoro-phenylamino)-6-methyl-3,4-dihydro-pyrano[3,4-c]pyridine-1-on,
8-(4-chloro-phenylamino)-6-methyl-3,4-dihydro-pyrano[3,4-c]pyridine-1-on,
8-(4-trifluoromethyl-phenylamino)-6-methyl-3,4-dihydro-pyrano[3,4-c]pyridine-1-on,
6-methyl-8-p-tolylamino-3,4-dihydro-pyrano[3,4-c]pyridine-1-on,
6-methyl-8-phenylamino-3,4-dihydro-pyrano[3,4-c]pyridine-1-on,
6-methyl-8-phenetylamino-3,4-dihydro-pyrano[3,4-c]pyridine-1-on,
8-[(benzo[1,3]dioxol-5-ylmethyl)-amino]-6-methyl-3,4-dihydro-pyrano[3,4-c]pyridine-1-on,
6-methyl-8-phenyl-3,4-dihydro-pyrano[3,4-c]pyridine-1-on, 6-methyl-8-phenoxy-3,4-dihydro-pyrano[3,4-c]pyridine-1-on,
8-benzylamino-6-methyl-3,4-dihydro-pyrano[3,4-c]pyridine-1-on,
8-(4-methoxy-benzylamino)-6-methyll-3,4-dihydro-pyrano[3,4-c]pyridine-1-on,
8-amino-6-methyl-3,4-dihydro-pyrano[3,4-c]pyridine-1-on,
8-acetamido-6-methyl-3,4-dihydro-pyrano[3,4-c]pyridine-1-on,
8-benzamido-6-methyl-3,4-dihydro-pyrano[3,4-c]pyridine-1-on,
8-hydroxy-6-methyl-5-phenyl-3,4-dihydro-pyrano[3,4-c]pyridine-1-on,
8-chloro-6-methyl-5-phenyl-3,4-dihydro-pyrano[3,4-c]pyridine-1-on,
6-methyl-5-phenyl-3,4-dihydro-pyrano[3,4-c]pyridine-1-on,
6-phenyl-3,4-dihydro-pyrano[3,4-c]pyridine-1-on,
8-hydroxy-6-phenyl-3,4-dihydro-pyrano[3,4-c]pyridine-1-on,
8-chloro-6-phenyl-3,4-dihydro-pyrano[3,4-c]pyridine-1-on,
8-methyl-6-phenyl-3,4-dihydro-pyrano[3,4-c]pyridine-1-on,
1-oxo-6-phenyl-3,4-dihydro-1H-pyrano[3,4-c]pyridine-8-yl acetic ester,
8-methoxy-6-phenyl-3,4-dihydro-pyrano[3,4-c]pyridine-1-on,
8-methylamino-6-phenyl-3,4-dihydro-pyrano[3,4-c]pyridine-1-on,
8-dimethylamino-6-phenyl-3,4-dihydro-pyrano[3,4-c]pyridine-1-on,
6-phenyl-8-piperidine-1-yl-3,4-dihydro-pyrano[3,4-c]pyridine-1-on,
8-morpholine-4-yl-6-phenyl-3,4-dihydro-pyrano[3,4-c]pyridine-1-on,
6-phenyl-8-pyrolidine-1-yl-3,4-dihydro-pyrano[3,4-c]pyridine-1-on,
8-(4-fluoro-phenylamino)-6-phenyl-3,4-dihydro-pyrano[3,4-c]pyridine-1-on,
8-(4-methoxy-benzylamino)-6-phenyl-3,4-dihydro-pyrano[3,4-c]pyridine-1-on,
8-amino-6-phenyl-3,4-dihydro-pyrano[3,4-c]pyridine-1-on,
8-acetamido-6-phenyl-3,4-dihydro-pyrano[3,4-c]pyridine-1-on,
8-benzamido-6-phenyl-3,4-dihydro-pyrano[3,4-c]pyridine-1-on,
6hydroxy-8-methyl-3,4-dihydro-pyrano[3,4-c]pyridine-1-on,
6-chloro-8-methyl-3,4-dihydro-pyrano[3,4-c]pyridine-1-on,
8-methyl-6-(thiophene-2-yl)-3,4-dihydro-pyrano[3,4-c]pyridine-1-on,
6-(furan-2-yl)-8-methyl-3,4-dihydro-pyrano[3,4-c]pyridine-1-on,
6-(benzo[d][1,3]dioxol-6-yl)-8-methyl-3,4-dihydro-pyrano[3,4-c]pyridine-1-on,
6-(4-(dimethylamino)phenyl)-8-methyl-3,4-dihydro-pyrano[3,4-c]pyridine-1-on,
8-hydroxy-6-propyl-3,4-dihydro-pyrano[3,4-c]pyridine-1-on,
8-chloro-6-propyl-3,4-dihydro-pyrano[3,4-c]pyridine-1-on,
8-propyl-6-chloro-3,4-dihydro-pyrano[3,4-c]pyridine-1-on,
8-morpholine-4-yl-6-propyl-3,4-dihydro-pyrano[3,4-c]pyridine-1-on,
1-oxo-6-propyl-3,4-dihydro-1H-pyrano[3,4-c]pyridine-8-yl acetic ester
8-(4-methoxy-benzylamino)-6-propyl-3,4-dihydro-pyrano[3,4-c]pyridine-1-on,
8-amino-6-propyl-3,4-dihydro-pyrano[3,4-c]pyridine-1-on,
N-(1-oxo-6-propyl-3,4-dihydro-1H-pyrano[3,4-c]pyridine8-yl)-acetamide,
3,4-dihydro-2-oxa-aza-phenanthrene-1-on,
3,4-dihydro-pyrano[3,4-c]pyridine-1-thione,
2-(4-methoxy-benzyl)-3,4-dihydro-2H-[2,7]naphthyridine-1-on,
3,4-dihydro-2H-[2,7]naphthyridine-1-on,
2-benzyl-3,4-dihydro-2H-[2,7]naphthyridine-1-on,
3-phenyl-3,4-dihydro-pyrano[3,4-c]pyridine-1-on,
3-phenyl-3,4-dihydro-2H-[2,7]naphthyridine-1-on,
8-methyl-6-phenyl-3,4-dihydro-2H-[2,7]naphthyridine-1-on,
2,8-dimethyl-6-phenyl-3,4-dihydro-2H-[2,7]naphthyridine-1-on,
2-benzyl-8-methyl-6-phenyl-3,4-dihydro-2H-[2,7]naphthyridine-1-on,
6-cyclohexyl-8-hydroxy-3,4-dihydro-pyrano[3,4-c]pyridine-1-on,
6-cyclohexyl-1-oxo-3,4-dihydro-1H-pyrano[3,4-c]pyridine-8-yl acetic acid methyl ester,
8-chloro-6cyclohexyl-3,4-dihydro-pyrano[3,4-c]pyridine-1-on,
6-cyclohexyl-8-piperidine-1-yl-3,4-dihydro-pyrano[3,4-c]pyridine-1-on,
6-cyclohexyl-8-(4-mthoxy-benzylamino)-3,4-dihydro-pyrano[3,4-c]pyridine-1-on,
8-amino-6-cyclohexyl-3,4-dihydro-pyrano[3,4-c]pyridine-1-on,
8-hydroxy-6-isopropyl-3,4-dihydro-pyrano[3,4-c]pyridine-1-on,
6-isopropyl-1-oxo-3,4-dihydro-1H-pyrano[3,4-c]pyridine-8-yl acetic acid methyl ester,
8-chloro-6-isopropyl-3,4-dihydro-pyrano[3,4-c]pyridine-1-on,
6-isopropyl-8-(4-methoxy-benzylamino)-3,4-dihydro-pyrano[3,4-c]pyridine-1-on; and
their pharmaceutically acceptable salts.

In another preferred embodiment, the present invention provides a method for preparing pyridine derivatives of the above formula 1.

Of the pyridine derivatives of the present invention, those of the above formula 1, wherein X and Y are individually an oxygen atom, can be prepared by 3 different methods according to the following reaction schemes 1, 2 and 3.

The reaction scheme 1 briefly shows the first method of preparing the pyridine derivatives of the above formula 1, wherein X and Y are individually an oxygen atom, according to the present invention.

[Scheme 1]

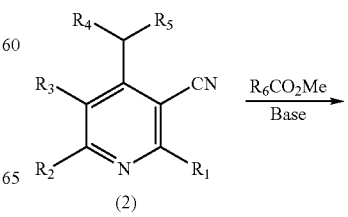

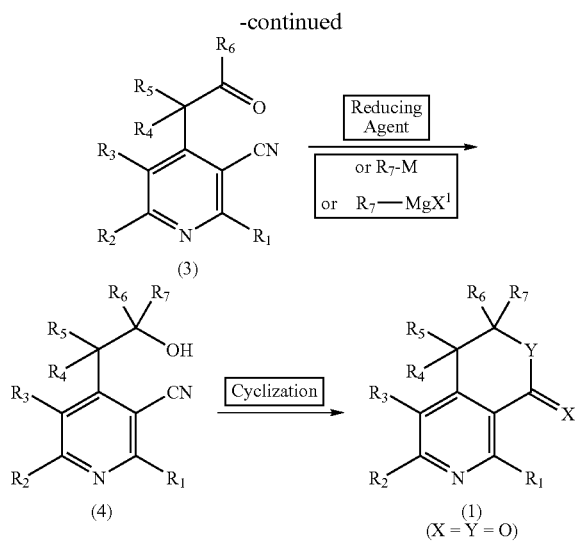

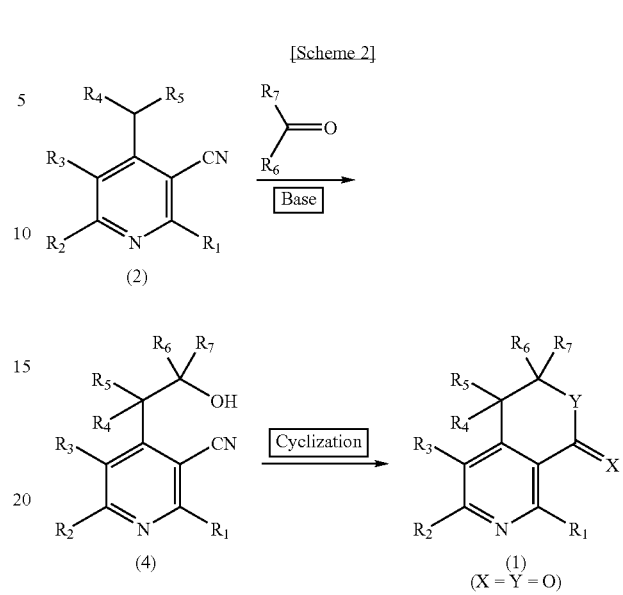

In the above reaction scheme 1, $R_1$, $R_2$, $R_3$, $R_4$, $R_5$, $R_6$, $R_7$, X and Y are the same as defined in the above, and M is an alkali metal atom and, $X^1$ is a halogen atom, The compound of the above formula 2, which is used as a starting material in the above method, can be easily prepared by the known method (*J. Org. Chem.*, Vol. 41, No. 15, 2542, 1976; *Pharmazie*, 38(9), 591, 1983)).

According to the method shown in the above reaction scheme 1, the compound of the above formula 2 was first dissolved in an anhydrous inert aprotic solvent, stirred at about −100° C. to about −40° C. after dropwisely adding a base, added again dropwisely with an alkyl ester, preferably methylester ($R_6COOMe$), and reacted for about 2 to about 8 hrs at about −78° C. to room temperature and the compound of the above formula 3 was obtained.

In the above reaction, the aprotic solvent to be used includes tetrahydrofuran (THF), diethylether, dioxane, and preferably THF. Examples of the base to be used include lithium bis(trimethylsilyl)amide (LHMDS), potassium bis(trimethylsilyl)amide (KHMDS), lithium diisopropylamide (LDA), sodium hydride (NaH), potassium hydride (KH) and lithium hydride (LiH), and preferably LHMDS.

Then, the compound of the above formula 3 was added with a reducing agent or a metal reagent containing $R_7$ and reacted at about 0° C. to room temperature while stirring for about 6 to about 12 hrs and the alcohol compound of the above formula 4 was obtained.

Examples of a reducing agent to be used include sodium borohydride ($NaBH_4$) or lithium borohydride ($LiBH_4$).

Examples of a metal reagent containing $R_7$ to be used include an alkali reagent represented by $R_7M$ or Grignard's reagent represented by $R_7MgX^1$, wherein $R_7$ is the same as defined above, M represents an alkali metal such as lithium, potassium and sodium, $X^1$ represents a halogen atom.

Then, the alcohol compound of the above formula 4 was cyclized by refluxing for about 6 to about 12 hrs in the presence of a conc. HCl and the compound of the above formula 1, wherein X and Y are individually an oxygen atom, was finally obtained.

The following reaction scheme 2 briefly shows the second method to prepare the compound of the above formula 1, wherein X and Y are individually an oxygen atom.

In the above reaction scheme 2, $R_1$, $R_2$, $R_3$, $R_4$, $R_5$, $R_6$, $R_7$, X and Y are the same as defined in the above.

According to the method shown in the above reaction scheme 2, the compound of the above formula 2 was first reacted with an alkyl carbonyl compound represented by $R_6COR_7$ ($R_6$ and $R_7$ are the same as defined in the above) along with a base in the presence of an anhydrous inert aprotic solvent and the compound of the above formula 4 was obtained.

In the above reaction, examples of the aprotic solvent include tetrahydrofuran (THF), diethyl ether and dioxane, and preferably THF.

Examples of the base to be used include lithium bis(trimethylsilyl)amide (LHMDS), potassium bis(trimethylsilyl)amide (KHMDS), lithium diisopropylamide (LDA), sodium hydride (NaH), potassium hydride (KH) and lithium hydride (LiH), and preferably LHMDS.

Then, the alcohol compound of the above formula 4 was cyclized the same as in the above reaction scheme 1 and the compound of the above formula 1, wherein X and Y are individually an oxygen atom, was finally obtained.

The following reaction scheme 3 briefly shows the third method to prepare the compound of the above formula 1, wherein X and Y are individually an oxygen atom.

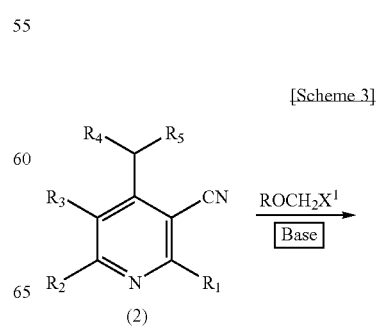

-continued

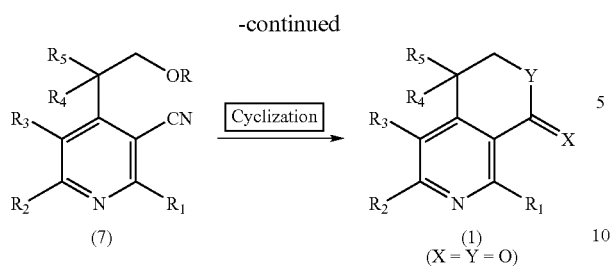

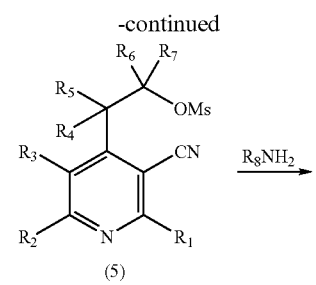

In the above reaction scheme 3, $R_1$, $R_2$, $R_3$, $R_4$, $R_5$, X and Y are the same as defined in the above and $X^1$ is a halogen atom.

According to the method shown in the above reaction scheme 3, the compound of the above formula 2 was first reacted with an alkoxy methyl compound represented by $ROCH_2X^1$ (R is a $C_1$-$C_6$ low alkyl, aryl or aralyl group, preferably a methyl, ethyl or benzyl group, $X^1$ is a halogen atom) along with a base in the presence of an anhydrous inert aprotic solvent and the compound of the above formula 7 was obtained.

In the above reaction, examples of the aprotic solvent include tetrahydrofuran (THF), diethyl ether and dioxane, and preferably THF.

Examples of the base to be used include lithium bis(trimethylsilyl)amide (LHMDS), potassium bis(trimethylsilyl)amide (KHMDS), lithium diisopropylamide (LDA), sodium hydride (NaH), potassium hydride (KH) and lithium hydride (LiH), and preferably LHMDS.

Then, the compound of the above formula 7 was cyclized the same as in the above reaction scheme 1 and the compound of the above formula 1, wherein X and Y are individually an oxygen atom, was finally obtained.

The following reaction scheme 3 briefly shows the third method to prepare the compound of the above formula 1, wherein $R_6$ and $R_7$ are individually a hydrogen atom and X and Y are individually an oxygen atom.

Of the pyridine derivatives of the present invention, those of the above formula 1, wherein X is an oxygen atom and Y is N—$R_8$, can be prepared by 4 different methods according to the following reaction schemes 4, 5, 6 and 7.

The reaction scheme 4 briefly shows the first method of preparing the pyridine derivatives of the above formula 1, wherein X is an oxygen atom and Y is N—$R_8$, according to the present invention.

[Scheme 4]

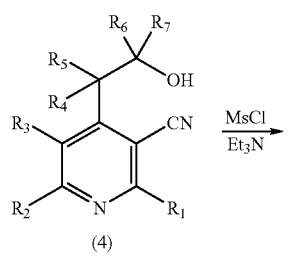

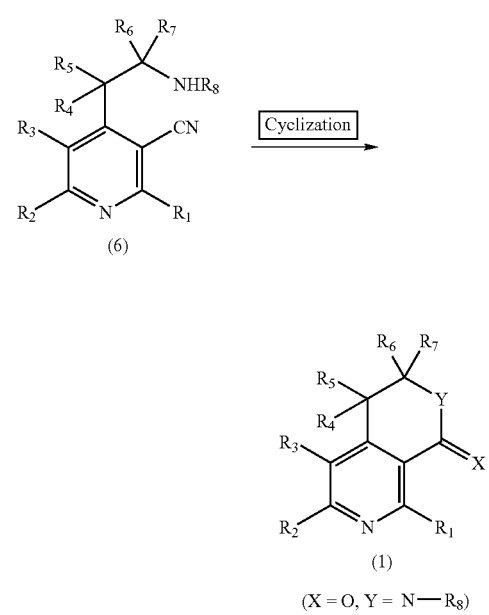

In the above reaction scheme 4, $R_1$, $R_2$, $R_3$, $R_4$, $R_5$, $R_6$, $R_7$, $R_8$, X and Y are the same as defined in the above.

According to the method shown in the above reaction scheme 4, the compound of the above formula 4 was first reacted with methansulfonylchloride (MsCl) or p-toluenesulfonylchloride along with a base such as pyridine or triethylamine ($Et_3N$) in the presence of an organic solvent and the compound of the above formula 5 was obtained.

In the above reaction, the preferred examples of the organic solvent are methylene chloride ($CH_2Cl_2$) or chloroform ($CHCl_3$).

Then, the compound of the above formula 5 was reacted with an amine compound represented by $R_8NH_2$, wherein $R_8$ is the same as defined above, to obtain the compound of the above formula 6, which was then cyclized under an acidic condition, for example in an alcoholic solution containing hydrochloric acid or sulfuric acid, and the compound of the above formula 1, wherein X is an oxygen atom and Y is N—$R_8$, was finally obtained.

The following reaction scheme 5 briefly shows the second method to prepare the compound of the above formula 1, wherein X is an oxygen atom and Y is N—$R_8$.

[Scheme 5]

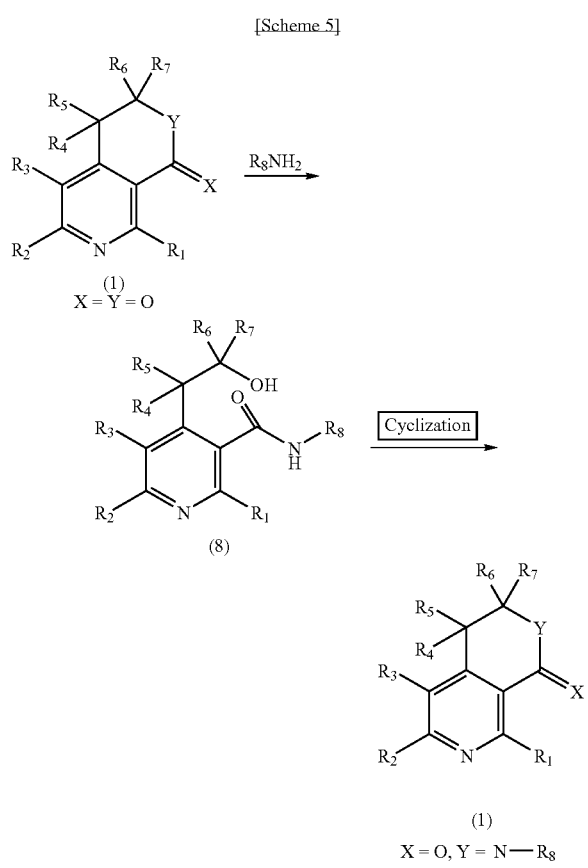

In the above reaction scheme 5, $R_1$, $R_2$, $R_3$, $R_4$, $R_5$, $R_6$, $R_7$, $R_8$, X and Y are the same as defined in the above.

According to the method shown in the above reaction scheme 5, the compound of the above formula 1, wherein X and Y are individually an oxygen atom, was first reacted with an amine compound represented by $R_2NH_2$, wherein $R_8$ is the same as defined above, to obtain the compound of the above formula 8, which was then cyclized and the compound of the above formula 1, wherein X is an oxygen atom and Y is N—$R_8$, was finally obtained.

In the above reaction, the cyclization was performed by reacting with triphenylphosphine and diethyl azodicarboxylate in the presence of an organic solvent such as tetrahydrofuran.

The following reaction scheme 6 briefly shows the third method to prepare the compound of the above formula 1, wherein X is an oxygen atom and Y is N—$R_8$.

In the above reaction scheme 6, $R_1$, $R_2$, $R_3$, $R_4$, $R_5$, $R_6$, $R_7$, $R_8$, X and Y are the same as defined in the above, and $R_9$ is a benzyl or 4-methoxybenzyl group.

According to the method shown in the above reaction scheme 6, the compound of the above formula 1, wherein $R_9$ is a benzyl or 4-methoxybenzyl group, was first reduced by a palladium catalyst in the presence of an alcohol solvent, or reacted with an acidic reagent such as p-toluene sulfonic acid or trifluoroacetate in the presence of an organic solvent such as toluene or methylene chloride to obtain the compound of the above formula 1, which was then cyclized and the compound of the above formula 1, wherein X is an oxygen atom and Y is NH, was finally obtained.

Then, the above compound of the formula 1, wherein X is an oxygen atom and Y is NH, was reacted with an alkylyzing reagent represented by $R_8X$ ($R_8$ is the same as defined in the above and X is a halogen atom) along with a base such as sodium hydride, potassium hydride, lithium hydride, potassium carbonate, and sodium carbonate, in the presence of an organic solvent such as tetrahydrofuran or dimethylfomamide, and the compound of the above formula 1, wherein X is an oxygen atom and Y is N—$R_8$, was finally obtained.

The following reaction scheme 7 briefly shows the fourth method to prepare the pyridine compound of the above formula 1, wherein X is an oxygen atom and Y is N—$R_8$.

[Scheme 7]

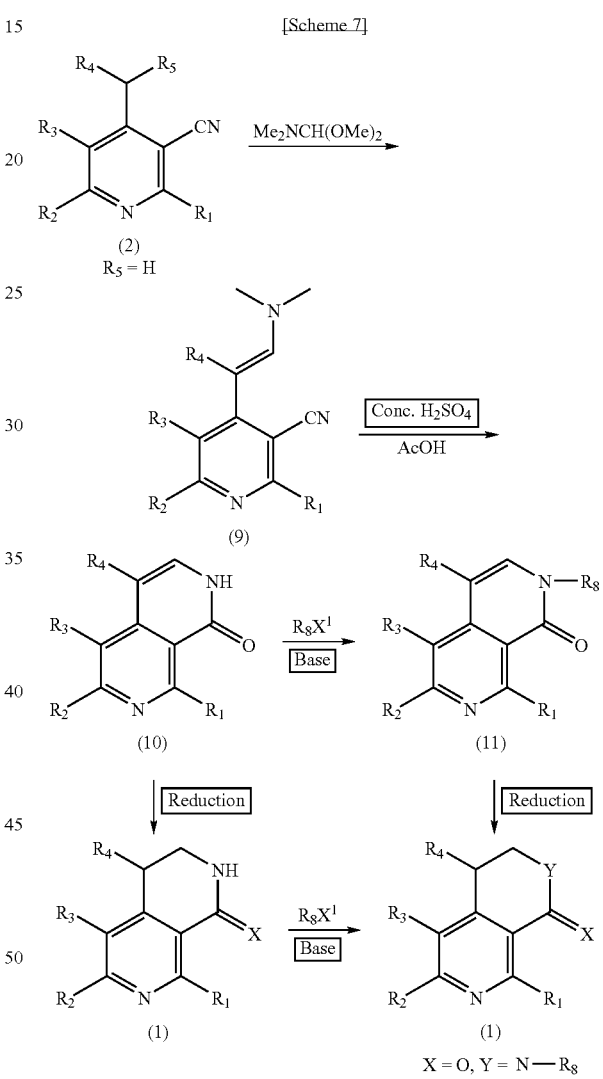

In the above reaction scheme 7, $R_1$, $R_2$, $R_3$, $R_4$, $R_5$, $R_8$, X and Y are the same as defined in the above, and $X^1$ is a halogen atom.

According to the method shown in the above reaction scheme 7, the compound of the above formula 1, wherein $R_5$ is a hydrogen atom, was first reacted with N,N-dimethylformamide dimethylacetal in the presence of an aprotic solvent such as tetrahydrofuran or dimethylformamide and obtained the compound of the above formula 9, which was then cyclized in an acidic condition such as a sulfuric acid or acetic acid and the compound of the above formula 10 was obtained.

Then, the above compound of the formula 10 was reacted with an alkylyzing reagent represented by $R_8X^1$ ($R_8$ is the same as defined in the above and $X^1$ is a halogen atom) along with a base such as sodium hydride, potassium hydride, lithium hydride, potassium carbonate, and sodium carbonate, in the presence of an organic solvent such as tetrahydrofuran or dimethylfomamide, and the compound of the above formula 11 was obtained.

Then, the above compound of the formula 11 was reduced by a palladium catalyst and a hydrogen gas in the presence of an alcohol solvent and the compound of the above formula 1, wherein $R_5$, $R_6$, and $R_7$ are individually a hydrogen atom, X is an oxygen atom and Y is N—$R_8$, was obtained.

Meanwhile, according to the above reaction scheme 7, the compound of the above formula 1, wherein $R_5$, $R_6$, and $R_7$ are individually a hydrogen atom, X is an oxygen atom and Y is N—$R_8$, was also obtained when the above compound of the formula 10 was reduced by a palladium catalyst and a hydrogen gas in the presence of an alcohol solvent.

Then, the above compound of the formula 1, wherein Y is NH, was reacted with an alkylyzing reagent represented by $R_8X^1$ ($R_8$ is the same as defined in the above and $X^1$ is a halogen atom) along with a base such as sodium hydride, potassium hydride, lithium hydride, potassium carbonate, and sodium carbonate, in the presence of an organic solvent such as tetrahydrofuran or dimethylfomamide, and the compound of the above formula 1, wherein $R_5$, $R_6$, and $R_7$ are individually a hydrogen atom, X is an oxygen atom and Y is N—$R_8$, was obtained.

The following reaction scheme 8 briefly shows the method to simultaneously prepare the pyridine compounds of the above formula 1, wherein $R_5$ is a hydrogen atom and X and Y are individually an oxygen atom as well as the pyridine compounds of the above formula 1, wherein $R_5$ is a hydrogen atom, X is an oxygen atom X is an oxygen atom and Y is NH.

[Scheme 8]

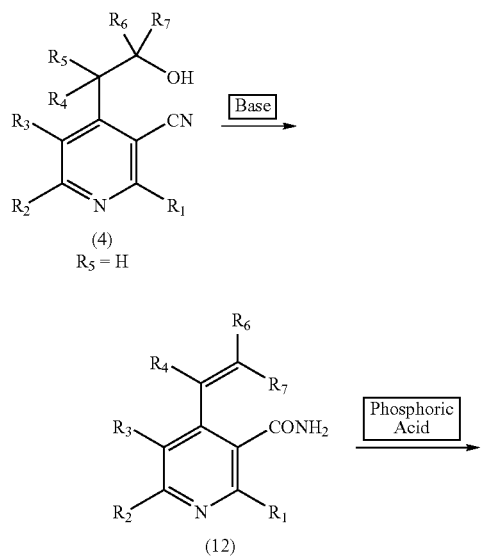

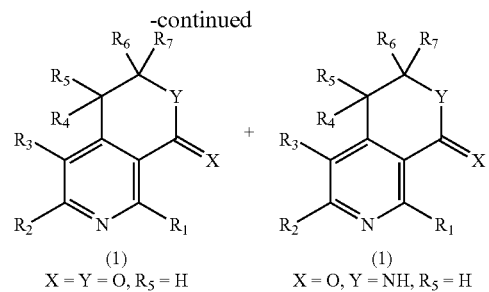

(1)
X = Y = O, $R_5$ = H (1)
X = O, Y = NH, $R_5$ = H

In the above reaction scheme 8, $R_1$, $R_2$, $R_3$, $R_4$, $R_6$, $R_7$, X and Y are the same as defined in the above.

According to the method shown in the above reaction scheme 8, the compound of the above formula 4, wherein $R_5$ is a hydrogen atom, was first reacted with a base such as sodium hydroxide, potassium hydroxide, sodium carbonate and potassium carbonate in the presence of an alcohol solvent and the compound of the above formula 12 was obtained.

Then, the above compound of the formula 12 was cyclized in an acidic condition such as phosphoric acid and the pyridine compounds of the above formula 1, wherein $R_5$ is a hydrogen atom and X and Y are individually an oxygen atom as well as the pyridine compounds of the above formula 1, wherein $R_5$ is a hydrogen atom, X is an oxygen atom X is an oxygen atom and Y is NH, were simultaneously obtained.

The following reaction scheme 9 briefly shows the method to prepare the pyridine compounds of the above formula 1, wherein X is a sulfur atom, Y is an oxygen atom or N—$R_8$.

[Scheme 9]

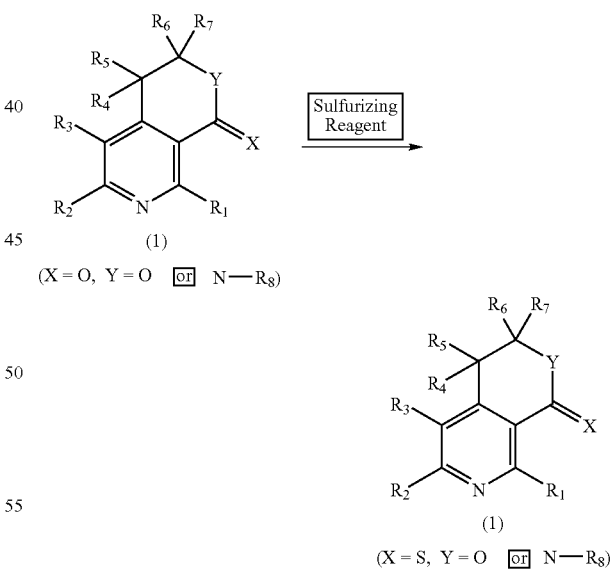

In the above reaction scheme 9, $R_1$, $R_2$, $R_3$, $R_4$, $R_6$, $R_7$, $R_8$, X and Y are the same as defined in the above.

According to the method shown in the above reaction scheme 9, the compound of the above formula 1, wherein X is an oxygen atom, was reacted with a sulfurizing reagent, for example Lawesson's reagent, at a relatively high temperature and the compound of the above formula 1, wherein X is a sulfurn atom, was readily obtained.

Further, of the pyridine compounds according to the present invention, the compound of the formula 1, wherein $R_1$, $R_2$ or $R_3$ are an amino, a $C_1$-$C_{10}$ alkylamino, a $C_4$-$C_9$ cycloalkylamino, a $C_4$-$C_9$ heterocycloalkylamino, an arylamino, an acylamino, a $C_1$-$C_6$ alkylsulfonylamino and an arylsulfonylamino group, can be prepared by the following method. That is, the compound of the formula 1, wherein $R_1$, $R_2$ or $R_3$ are individually a halogen atom, can be converted to a compound of the formula 1, wherein $R_1$, $R_2$ or $R_3$ are an amino, a $C_1$-$C_{10}$ alkylamino, a $C_4$-$C_9$ cycloalkylamino, a $C_4$-$C_9$ heterocycloalkylamino, an arylamino, an acylamino, a $C_1$-$C_6$ alkylsulfonylamino and an arylsulfonylamino group by reacting it with a suitable amine compound in the presence of an organic solvent. In the above amination reaction, it is preferable to use triethylamine as a reaction catalyst and ethanol or acetonitrile as a reaction solvent.

In addition, of the pyridine compounds according to the present invention, the compound of the formula 1, wherein $R_1$, $R_2$ or $R_3$ are benzylamino or 4-methoxy-benzylamino can be converted to a compound of the formula 1, wherein $R_1$, $R_2$ or $R_3$ are amines by an appropriate reduction. The above reduction can be conducted by using a palladium catalyst in the presence of an alcohol solvent, or as an alternative, by using an acidic reagent such as p-toluenesulfonic acid or trifluoroacetic acid in the presence of an organic solvent such as toluene or methylene chloride.

Further, the compound of the formula 1, wherein $R_1$, $R_2$ or $R_3$ are an amino group, can be converted to the compound of the formula 1, wherein $R_1$, $R_2$ or $R_3$ are an acylamino, a $C_1$-$C_6$ alkylsulfonylamino or an arylsulfonylamino group. The above acylation or sulfonization reactions can be performed by using an acylating reagent or a sulfonating reagent along with a base such as triethylamine in the presence of an organic solvent. Examples of the above acylating reagent are acylhalide and acylate anhydride and examples of the above sulfonating reagent are alkylsulfonhalide and arylsulfonhalide. Examples of the above organic solvent are methylene chloride, acetonitrile, dimethylformamide, and tetrahydrofuran.

Further, of the pyridine compounds according to the present invention, the compound of the formula 1, wherein $R_1$, $R_2$ or $R_3$ are a halogen atom, a $C_1$-$C_6$ low alkoxy, an aryloxy or an acyloxy group, can be manufactured as follows.

That is, the compound of the formula 1, wherein $R_1$, $R_2$ or $R_3$ are individually a hydroxyl group, can be converted to the compound of the formula 1, wherein $R_1$, $R_2$ or $R_3$ are individually a halogen atom by reacting it with a suitable halogenating reagent. Examples of the above halogenating reagent are phosphorus oxychloride, thionyl chloride, phosphorus tribromide, N-chlorosuccinimide, and N-iodosuccinimide.

Further, the compound of the formula 1, wherein $R_1$, $R_2$ or $R_3$ are a hydroxy group, can be converted to the compound of the formula 1, wherein $R_1$, $R_2$ or $R_3$ are a $C_1$-$C_6$ low alkoxy, an aryloxy or an acyloxy group by appropriate alkylation. A method of the above alkylation is to react the above compound with a base such as sodium hydride, potassium hydride, lithium hydride, potassium carbonate, and sodium carbonate, along with a suitable alkylating reagent in the presence of an organic solvent such as tetrahydrofuran or dimethylfomamide. Besides, the above alkylation reaction can be performed by reacting a suitable acylating reagent with a base such as triethylamine in an organic solvent such as methylene chloride, chloroform, acetonitrile, dimethylformamide, and tetrahydrofuran Examples of the reagents to be used in the above alkylation reaction are: alkylhalide for an alkylating reagent; an alkylhalide reagent can be used along with an acidic reagent instead of a base; and acylhalide and acylate anhydride can be used as an acylating reagent.

Further, of the pyridine compounds according to the present invention, the compound of the formula 1, wherein $R_1$, $R_2$ or $R_3$ are a $C_1$-$C_6$ low alkyl, a $C_2$-$C_6$ low alkenyl, a $C_4$-$C_9$ cycloalkyl, a $C_4$-$C_9$ heterocycloalkyl, an aryl, a heteroaryl, a $C_1$-$C_{10}$ aralkyl or a $C_1$-$C_{10}$ heteroaralkyl, can be manufactured from the compound of the formula 1, wherein $R_1$, $R_2$ or $R_3$ are a halogen atom by the following method. That is, the compound of the formula 1, wherein $R_1$, $R_2$ or $R_3$ are a $C_1$-$C_6$ low alkyl, a $C_2$-$C_6$ low alkenyl, a $C_4$-$C_9$ cycloalkyl, a $C_4$-$C_9$ heterocycloalkyl, an aryl, a heteroaryl, a $C_1$-$C_{10}$ aralkyl or a $C_1$-$C_{10}$ heteroaralkyl group, can be manufactured by reacting the compound of the formula 1, wherein $R_1$, $R_2$ or $R_3$ are a halogen atom, with an iron catalyst such as Fe $(acac)_3$ and an alkylating reagent or an arylating reagent in the presence of an organic solvent.

The above-mentioned alkylating reagent or an arylating reagent are preferably a Grignard reagent represented by $RMgX^1$, wherein R is a $C_1$-$C_6$ low alkyl, a $C_2$-$C_6$ low alkenyl, a $C_4$-$C_9$ cycloalkyl, a $C_4$-$C_9$ heterocycloalkyl, an aryl, a heteroaryl, a $C_1$-$C_{10}$ aralkyl or a $C_1$-$C_{10}$ heteroaralkyl group, $X^1$ is a halogent atom.

Further, the compound of the formula 1, wherein $R_1$, $R_2$ or $R_3$ are a hydroxy group, can be converted to the compound of the formula 1, wherein $R_1$, $R_2$ or $R_3$ are a $C_2$-$C_6$ low alkenyl, an aryl, or a heteroaryl group, by using a palladium catalyst such as $Pd(PPh_3)_4$ along with an appropriate alkylating reagent or arylating reagent in the presence of an organic solvent.

In the above reaction, the alkylating reagent or arylating reagent is an alkenyl tin compound, an aryl tin compound or a heteroaryl tin compound represented by $RSnR'_3$, wherein R is a $C_2$-$C_6$ low alkenyl, an aryl, or a heteroaryl group, R' is a $C_1$-$C_6$ low alkyl group, preferably a butyl group.

Further, the compound of the formula 1, wherein $R_1$, $R_2$ or $R_3$ are a hydroxy group, can be converted to the compound of the formula 1, wherein $R_1$, $R_2$ or $R_3$ are an aryl or a heteroaryl group, by using a palladium catalyst such as $Pd(PPh_3)_4$ along with a base such as sodium carbonate, potassium carbonate, cesium carbonate, sodium hydroxide, and potassium hydroxide, as well as an appropriate alkylating reagent or arylating reagent in the presence of an organic solvent such as toluene and benzene. The above arylating reagent is preferably an aryl boron compound or a heteroaryl boron compound represented by $RB(OH)_2$, wherein R is an aryl or heteroaryl group.

In another embodiment, the present invention provides a compound of the above formula 1 and its pharmaceutically acceptable salts as an effective therapeutic component.

The pharmaceutical composition of the present invention can be prepared in a dosage form suitable for oral and parenteral administration by comprising the compound of the above formula 1 or its pharmaceutically acceptable salts along with a typical carrier, an adjuvant, or a diluent. In case of a preparation for oral administration, it can be formulated in tablets, capsules, solutions, syrups, and suspensions. In case of a preparation for parenteral administration, it can be formulated as preparations for intraperitoneal, hypodermic, intramuscular and transdermal injections.

The effective daily dosage of the pharmaceutical composition of the present invention for adults as an anti-inflammatory and analgesic agent is about 0.01 to 1,000 mg/day and it can vary depending on the age, body weight, sex, type of administration, health conditions and level of any existing diseases. The administration can be conducted once daily or several times daily with appropriate aliquots after consultation with a doctor or a pharmacist.

In a still another embodiment, the present invention provides a use of a pharmaceutical composition comprising the compound of the above formula 1 or its pharmaceutically acceptable salts for the treatment and prevention of diseases.

That is, the present invention comprises a compound of the above formula 1 or its pharmaceutically acceptable salts to be useful as a therapeutic agent for treating inflammatory diseases, immune diseases, chronic inflammatory diseases and an anti-inflammatory and analgesic agent, and a medical use of a pharmaceutical composition containing the same.

The pharmaceutical composition of the present invention is effective in treating diseases caused by TNF-α, IL-1α, IL-1β and IFN-γ. More specifically, it is effective in treating diseases such as (i) inflammatory diseases or immune diseases such as rheumatic arthritis, multiple sclerosis, Crohn's disease, infectious intestinal diseases such as ulcerative colitis, graft-versus-host disease, systemic erythematosus lupus, toxic shock syndrome, osteoarthritis and insulin-dependent diabetes; (ii) chronic inflammatory diseases such as psoriatic arthritis, psoriatis, ankylosing spondylitis, adult-onset Still's disease, polymyositis, dermatomyositis, vasculitis such as Behcet disease and Wegener's granulomatosis; and is also effective as (iii) an anti-inflammatory and analgesic agent. In addition, it is effective in treating diseases such as glomerulonephritis, dermatitis, asthma, stroke, cardiac infarction, acute respiratory distress syndrome, postinjury multiple organ failure, purulent meningitis, necrotizing enterocolitis, parahemodialysis syndrome, septic shock, and post-menopausal osteoporosis.

EXAMPLES

A better understanding of the present invention may be obtained in light of the following examples which are set forth to illustrate, but are not to be construed to limit the present invention.

Example 1

Synthesis of (3-cyano-pyridine-4-yl)-acetic acid methyl ester 2.52 g of 4-methyl-nicotinonitrile was dissolved in 15 mL of anhydrous THF and dropwisely added with 45 mL of 1M LHMDS at −78° C. and stirred for about 1 hour. At the temperature the above mixture was dropwisely added with 1.98 mL of dimethylcarbonate, stirred for about 1 hour. The mixture was then heated to 0° C. and stirred further for about 2 hours. The above mixture was added with 5 mL of saturated solution of ammonium chloride, diluted with 300 mL ethylacetate. Then, the organic solvent layer was washed with water, and saturated solution of sodium chloride, dried with anhydrous sodium sulfate and filtered. The filtrate was concentreated under reduced pressure and a silica gel column chromatography was performed on the resulting residue by using a mixed eluant of ethylacetate and hexane, wherein ethylacetate and hexane are mixed in 1:3 volume ratio, and 3.21 g (85%) of (3-cyano-pyridine-4-yl)-acetic acid methyl ester was obtained in colorless oil.

$^1$H NMR(300 MHz, CDCl$_3$) δ 8.87 (s, 1H), 8.75(d, 1H, J=5.1 Hz), 7.41(d, 1H, J=5.1 Hz), 3.89(s, 2H), 3.77 (s, 3H).

Example 2

Synthesis of 4-(2-hydroxy-ethyl)-nicotinonitrile 1.58 g of (3-cyano-pyridine-4-yl)-acetic acid methyl ester was dissolved in 18 mL of ethanol and slowly added with 682 mg of sodium borohydride at −0° C. and stirred for about 2 hours. The above mixture was added with 3 mL of saturated solution of ammonium chloride, diluted with 200 mL ethylacetate. Then, the organic solvent layer was washed with water, and saturated solution of sodium chloride, dried with anhydrous sodium sulfate and filtered. The filtrate was concentreated under reduced pressure and a silica gel column chromatography was performed on the resulting residue by using a mixed eluant of methylene chloride and methanol, wherein methylene chloride and methanol are mixed in 50:1 volume ratio, and 1.02 g (74%) of 4-(2-hydroxy-ethyl)-nicotinonitrile was obtained in colorless oil.

$^1$H NMR(300 MHz, CDCl$_3$) δ 8.82(s, 1H), 8.69(d, 1H, J=5.4 Hz), 7.39(d, 1H, J=5.4 Hz), 3.99(t, 2H, J=6.3 Hz), 3.10(t, 2H, J=6.3 Hz).

Example 3

Synthesis of 3,4-dihydro-pyrano[3,4-c]pyridine-1-on 765 mg of 4-(2-hydroxy-ethyl)-nicotinonitrile was added with 13.6 mL of conc. HCl and stirred for about 12 hours while refluxing. The above mixture was concentrated under reduced pressure to remove the solvent. The filtrate was dissolved in water and the water layer was alkalinized by saturated solution of sodium hydrogen carbonate, and then extracted using ethyl acetate. Then, the organic solvent layer was washed with saturated solution of sodium chloride, dried with anhydrous sodium sulfate and filtered. The filtrate was concentreated under reduced pressure and a column chromatography was performed on the resulting residue by using a mixed eluant of ethylacetate and hexane, wherein ethylacetate and hexane are mixed in 1:2 volume ratio, and 760 mg (98%) of 3,4-dihydro-pyrano[3,4-c]pyridine-1-on was obtained in white solid.

$^1$H NMR(300 MHz, CDCl$_3$) δ 9.25(s, 1H), 8.72(d, 1H, J=4.8 Hz), 7.22(d, 1H, J=5.1 Hz), 4.58(t, 2H, J=6.0 Hz), 3.08(t, 2H, J=6.0 Hz).

Example 4

Synthesis of (5-cyano-2-methyl-pyridine-4-yl)-acetic acid methyl ester 3.2 g (77%) of (5-cyano-2-methyl-pyridinefyl)-acetic acid methyl ester was obtained in colorless oil using the method same as in Example 1 except that 2.88 g of 4,6-dimethyl-nicotinonitrile was used instead of 4-methyl-nicotinonitrile.

$^1$H NMR(300 MHz, CDCl$_3$) δ 8.75(s, 1H), 7.25(s, 1H), 3.83(s, 2H), 3.76(s, 3H), 2.63(s, 3H).

Example 5

Synthesis of 4-(2-hydroxy-ethyl)-6-methyl-nicotinonitrile 1.5 g (65%) of 4-(2-hydroxy-ethyl)-6-methyl-nicotinonitrile was obtained in colorless oil using the method same as in Example 2 except that 2.7 g of (5-cyano-2-methyl-pyridine-4-yl)-acetic acid methyl ester was used instead of (3-cyano-pyridine-4-yl)-acetic acid methyl ester.

$^1$H NMR(300 MHz, CDCl$_3$) δ 8.71(s, 1H), 7.23(s, 1H), 3.97 (t, 2H, J=6.3 Hz), 3.04(t, 2H, J=6.3 Hz), 2.61(s, 3H).

Example 6

Synthesis of 6-methyl-3,4-dihydro-pyrano[3,4-c]pyridine-1-on 1.19 g (99.4%) of 6-methyl-3,4-dihydro-pyrano[3,4-c]pyridine-1-on was obtained in white solid using the method same as in Example 3 except that 981 mg of 4-(2-hydroxy-ethyl)-6-methyl-nicotinonitrile was used instead of 4-(2-hydroxy-ethyl)-nicotinonitrile.

$^1$H NMR(300 MHz, CDCl$_3$) δ 9.01(s, 1H), 7.79(s, 1H), 4.60(t, 2H, J=6.0 Hz), 3.26(t, 2H, J=6.0 Hz), 2.70(s, 3H).

Example 7

Synthesis of (3-cyano-5-vinyl-pyridine-4-yl)-acetic acid methyl ester 2.5 g (74%) of (3-cyano-5-vinyl-pyridine-4-yl)-acetic acid methyl ester was obtained in colorless oil using the method same as in Example 1 except that 2.42 g of 4-methyl-5-vinyl-nicotinonitrile was used instead of 4-methyl-nicotinonitrile.

$^1$H NMR(300 MHz, CDCl$_3$) δ 8.83(s, 1H), 8.77 (s, 1H), 6.81(dd, 1H, J=17.4 Hz, 11.1 Hz), 5.78(d, 1H, J=17.4 Hz), 5.60(d, 1H, J=11.1 Hz), 3.95(s, 2H), 3.74(s, 3H).

Example 8

Synthesis of 4-(2-hydroxy-ethyl)-5-vinyl-nicotinonitrile 1.04 g (60%) of 4-(2-hydroxy-ethyl)-5-vinyl-nicotinonitrile was obtained in white solid using the method same as in Example 2 except that 2.0 g of (3-cyano-5-vinyl-pyridine-4-yl)-acetic acid methyl ester was used instead of (3-cyano-pyridine-4-yl)-acetic acid methyl ester.

$^1$H NMR(300 MHz, CDCl$_3$) δ 8.92(s, 1H), 8.84(s, 1H), 7.05(dd, 1H, J=17.4 Hz, 11.1 Hz), 5.96(d, 1H, J=17.4 Hz), 5.55(d, 1H, J=11.1 Hz), 3.61(t, 1H, J=6.6 Hz), 3.04(t, 2H, J=6.6 Hz).

Example 9

Synthesis of 5-vinyl-3,4-dihydro-pyrano[3,4-c]pyridine-1-on 817 mg (85%) of 5-vinyl-3,4-dihydro-pyrano[3,4c]pyridine-1-on was obtained in white solid using the method same as in Example 3 except that 780 mg of 4-(2-hydroxy-ethyl)-5-vinyl-nicotinonitrile was used instead of 4-(2-hydroxy-ethyl)-nicotinonitrile.

$^1$H NMR(300 MHz, CDCl$_3$) δ 9.17 (s, 1H), 8.84(s, 1H), 6.81(dd, 1H, J=17.7 Hz, 11.1 Hz), 5.81(d, 1H, J=17.7 Hz), 5.59(d, 1H, J=11.1 Hz), 4.56(t, 2H, J=6.0 Hz), 3.09(t, 2H, J=6.0 Hz)

Example 10

Synthesis of (2,6-dichloro-3-cyano-pyridine-4-yl)-acetic acid methyl ester 1.8 g (54%) of (2,6-dichloro-3-cyano-pyridinefyl)-acetic acid methyl ester was obtained in colorless oil using the method same as in Example 1 except that 2.57 g of 2,6-dichloro-4-methyl-nicotinonitrile was used instead of 4-methyl-nicotinonitrile.

$^1$H NMR(300 MHz, CDCl$_3$) δ 7.40(s, 1H), 3.88(s, 2H), 3.78(s, 3H).

Example 11

Synthesis of 2,6-dichloro-4-(2-hydroxy-ethyl)-nicotinonitrile 600 mg (68%) of 2,6-dichloro-4-(2-hydroxy-ethyl)-nicotinonitrile was obtained in colorless oil using the method same as in Example 2 except that 1.0 g of 2,6-dichloro-(3-cyano-pyridine-4-yl)-acetic acid methyl ester was used instead of (3-cyano-pyridine-4-yl)-acetic acid methyl ester.

$^1$H NMR(300 MHz, CDCl$_3$) δ 7.40(s, 1H), 3.88(s, 2H), 3.78(s, 3H). $^1$H NMR(300 MHz, CDCl$_3$) δ 7.40(s, 1H), 3.98 (t, 2H, J=6.0 Hz), 3.09(t, 2H, J6.0 Hz).

Example 12

Synthesis of 6,8-dichloro-3,4-dihydro-pyrano[3,4-c]pyridine-1-on 270 mg (90%) of 6,8-dichloro-3,4-dihydro-pyrano[3,4-c]pyridine-1-on was obtained in pale yellow solidusing the method same as in Example 3 except that 300 mg of 2,6-dichloro-4-(2-hydroxy-ethyl)-nicotinonitrile was used instead of 4-(2-hydroxy-ethyl)-nicotinonitrile.

$^1$H NMR(300 MHz, CDCl$_3$) δ 7.40(s, 1H), 4.60(t, 2H, J=6.0 Hz), 3.10(t, 2H, J=6.0 Hz).

Example 13

Synthesis of (2,6-bis-benzyloxy-3-cyano-pyridine-4-yl)-acetic acid methyl ester 840 mg (35%) of (2,6-bis-benzyloxy-3-cyano-pyridine-4-yl)-acetic acid methyl ester was obtained in colorless oil using the method same as in Example 1 except that 2.05 g of 2,6-bis-benzyloxy-4-methyl-nicotinonitrile was used instead of 4-methyl-nicotinonitrile.

$^1$H NMR(300 MHz, CDCl$_3$) δ 7.45-7.31(m, 10H), 6.41(s, 1H), 5.46(s, 2H), 5.35(s, 2H), 3.78(s, 2H), 3.74(s, 3H).

Example 14

Synthesis of 2,6-bis-benzyloxy-4-(2-hydroxy-ethyl)-nicotinonitrile 285 mg (62%) of 2,6-bis-benzyloxy-4-(2-hydroxy-ethyl)-nicotinonitrile was obtained in colorless oil using the method same as in Example 2 except that 500 mg of (2,6-bis-benzyloxy-3-cyano-pyridine-4-yl)-acetic acid methyl ester was used instead of (3-cyano-pyridine-4-yl)-acetic acid methyl ester.

$^1$H NMR(300 MHz, CDCl$_3$) δ 7.44-7.30(m, 10H), 6.41(s, 1H), 5.44(s, 2H), 5.35(s, 2H), 3.97 (t, 2H, J=6.3 Hz), 3.10(t, 2H, J=6.3 Hz).

Example 15

Synthesis of 6,8-dihydroxy-3,4-dihydro-pyrano[3,4-c]pyridine-1-on 98 mg (98%) of 6,8-dihydroxy-3,4-dihydro-pyrano[3,4-c]pyridine-1-on was obtained in solid oil using the method same as in Example 3 except that 200 mg of 2,6-bis-benzyloxy-4-(2-hydroxy-ethyl)-nicotinonitrile was used instead of 4-(2-hydroxy-ethyl)-nicotinonitrile.

$^1$H NMR(300 MHz, CDCl$_3$) δ 5.48(s, 1H), 4.44(t, 2H, J=6.3 Hz), 2.88(t, 2H, J=6.3 Hz).

Example 16

Synthesis of 2-methoxy-4,6-dimethyl-nicotinonitrile 2-chloro-4,6-dimethyl-nicotinonitrile (2.5 g, 15.01 mmol) was dissolved in anhydrous methanol(70 mL), added with sodium methoxide (4.27 g, 75.03 mmol) at 0° C. and stirred for about 10 hours at nitrogen atmosphere. The above mixture was concentrated under reduced pressure and then neutrailized with a saturated solution of ammonium chloride and then extracted twice with 150 mL of methylenechloride. The resulting organic layer was dried using anhydrous sodium sulfate, filtered and concentrated. A silica gel column chromatography (20% EtOAc/Hexanes) was performed on the resulting residue and 2.41 g (99%) of 2-methoxy-4,6-dimethyl-nicotinonitrile was obtained in white solid.

$^1$H NMR(300 MHz, CDCl$_3$) δ 2.44(s, 3H), 2.45(s, 3H), 4.01(s, 3H), 6.68(s, 1H).

Example 17

Synthesis of (3-cyano-2-methoxy-6-methyl-pyridine-4-yl)-acetic acid methyl ester 3.03 g (97%) of (3-cyano-2-methoxy-6-methyl-pyridine-4-yl)-acetic acid methyl ester was obtained using the method same as in Example 1 except that 2.3 g of 2-methoxy4,6-dimethyl-nicotinonitrile was used instead of 4-methyl-nicotinonitrile.

$^1$H NMR(300 MHz, CDCl$_3$) δ 2.49(s, 3H), 3.75(s, 3H), 3.78(s, 2H), 4.03(s, 3H), 6.79(s, 1H).

Example 18

Synthesis of 4-(2-hydroxy-ethyl)-2-methoxy-6-methyl-nicotinonitrile 2.04 g (88%) of 4-(2-hydroxy-ethyl)-2-methoxy-6-methyl-nicotinonitrile was obtained using the method same as in Example 2 except that 2.65 g of (3-cyano-2-methoxy-6-methyl-pyridine-4yl)-acetic acid methyl ester was used instead of (3-cyano-pyridine-4-yl)-acetic acid methyl ester.

$^1$H NMR(300 MHz, CDCl$_3$) δ 1.55(brt, 1H, J=5.4 Hz), 2.48(s, 3H), 3.00(t, 2H, J=6.3 Hz), 3.92-3.97(m, 2H), 4.02(s, 3H), 6.78(s, 1H).

Example 19

Synthesis of 8-hydroxy-6-methyl-3,4-dihydro-pyrano[3,4-c]pyridine-1-on 337 mg (84%) of 8-hydroxy-6-methyl-3,4-dihydro-pyrano[3,4-c]pyridine-1-on was obtained using the method same as in Example 3 except that 430 mg of 4-(2-hydroxy-ethyl)-2-methoxy-6-methyl-nicotinonitrile was used instead of 4-(2-hydroxy-ethyl)-nicotinonitrile.

$^1$H NMR(300 MHz, DMSO-d$_6$) δ 2.30(s, 3H), 2.63(t, 2H, J=6.0 Hz), 4.44(t, 2H, J=6.0 Hz), 6.67 (s, 1H), 12.26(brs, 1H).

Example 20

Synthesis of 8-chloro-6-methyl-3,4-dihydro-pyrano[3,4-c]pyridine-1-on 8-hydroxy-6-methyl-3,-dihydro-pyrano[3,4-c]pyridine-1-on (280 mg, 1.561 mmol) was dissolved in phosphorous oxychloride (POCl$_3$, 2.5 mL) and heated to reflux for about 15 hours at nitrogen atmosphere. The above mixture was added to 20 mL of distilled water and neutralized by slowly adding a saturated solution of sodium carbonate stirring at 0° C. and then extracted twice using 100 mL of methylene chloride (MC). The resulting organic layer was dried using anhydrous sodium sulfate, filtered and concentrated. A silica gel column chromatography (2% MeOH/MC) was performed on the resulting residue and 273 mg (89%) of 8-chloro-6-methyl-3,4-dihydro-pyrano[3,4-c]pyridine-1-on was obtained in white solid.

$^1$H NMR(300 MHz, CDCl$_3$) δ 2.59(s, 3H), 3.03(t, 2H, J=6.0 Hz), 4.48(t, 2H, J=6.0 Hz), 7.03(s, 1H).

Example 21

Synthesis of 6-methyl-1-oxo-3,4-dihydro-1H-pyrano[3,4-c]pyridine-8-yl acetic ester 8-hydroxy-6-methyl-3,4-dihydro-pyrano[3,4-c]pyridine-1-on (280 mg, 1.561 mmol) was suspended in anhydrous dimethylformamide (DMF, 6 mL) and then dropwisely added with triethylamine (0.65 mL, 4.683 mmol) and acetic anhydride (0.44 mL, 4.683 mmol) in this order and stirred for about 24 hours at 70° C. under the nitrogen atmosphere. The mixture was concentrated under reduced pressure, added with 20 mL of distilled water and then extracted twice with 30 mL of methylene chloride. The resulting organic layer was dried using anhydrous sodium sulfate, filtered and concentrated. A silica gel column chromatography (2% MeOH/MC) was performed on the resulting residue and 224 mg (65%) of 6-methyl-1-oxo-3,4-dihydro-1H-pyrano[3,4-c]pyridine-8-yl acetic ester was obtained in white solid.

$^1$H NMR(300 MHz, CDCl$_3$) δ 2.40(s, 3H), 2.58(s, 3H), 3.05(t, 2H, J=6.0 Hz), 4.51(t, 2H, J=6.0 Hz), 7.05(s, 1H).

Example 22

Synthesis of 8-methoxy-6-methyl-3,4-dihydro-pyrano[3,4-c]pyridine-1-on 8-hydroxy-6methyl-3,4-dihydro-pyrano[3,4-c]pyridine-1-on (324 mg, 1.809 mmol) and anhydrous potassium carbonate were suspended in anhydrous dimethylformamide (DMF, 10 mL) and then dropwisely added with iodomethane (1.13 mL, 18.09 mmol) and stirred for about 4 hours at 70° C. under the nitrogen atmosphere. The mixture was concentrated under reduced pressure, added with 50 mL of distilled water and then extracted six times with 40 mL of 10% MeOH/MC. The resulting organic layer was dried using anhydrous sodium sulfate, filtered and concentrated. A silica gel column chromatography (10% MeOH/MC) was performed on the resulting residue and 215 mg (62%) of 8-methoxymethyl-3,4-dihydro-pyrano[3,4-c]pyridine-1-on was obtained in pale yellow solid.

$^1$H NMR(300 MHz, DMSO-$d_6$) δ 2.41(s, 3H), 2.82(t, 2H, J=6.0 Hz), 3.42(s, 3H), 4.29(t, 2H, J=6.0 Hz), 6.20(s, 1H).

Example 23

Synthesis of 2,4,6trimethyl-nicotinonitrile 2-chloro-4,6-dimethyl-nicotinonitrile (700 mg, 4.201 mmol) and Pd(PPh$_3$)$_4$ (243 mg, 0.210 mmol) were dissolved in 20 mL of anhydrous THF, added with methylzinc chloride (2M CH$_3$ZnCl/THF, 12.6 mL, 25.21 mmol) and refluxed for about 40 hours under the nitrogen atmosphere. The mixture was added to a saturated EDTA solution (50 mL), and neutralized with potassium carbonate while stirring at 0° C. and then extracted twice with 150 mL of methylene chloride. The resulting organic layer was dried using anhydrous sodium sulfate, filtered and concentrated. A silica gel column chromatography (25% EtOAc/Hexanes) was performed on the resulting residue and 535 mg (87%) of 2,4,6-trimethyl-nicotinonitrile was obtained in white solid.

$^1$H NMR(300 MHz, CDCl$_3$) δ 2.48(s, 3H), 2.54(s, 3H), 2.72(s, 3H), 6.95(s, 1H).

Example 24

Synthesis of (3-cyano-2,6-dimethyl-pyridine-4-yl)-acetic acid methyl ester 592 mg (80%) of (3-cyano-2,6-dimethyl-pyridine-4-yl)-acetic acid methyl ester was obtained in pale yellow oil using the method same as in Example 1 except that 2,4,6-trimethyl-nicotinonitrile (530 mg, 3.625 mmol) was used instead of 4-methyl-nicotinonitrile.

$^1$H NMR(300 MHz, CDCl$_3$) δ 2.57 (s, 3H), 2.74(s, 3H), 3.75(s, 3H), 3.80(s, 2H), 7.06(s, 1H).

Example 25

Synthesis of 4-(2-hydroxy-ethyl)-2,6-dimethyl-nicotinonitrile 433 mg (87%) of 4-(2-hydroxy-ethyl)-2,6-dimethyl-nicotinonitrile was obtained in white solid using the method same as in Example 2 except that (3-cyano-2,6-dimethyl-pyridine-4-yl)-acetic acid methyl ester (580 mg, 2.840 mmol) was used instead of (3-cyano-pyridine-4-yl)-acetic acid methyl ester.

$^1$H NMR(300 MHz, CDCl$_3$) δ 1.70(t, 1H, J=5.7 Hz), 2.56 (s, 3H), 2.73(s, 3H), 3.03(t, 2H, J=6.3 Hz), 3.97 (q, 2H, J=6.0 Hz), 7.05(s, 1H).

Example 26

Synthesis of 6,8-dimethyl-3,4-dihydro-pyrano[3,4-c]pyridine-1-on 274 mg (97%) of 6,8-dimethyl-3,4-dihydro-pyrano[3,4-c]ppyridine-1-on was obtained in white solid using the method same as in Example 3 except that 4-(2-hydroxy-ethyl)-2,6-dimethyl-nicotinonitrile (280 mg, 1.589 mmol) was used instead of 4-(2-hydroxy-ethyl)-nicotinonitrile.

$^1$H NMR(300 MHz, CDCl$_3$) δ 2.56(s, 3H), 2.87 (s, 3H), 2.97 (t, 2H, J=6.0 Hz), 4.45(t, 2H, J=6.0 Hz), 6.92(s, 1H).

Example 27

Synthesis of 6-methyl-8-furan-2-yl-3,4-dihydro-pyrano[3,4-c]pyridine-1-on 8-chloro-6-methyl-3,4-dihydro-pyrano[3,4-c]pyridine-1-on (250 mg, 1.265 mmol) and Pd(PPh$_3$)$_4$ (146 mg, 0.127 mmol) were dissolved in 12 mL of anhydrous toluene, dropwisely added with 2-(tributylstannyl)furan (0.80 mL, 2.530 mmol) and then heated to reflux for about 15 hours under the nitrogen atmosphere. The mixture was added with 15 mL of 2% KF solution and 20 mL of distilled water while stirring at 0° C. and then extracted twice with 50 mL of methylene chloride. The resulting organic layer was dried using anhydrous sodium sulfate, filtered and concentrated. A silica gel column chromatography (5% EtOAc/MC) was performed on the resulting residue and 225 mg (78%) of 6-methyl-8-furan-2-yl-3,4-dihydro-pyrano[3,4-c]pyridine-1-on was obtained in white solid.

$^1$H NMR(300 MHz, CDCl$_3$) δ 2.63(s, 3H), 3.01(t, 2H, J=5.7 Hz), 4.52(t, 2H, J=5.7 Hz), 6.54(dd, 1H, J=3.6, 1.8 Hz), 6.97 (s, 1H), 7.12(dd, 1H, J=3.6, 0.6 Hz), 7.57 ((dd, 1H, J=1.8, 0.6 Hz).

Example 28

Synthesis of 6-methyl-8-thiophene-2-yl-3,4-dihydro-pyrano[3,4-c]pyridine-1-on 247 mg (80%) of 6-methyl-8-thiophene-2-yl-3,4-dihydro-pyrano[3,4-c]pyridine-1-on was obtained in white solid using the method same as in Example 27 except that 2-(tributylstannyl)thiophene was used instead of 2-(tributylstannyl)furan.

$^1$H NMR(300 MHz, CDCl$_3$) δ 2.59(s, 3H), 3.00(t, 2H, J=5.7 Hz), 4.51(t, 2H, J=5.7 Hz), 6.92(s, 1H), 7.07 (dd, 1H, J=5.1, 3.9 Hz), 7.45(dd, 1H, J=5.1, 1.2 Hz), 7.70(dd, 1H, J=3.9, 1.2 Hz).

Example 29

Synthesis of 6-methyl-8-pyridine-2-yl-3,4-dihydro-pyrano[3,4-c]pyridine-1-on 228 mg (75%) of 6-methyl-8-pyridine-2-yl-3,4-dihydro-pyrano[3,4-c]pyridine-1-on was obtained in white solid using the method same as in Example 27 except that 2-(tributylstannyl)pyridine was used instead of 2-(tributylstannyl)furan.

$^1$H NMR(300 MHz, CDCl$_3$) δ 2.66(s, 3H), 3.05(t, 2H, J=5.7 Hz), 4.58(t, 2H, J=5.7 Hz), 7.12(s, 1H), 7.31-7.35(m, 1H), 7.67-7.70(m, 1H), 7.80-7.85(m, 1H), 8.62-8.64(m, 1H).

Example 30

Synthesis of 8-(4-fluorophenyl)-6-methyl-3,4-dihydro-pyrano[3,4-c]pyridine-1-on 8-chloro-6-methyl-3,4-dihydro-pyrano[3,4-c]pyridine-1-on (250 mg, 1.265 mmol), 4-fluorophenyl boronic acid (265 mg, 1.898 mmol), Pd(PPh$_3$)$_4$ (146 mg, 0.127 mmol) and anhydrous potassium carbonate (350 mg, 2.530 mmol) were suspended in 10 mL of anhydrous toluene and then refluxed for about 15 hours under the nitrogen atmosphere. The mixture was added with 20 mL of a saturated solution of ammonium chloride and 10 mL of distilled water while stirring at 0° C. and then extracted twice with 60 mL of methylene chloride. The resulting organic layer was dried using anhydrous sodium sulfate, filtered and concentrated. A silica gel column chromatography (5% EtOAc/MC) was performed on the resulting residue and 135 mg (42%) of 8-(4-fluorophenyl)-6-methyl-3,4-dihydro-pyrano[3,4-c]pyridine-1-on was obtained in pale yellow solid.

$^1$H NMR(300 MHz, CDCl$_3$) δ 2.64(s, 3H), 3.04(t, 2H, J=6.0 Hz), 4.56(t, 2H, J=6.0 Hz), 7.05(s, 1H), 7.08-7.14(m, 2H), 7.51-7.55(m, 2H).

Example 31

Synthesis of 8-(4-chloro-phenyl)-6-methyl-3,4-dihydro-pyrano[3,4-c]pyridine-1-on 95 mg (27%) of 8-(4-chloro-phenyl)-6-methyl-3,4-dihydro-pyrano[3,4-c]pyridine-1-on was obtained in pale yellow solid using the method same as in Example 30 except that 4-chlorophenyl boronic acid was used instead of 4-fluorophenyl boronic acid.

$^1$H NMR(300 MHz, CDCl$_3$) δ 2.64(s, 3H), 3.05(t, 2 H, J=5.7 Hz), 4.56(t, 2H, J=5.7 Hz), 7.06(s, 1H), 7.38-7.41(m, 2H), 7.46-7.50(m, 2H).

Example 32

Synthesis of 6-methyl-8-piperidine-1-yl-3,4-dihydro-pyrano[3,4-c]pyridine-1-on 8-chloro-6-methyl-3,4-dihydro-pyrano[3,4-c]pyridine-1-on (250 mg, 1.265 mmol) was suspended in 8 mL of anhydrous acetonitrile and then dropwisely added with 1.0 mL of triethylamine and piperidine (0.19 mL, 1.898 mmol) in this order and heated to reflux for about 3 hours under the nitrogen atmosphere. The mixture was concentrated under reduced pressure, added with 10 mL of a saturated solution of ammonium chloride and 10 mL of distilled water and then extracted twice with 30 mL of methylene chloride. The resulting organic layer was dried using anhydrous sodium sulfate, filtered and concentrated. A silica gel column chromatography (10% EtOAc/MC) was performed on the resulting residue and 296 mg (95%)of 6-methyl-8-piperidine-1-yl-3,4-dihydro-pyrano[3,4-c]pyridine-1-on was obtained in white solid.

$^1$H NMR(300 MHz, CDCl$_3$) δ 1.66(brs, 6H), 2.37 (s, 3H), 2.86(t, 2H, J=5.7 Hz), 3.48(brs, 4H), 4.39(t, 2H, J=5.7 Hz), 6.32(s, 1H).

Example 33

Synthesis of 6-methyl-8-morpholine-4-yl-3,4-dihydro-pyrano[3,4-c]pyridine-1-on 284 mg (90%) of 6-methyl-8-morpholine-4-yl-3,4-dihydro-pyrano[3,4-c]pyridine-1-on was obtained in white solid using the method same as in Example 32 except that 8chloro-6-methyl-3,4-dihydro-pyrano[3,4-c]pyridine-1-on was added with morpholine instead of piperidine.

$^1$H NMR(300 MHz, CDCl$_3$) δ 2.39(s, 3H), 2.90(t, 2H, J=5.7 Hz), 3.53(dd, 4H, J=5.1, 4.2 Hz), 3.82(dd, 4H, J=5.1, 4.2 Hz), 4.41(t, 2H, J=5.7 Hz), 6.42(s, 1H).

Example 34

Synthesis of 6-methyl-8-(4-methyl-piperazine-1-yl)-3,4-dihydro-pyrano[3,4-c]pyridine-1-on 323 mg (98%) of 6-methyl-8-(4-methyl-piperazine-1-yl)-3,4-dihydro-pyrano[3,4-c]pyridine-1-on was obtained in white solid using the method same as in Example 32 except that 8-chloro-6-methyl-3,4-dihydro-pyrano[3,4-c]pyridine-1-on was added with 1-methyl piperazine instead of piperidine.

$^1$H NMR(300 MHz, CDCl$_3$) δ 2.35(s, 3H), 2.38(s, 3H), 2.54(dd, 4H, J=5.1, 4.8 Hz), 2.88(t, 2H, J=5.7 Hz), 3.57 (dd, 4H, J=5.1, 4.8 Hz), 4.40(t, 2H, J=5.7 Hz), 6.38(s, 1H).

Example 35

Synthesis of 8-(4-fluoro-phenylamino)-6-methyl-3,4-dihydro-pyrano[3,4-c]pyridine-1-on 8-chloro-6-methyl-3,4-dihydro-pyrano[3,4-c]pyridine-1-on (200 mg, 1.012 mmol) was dissolved in 5 mL of ethanol and then added with 4-fluoroaniline (224.9 mg, 2.024 mmol) and stirred at 80° C. overnight. The mixture was concentrated under reduced pressure. A silica gel column chromatography (20% EtOAc/Hexane) was performed on the resulting residue and 250 mg (90%) of 8-(4-fluoro-phenylamino)-6-methyl-3,4-dihydro-pyrano[3,4-c]pyridine-1-on was obtained in pale yellow solid.

$^1$H NMR(300 MHz, CDCl$_3$) δ 10.37 (s, 1H), 7.73-7.68(m, 2H), 7.04-6.98(m, 2H), 6.42(s, 1H), 4.50(t, J=6.0 Hz, 2H), 2.93(t, J=6.0 Hz, 2H), 2.42(s, 3H).

Example 36

Synthesis of 6-methyl-8-(4-pyrimidine-2-yl-peperazine-1-yl)-3,4-dihydro-pyrano[3,4-c]pyridine-1-on 170 mg (70%) of 6-methyl-8-(4-pyrimiddine-2-yl-peperazine-1-yl)-3,4-dihydro-pyrano[3,4-c]pyridine-1-on was obtained in white solid using the method same as in Example 35 except that 150 mg of 8-chloro-6-methyl-3,4-dihydro-pyrano[3,4-c]pyridine-1-on was added with 1-(2-pyrimidyl) piperazine 2 HCl instead of 4-fluoro-aniline.

$^1$H NMR(300 MHz, CDCl$_3$) δ 8.31(s, 1H), 8.30(s, 1H), 7.02(d, J=7.2 Hz, 1H), 6.48(t, J=4.8 Hz, 1H), 6.41(s, 1H), 4.44(t, J=6.0 Hz, 2H), 3.95(m, 4H), 3.63(m, 4H), 2.57 (s, 3H), 3.01(t, J=6.0 Hz, 2H).

Example 37

Synthesis of 8-(4-chloro-phenylamino)-6-methyl-3,4-dihydro-pyrano[3,4-c]pyridine-1-on 342 mg (94%) of 8-(4-choro-phenylamino)-6-methyl-3,4-dihydro-pyrano[3,4-c]pyridine-1-on was obtained in white solid using the method same as in Example 35 except that 200 mg of 8-chloro-6-methyl-3,4-dihydro-pyrano[3,4-c]pyridine-1-on was added with 4-chloro-aniline instead of 4-fluoro-aniline.

$^1$H NMR(300 MHz, CDCl$_3$) δ 10.45(s, 1H), 7.74-7.70(m, 2H), 7.28-7.24(m, 2H), 4.50(t, J=6.0 Hz, 2H), 2.94(t, J=6.0 Hz, 2H), 2.46(s, 3H).

Example 38

Synthesis of 8-(4-trifluoromethyl-phenylamino)-6-methyl-3,4-dihydro-pyrano[3,4-c]pyridine-1-on 130 mg (67%) of 8-(4-trifluoromethyl-phenylamino)-6-methyl-3,4-dihydro-pyrano[3,4-c]pyridine-1-on was obtained in white solid using the method same as in Example 35 except that 120 mg of 8-chloro-6-methyl-3,4-dihydro-pyrano[3,4-c]pyridine-1-on was added with 4-trifluoromethyl-aniline instead of 4-fluoro-aniline.
$^1$H NMR(300 MHz, CDCl$_3$) δ 10.67 (s, 1H), 7.91(d, J=8.5 Hz, 2H), 7.57 (d, J=8.5 Hz, 2H), 6.51(s, 1H), 4.51(t, J=6.3 Hz, 2H), 2.96(t, J=6.3 Hz, 2H), 2.49(s, 3H).

Example 39

Synthesis of 6-methyl-8-p-tolylamino-3,4-dihydro-pyrano[3,4-c]pyridine-1-on 188 mg (92%) of 6-methyl-8-p-tolylamino-3,4-dihydro-pyrano[3,4-c]pyridine-1-on was obtained in pale yellow solid using the method same as in Example 35 except that 150 mg of 8-chloro-6-methyl-3,4-dihydro-pyrano[3,4-c]pyridine-1-on was added with 4-methyl-aniline instead of 4-fluoro-aniline.
$^1$H NMR(300 MHz, CDCl$_3$) δ 10.34(s, 1H), 7.64(d, J=8.7 Hz, 2H), 7.13(d, J=8.7 Hz, 2H), 6.38(s, 1H), 4.49(t, J=6.3 Hz, 2H), 2.92(t, J=6.3 Hz, 2H), 2.44(s, 3H), 2.32(s, 3H).

Example 40

Synthesis of 6-methyl-8-phenylamino-3,4-dihydro-pyrano[3,4-c]pyridine-1-on 145 mg (87%) of 6-methyl-8-phenylamino-3,4-dihydro-pyrano[3,4-c]pyridine-1-on was obtained in pale yellow solid using the method same as in Example 35 except that 130 mg of 8-chloro-6-methyl-3,4-dihydro-pyrano[3,4-c]pyridine-1-on was added with aniline instead of 4-fluoro-aniline.
$^1$H NMR(300 MHz, CDCl$_3$) δ 10.44(s, 1H), 7.79-7.76(m, 2H), 7.35-7.30(m, 2H), 7.07-7.01(m, 1H), 6.41(s, 1H), 4.49(t, J=6.0 Hz, 2H), 2.93(t, J=6.0 Hz, 2H), 2.46(s, 3H).

Example 41

Synthesis of 6-methyl-8-phenetylamino-3,4-dihydro-pyrano[3,4-c]pyridine-1-on 175 mg (61%) of 6-methyl-8-phenetylamino-3,4-dihydro-pyrano[3,4-c]pyridine-1-on was obtained in white solid using the method same as in Example 35 except that 200 mg of 8-chloro-6-methyl-3,4-dihydro-pyrano[3,4-c]pyridine-1-on was added with phenetylamine instead of 4-fluoro-aniline.
$^1$H NMR(300 MHz, CDCl$_3$) δ 8.27 (s, 1H), 7.33-7.18(m, 5H), 6.21(s, 1H), 4.42(t, J=6.0 Hz, 2H), 3.77 (dt, J=7.5, 1.8 Hz, 2H), 2.94(t, J=7.5 Hz, 2H), 2.84(t, J=6.0 Hz, 2H).

Example 42

Synthesis of 8-[(benzo[1,3]dioxol-5-ylmethyl)-amino]-6-methyl-3,4-dihydro-pyrano[3,4-c]pyridine-1-on 139 mg (74%) of 8-[(benzo[1,3]dioxol-5-ylmethyl)-amino]-6-methyl-3,4-dihydro-pyrano[3,4-c]pyridine-1-on was obtained in white solid using the method same as in Example 35 except that 120 mg of 8-chloro-6-methyl-3,4-dihydro-pyrano[3,4-c]pyridine-1-on was added with piperonylamine instead of 4-fluoro-aniline.
$^1$H NMR(300 MHz, CDCl$_3$) δ 8.47 (s, 1H), 6.87-6.72(m, 3H), 6.23(s, 1H), 5.91(s, 2H), 4.66(d, J=6.0 Hz, 2H), 4.42(t, J=6.0 Hz, 2H), 2.85(t, J=6.0 Hz, 2H), 2.38(s, 3H).

Example 43

Synthesis of 4,6-dimethyl-2-phenyl-nicotinonitrile 752 mg (100%) of 4,6-dimethyl-2-phenyl-nicotinonitrile was obtained in yellow oil using the method same as in Example 30 except that 600 mg of 2-chloro-4,6-dimethyl-nicotinonitrile was used instead of 8-chloro-6-methyl-3,4-dihydro-pyrano[3,4-c]pyridine-1-on while phenyl boronic acid was used instead of 4-fluorophenyl boronic acid.
$^1$H NMR(300 MHz, CDCl$_3$) δ 7.87-7.83(m, 2H), 7.50-7.48 (m, 3H), 7.10(s, 1H), 2.63(s, 3H), 2.58(s, 3H).

Example 44

Synthesis of (3-cyano-6methyl-2-phenyl-pyridine-4-yl)-acetic acid methyl ester 705 mg (90%) of (3-cyano-6-methyl-2-phenyl-pyridine-4-yl)-acetic acid methyl ester was obtained in yellow solid using the method same as in Example 1 except that 618 mg of 4,6-dimethyl-2-phenyl-nicotinonitrile was used instead of 4-methyl-nicotinonitrile.
$^1$H NMR(300 MHz, CDCl$_3$) δ 7.88-7.85(m, 2H), 7.51-7.49 (m, 3H), 7.20(s, 1H), 3.93(s, 2H), 3.78(s, 3H), 2.67 (s, 3H).

Example 45

Synthesis of 4-(2-hydroxy-ethyl)-6-methyl-2-phenyl-nicotinonitrile 542 mg (100%) of 4-(2-hydroxy-ethyl)-6-methyl-2-phenyl-nicotinonitrile was obtained in colorless oil using the method same as in Example 2 except that 606 mg of (3-cyano-6-methyl-2-phenyl-pyridine-4-yl)-acetic acid methyl ester was used instead of (3-cyano-pyridine-4-yl)-acetic acid methyl ester.
$^1$H NMR(300 MHz, CDCl$_3$) δ 7.85-7.82(m, 2H), 7.50-7.48 (m, 3H), 7.18(s, 1H), 3.95(t, J=6.3 Hz, 2H), 3.09(t, J=6.3 Hz, 2H), 2.64(s, 3H).

Example 46

Synthesis of 6-methyl-8-phenyl-3,4-dihydro-pyrano[3,4-c]pyridine-1-on 380 mg (83%) of 6-methyl-8-phenyl-3,4dihydro-pyrano[3,4-c]pyridine-1-on was obtained in white solid using the method same as in Example 3 except that 405 mg of 4-(2-hydroxy-ethyl)-6-methyl-2-phenyl-nicotinonitrile was used instead of 4-(2-hydroxy-ethyl)-nicotinonitrile.
$^1$H NMR(300 MHz, CDCl$_3$) δ 7.54-7.52(m, 2H), 7.42-7.40 (m, 3H), 7.04(s, 1H), 4.55(t, J=6.0 Hz, 2H), 3.03(J=6.0 Hz, 2H), 2.63(s, 3H).

Example 47

Synthesis of 4,6-dimethyl-2-phenoxy-nicotinonitrile 4,6-dimethyl-2-chloro-nicotinonitrile (600 mg, 3.60 mmol) was dissolved in 30 mL of anhydrous THF and then added with sodium phenoxide trihydrate (3.06 g, 18.00 mmol) and stirred at 80° C. overnight. The mixture was extracted with methylene chloride, dried with anhydrous sodium sulfate, filtered and then concentrated under reduced pressure. A silica gel column chromatography (10% EtOAc/ Hexane) was performed on the resulting residue and 730 mg (90%) of 4,6-dimethyl-2-phenoxy-nicotinonitrile was obtained in white solid.

$^1$H NMR(300 MHz, CDCl$_3$) δ 7.39-7.36(m, 2H), 7.22-7.15 (m, 3H), 6.80(s, 1H), 2.52(s, 3H), 2.35(s, 3H).

Example 48

Synthesis of (3-cyano-6-methyl-2-phenoxy-pyridine-4-yl)-acetic aicd methyl ester 580 mg (83%) of (3-cyano-6-methyl-2-phenoxy-pyridine-4-yl)-acetic aicd methyl ester was obtained in yellow solid using the method same as in Example 1 except that 556 mg of 4,6-dimethyl-2-phenoxy-nicotinonitrile was used instead of 4-methyl-nicotinonitrile.

$^1$H NMR(300 MHz, CDCl$_3$) δ 7.43-7.37(m, 2H), 7.25-7.16 (m, 3H), 6.90(s, 1H), 3.85(s, 2H), 3.78(s, 3H), 2.38(s, 3H).

Example 49

Synthesis of 4-(2-hydroxy-ethyl)-6-methyl-2-phenoxy-nicotinonitrile 380 mg (90%) of 4-(2-hydroxy-ethyl)-6-methyl-2-phenoxy-nicotinonitrile was obtained in colorless oil using the method same as in Example 2 except that 467 mg of (3-cyano-6-methyl-2-phenoxy-pyridine-4-yl)-acetic aicd methyl ester was used instead of (3-cyano-pyridine-4-yl)-acetic aicd methyl ester.

$^1$H NMR(300 MHz, CDCl$_3$) δ 7.42-7.37(m, 2H), 7.25-7.15 (m, 3H), 6.89(s, 1H), 3.98(t, J=6.3 Hz, 2H), 3.06(t, J=6.3 Hz, 2H), 2.37 (s, 3H).

Example 50

Synthesis of 6-methyl-8-phenoxy-3,4-dihydro-pyrano[3,4-c]pyridine-1-on 280 mg (86%) of 6-methyl-8-phenoxy-3,4-dihydro-pyrano[3,4-c]pyridine-1-on was obtained in white solid using the method same as in Example 3 except that 326 mg of 4-(2-hydroxy-ethyl)-6-methyl-2-phenoxy-nicotinonitrile was used instead of 4-(2-hydroxy-ethyl)-nicotinonitrile.

$^1$H NMR(300 MHz, CDCl$_3$) δ 7.38-7.33(m, 2H), 7.20-7.14 (m, 3H), 6.74(s, 1H), 4.47 (t, J=6.0 Hz, 2H), 2.98(t, J=6.0 Hz, 2H), 2.33(s, 3H).

Example 51

Synthesis of 8-benzylamino-6-methyl-3,4-dihydro-pyrano[3,4-c]pyridine-1-on 313 mg (51%) of 8-benzylamino-6-methyl-3,4-dihydro-pyrano[3,4-c]pyridine-1-on was obtained in white solid using the method same as in Example 32 except that 460 mg of 8-chloro-6-methyl-3,4-dihydro-pyrano[3,4-c]pyridine-1-on was added with benzylamine instead of piperidine.

$^1$H NMR(300 MHz, CDCl$_3$) δ 2.38(s, 3H), 2.87 (t, 2H, J=6.0 Hz), 4.44(t, 2H, J=6.0 Hz), 4.78(d, 2H, J=5.7 Hz), 6.24(s, 1H), 7.21-7.39(m, 5H), 8.55(brs, 1H).

Example 52

Synthesis of 8-(4-methoxy-benzylamino)-6-methyl-3,4-dihydro-pyrano[3,4c]pyridine-1-on 2.97 g (98%) of 8-(4-methoxy-benzylamino)-6-methyl-3,4-dihydro-pyrano[3,4c]pyridine-1-on was obtained in white solid using the method same as in Example 32 except that 2.0 g of 8-chloro-6-methyl-3,4-dihydro-pyrano[3,4-c]pyridine-1-on was added with 4-methoxy-benzylamine instead of piperidine.

$^1$H NMR(300 MHz, CDCl$_3$) δ 2.39(s, 3H), 2.86(t, 2H, J=6.0 Hz), 3.79(s, 3H), 4.43(t, 2H, J=6.0 Hz), 4.69(d, 2H, J=5.7 Hz), 6.23(s, 1H), 6.83-6.88(m, 2H), 7.28-7.33(m, 2H), 8.48(brs, 1H).

Example 53

Synthesis of 8-amino-6-methyl-3,4-dihydro-pyrano[3,4-c]pyridine-1-on 8-(4-methoxy-benzylamino)-6-methyl-3,4-dihydro-prano[3,4c]pyridine-1-on (2.7 g, 9.05 mmol) was dissolved in 30 mL of anhydrous methylene chloride, and then dropwisely added with anisol(1.97 mL, 18.10 mmol) and trifluoro acetic acid(30 mL) in this order and then heated to reflux for about 15 hours under the nitrogen atmosphere. The mixture was concentrated under reduced pressure, added with 50 mL of distilled water and neutralized by adding a saturated solution of sodium carbonate and then extracted twice with 150 mL of methylene chloride. The resulting organic layer was dried with anhydrous sodium sulfate, and filtered. A silica gel column chromatography (5% MeOH/MC) was performed on the resulting residue and 1.53 g (95%) of 8-amino-6-methyl-3,4-dihydro-pyrano[3,4-c]pyridine-1-on was obtained in white solid.

$^1$H NMR(300 MHz, DMSO-d$_6$) δ 2.28(s, 3H), 2.87 (t, 2H, J=6.0 Hz), 4.39(t, 2H, J=6.0 Hz), 6.39(s, 1H), 7.26(brs, 2H).

Example 54

Synthesis of N-(1-oxo-6-methyl-3,4-dihydro-pyrano[3,4-c]pyridine-8-yl)-acetamide 8-amino-6-methyl-3,4-dihydro-pyrano[3,4-c]pyridine-1-on (200 g, 1.122 mmol) was dissolved in 6 mL of anhydrous acetonitrile, and then dropwisely added with triethylamine (0.63 mL, 4.490 mmol) and actic anhydride (0.42 mL, 4.490 mmol) in this order and then heated to reflux for about 20 hours under the nitrogen atmosphere. The mixture was concentrated under reduced pressure, added with 15 mL of a saturated solution of sodium carbonate and 15 mL of distilled water and then extracted twice with 40 mL of methylene chloride. The resulting organic layer was dried with anhydrous sodium sulfate, and filtered. A silica gel column chromatography (5% MeOH/MC) was performed on the resulting residue and 219 mg (89%) of N-(1-oxo-6-methyl-3,4-dihydro-pyrano[3,4-c]pyridine-8-yl)-acetamide was obtained in white solid.

$^1$H NMR(300 MHz, CDCl$_3$) δ 2.46(s, 3H), 2.54(s, 3H), 3.00(t, 2H, J=6.0 Hz), 4.52(t, 2H, J=6.0 Hz), 6.75(s, 1H), 10.89(brs, 1H).

Example 55

Synthesis of N-(1-oxo-6methyl-3,4-dihydro-pyrano[3,4-c]pyridine-8-yl)-benzamide 220 mg (69%) of N-(1-oxo-6-methyl-3,4-dihydro-pyrano[3,4-c]pyridine-8-yl)-benzamide was obtained in white solid using the method same as in Example 54 except that 200 mg of 8-amino-6-methyl-3,4-dihydro-pyrano[3,4-c]pyridine-1-on was added with benzoic anhydride instead of acetic anhydride.

$^1$H NMR(300 MHz, CDCl$_3$) δ 2.65(s, 3H), 3.05(t, 2H, J=6.0 Hz), 4.57 (t, 2H, J=6.0 Hz), 6.82(s, 1H), 7.47-7.59(m, 3H), 8.06-8.10(m, 2H), 11.98(brs, 1H).

Example 56

Synthesis of 5-iodo-2-methoxy-4,6-dimethyl-nicotinonitrile 2-methoxy-4,6-dimethyl-nicotinonitrile (1.0 g, 6.166 mmol) was disolved in 30 mL of anhydrous methylene chloride and then added with 6 mL of trifluoro acetic acid and N-iodosuccinimide (2.2 g, 9.248 mmol) in this order while stirring at 0° C. under the nitrogen atmosphere and then stirred again at room temperature for about 4 hours. The mixture was added with 60 mL of a saturated solution of sodium carbonate and 60 mL of a saturated solution of Na$_2$S$_2$O$_3$ and then extracted twice with 80 mL of methylene chloride. The resulting organic layer was dried with anhydrous sodium sulfate, and filtered. A silica gel column chromatography (5% EtOAc/Hexanes) was performed on the resulting residue and 1.67 g (94%) of 5-iodo-2-methoxy-4,6-dimethyl-nicotinonitrile was obtained in white solid.

$^1$H NMR(300 MHz, CDCl$_3$) δ 2.64(s, 3H), 2.75(s, 3H), 4.01(s, 3H).

Example 57

Synthesis of 2-methoxy-4,6-dimethyl-5-phenyl-nicotinonitrile 5-iodo-2-methoxy-4,6-dimethyl-nicotinonitrile (1.6 g, 5.554 mmol), Pd(PPh$_3$)$_4$ (642 mg, 0.555 mmol), phenyl boronic acid (1.05 g, 8.331 mmol), and anhydrous potassium carbonate (1.54 g, 11.11 mmol) were suspended in the mixed solution of 60 mL of anhydrous toluene and 3 mL of anhydrous ethanol, and then heated to reflux for about 72 hours under the nitrogen atmosphere. The mixture was filtered, added with 100 mL of a saturated solution of ammonium chloride and then extracted twice with 100 mL of methylene chloride. The resulting organic layer was dried with anhydrous sodium sulfate, and then concentrated. A silica gel column chromatography (5% EtOAc/Hexanes) was performed on the resulting residue and 1.04 g (78%) of 2-methoxy-4,6-dimethyl-5-phenyl-nicotinonitrile was obtained in pale yellow solid.

$^1$H NMR(300 MHz, CDCl$_3$) δ 2.18(s, 3H), 2.22(s, 3H), 4.06(s, 3H), 7.08-7.12(m, 2H), 7.37-7.49(m, 3H).

Example 58

Synthesis of (3-cyano-2-methoxy-6-methyl-5-phenyl-pyridine4-yl)-acetic acid methyl ester 851 mg (86%) of (3-cyano-2-methoxy-6-methyl-5-phenyl-pyridine-4-yl)-acetic acid methyl ester was obtained in pale yellow solid using the method same as in Example 1 except that 800 mg of 2-methoxy-4,6-dimethyl-nicotinonitrile was used instead of 4-methyl-nicotinonitrile.

$^1$H NMR(300 MHz, CDCl$_3$) δ 2.24(s, 3H), 3.57 (s, 2H), 3.61(s, 3H), 4.08(s, 3H), 7.07-7.11(m, 2H), 7.38-7.46(m, 3H).

Example 59

Synthesis of 4-(2-hydroxy-ethyl)-2-methoxy-6-methyl-5-phenyl-nicotinonitrile 429 mg (68%) of 4-(2-hydroxy-ethyl)-2-methoxy-6-methyl-5-phenyl-nicotinonitrile was obtained in white solid using the method same as in Example 2 except that 700 mg of (3-cyano-2-methoxy-6-methyl-5-phenyl-pyridine-4-yl)-acetic acid methyl ester was used instead of (3-cyano-pyridine-4-yl)-acetic acid methyl ester.

$^1$H NMR(300 MHz, CDCl$_3$) δ 1.36(brt, 1H, J=6.3 Hz), 2.20(s, 3H), 2.83(t, 2H, J=6.9 Hz), 3.68(q, 2H, J=6.9 Hz), 4.06(s, 3H), 7.12-7.15(m, 2H), 7.40-7.49(m, 3H).

Example 60

Synthesis of 8-hydroxy-6-methyl-5-phenyl-3,4-dihydro-pyrano[3,4-c]pyridine-1-on 442 mg (94%) of 8-hydroxy-6-methyl-5-phenyl-3,4-dihydro-pyrano[3,4-c]pyridine-1-on was obtained in white solid using the method same as in Example 3 except that 492 mg of 4-(2-hydroxy-ethyl)-2-methoxy-6-methyl-5-phenyl-nicotinonitrile was used instead of 4-(2-hydroxy-ethyl)-nicotinonitrile.

$^1$H NMR(300 MHz, DMSO-d$_6$) δ 2.02(s, 3H), 2.46(t, 2H, J=6.0 Hz), 4.19(t, 2H, J=6.0 Hz), 7.24-7.27(m, 2H), 7.37-7.49(m, 3H), 12.15(brs, 1H).

Example 61

Synthesis of 8-chloro-6-methyl-5-phenyl-3,4-dihydro-pyrano[3,4-c]pyridine-1-on 267 mg (89%) of 8-chloro-6-methyl-5-phenyl-3,4-dihydro-pyrano[3,4-c]pyridine-1-on was obtained in white solid using the method same as in Example 20 except that 280 mg of 8-hydroxy-6-methyl-5-phenyl-3,4-dihydro-pyrano[3,4-c]pyridine-1-on was used instead of 8-hydroxy-6-methyl-3,4-dihydro-pyrano[3,4-c]pyridine-1-on.

$^1$H NMR(300 MHz, CDCl$_3$) δ 2.37 (s, 3H), 2.71(t, 2H, J=5.7 Hz), 4.36(t, 2H, J=5.7 Hz), 7.13-7.17(m, 2H), 7.43-7.54(m, 3H).

Example 62

Synthesis of 6-methyl-5-phenyl-3,4-dihydro-pyrano[3,4-c]pyridine-1-on 8-chloro-6-methyl-5-phenyl-3,4-dihydro-pyrano[3,4-c]pyridine-1-on (120 mg, 0.438 mmol), palladium acetate (5.0 mg, 0.022 mmol) and sodium acetate (72 mg, 0.877 mmol) were suspended in 5 mL of anhydrous methanol and then stirred at room temperature for about 2 hours under the hydrogen atmosphere. The mixture was filtered and then concentrated under reduced pressure, added with 15 mL of a saturated solution of sodium hydrogen carbonate and then extracted twice with 20 mL of methylene chloride. The resulting organic layer was dried with anhydrous sodium sulfate, filtered and then concentrated. A silica gel column chromatography (2% MeOH/MC) was performed on the resulting residue and 101 mg (96%) of 6-methyl-5-phenyl-3,4-dihydro-pyrano[3,4-c]pyridine-1-on was obtained in white solid.

$^1$H NMR(300 MHz, CDCl$_3$) δ 2.41(s, 3H), 2.71(t, 2H, J=6.0 Hz), 4.43(t, 2H, J=6.0 Hz), 7.14-7.20(m, 2H), 7.41-7.53(m, 3H), 9.18(s, 1H).

Example 63

Synthesis of 2-hydroxy-4-methyl-6-phenyl-nicotinonitrile 1-benzoyl-acetone (5 g, 30.52 mmol) and cyanoaceamide (2.56 g, 30.52 mmol) were dissolved in 100 mL of anhydrous ethanol, added with piperidine (2.598 g, 30.52 mmol) and then stirred for 2 days at 80° C. The mixture was evaporated under reduced pressure to remove the solvent. The resulting solid was filtered and washed with methanol and water and then dried to obtain 4.75 g (73%) of 2-hydroxy-4-methyl-6-phenyl-nicotinonitrile.

$^1$H NMR(300 MHz, CDCl$_3$) δ 7.81-7.77(m, 2H), 7.54-7.51 (m, 3H), 6.73(s, 1H), 2.41(s, 3H).

Example 64

Synthesis of 2-chloro-4-methyl-6-phenyl-nicotinonitrile 2.17 (92%) of 2-chloro-4-methyl-6-phenyl-nicotinonitrile was obtained in brown solid using the method same as in Example 20 except that 2 g of 2-hydroxy-4-methyl-6-phenyl-nicotinonitrile was used instead of 8-hydroxy-6-methyl-3,4-dihydro-pyrano[3,4-c]pyridine-1-on.

$^1$H NMR(300 MHz, CDCl$_3$) δ 8.04-8.01(m, 2H), 7.62(s, 1H), 7.51-7.48(m, 3H), 2.65(s, 3H).

Example 65

Synthesis of 4-methyl-6-phenyl-nicotinonitrile 390 mg (92%) of 4-methyl-6-phenyl-nicotinonitrile was obtained using the method same as in Example 62 except that 500 mg of 2-chloromethyl-6-phenyl-nicotinonitrile was used instead of 8-chloro-6-methyl-5-phenyl-3,4-dihydro-pyrano [3,4-c]pyridine-1-on.

$^1$H NMR(300 MHz, CDCl$_3$) δ 8.85(s, 1H), 8.04-8.01(m, 2H), 7.69(s, 1H), 7.53-7.48(m, 3H), 2.62(s, 3H).

Example 66

Synthesis of (5-cyano-2-phenyl-pyridine yl)-acetic acid methyl ester 600 mg (92%) of (5-cyano-2-phenyl-pyridine-4-yl)-acetic acid methyl ester was obtained in colorless oil using the method same as in Example 1 except that 500 mg of 4-methyl-6-phenyl-nicotinonitrile was used instead of 4-methyl-nicotinonitrile.

$^1$H NMR(300 MHz, CDCl$_3$) δ 8.92(s, 1H), 8.06-8.03(m, 2H), 7.82(s, 1H), 7.52-7.50(m, 3H), 3.94(s, 2H), 3.79(s, 3H).

Example 67

Synthesis of 4-(2-hydroxy-ethyl)-6-phenyl-nicotinonitrile 400 mg (90%) of 4-(2-hydroxy-ethyl)-6-phenyl-nicotinonitrile was obtained in white solid using the method same as in Example 2 except that 500 mg of (5-cyano-2-phenyl-pyridine-4-yl)-acetic acid methyl ester was used instead of (3-cyano-pyridine-4-yl)-acetic acid methyl ester.

$^1$H NMR(300 MHz, CDCl$_3$) δ 8.87 (s, 1H), 8.05-8.02(m, 2H), 7.77 (s, 1H), 7.51-7.49(m, 3H), 3.74(t, J=6.3 Hz, 2H), 3.15(t, J=6.3 Hz, 2H).

Example 68

Synthesis of 6-phenyl-3,4-dihydro-pyrano[3,4-c]pyridine-1-on 286 mg (95%) of 6-phenyl-3,4-dihydro-pyrano[3,4-c]pyridine-1-on was obtained in white solid using the method same as in Example 3 except that 300 mg of 4-(2-hydroxy-ethyl)-6-phenyl-nicotinonitrile was used instead of 4-(2-hydroxy-ethyl)-nicotinonitrile.

$^1$H NMR(300 MHz, CDCl$_3$) δ 9.31(s, 1H), 8.07-8.04(m, 2H), 7.63(s, 1H), 7.52-7.49(m, 3H), 4.60(t, J=5.7 Hz, 2H, 3.13(t, J=5.6 Hz, 2H).

Example 69

Synthesis of 2-methoxy-4-methyl-6-phenyl-nicotinonitrile 2-chloro4-methyl-6-phenyl-nicotinonitrile (455 mg, 1.99 mmol) was dissolved in 20 mL of DME, added with 95% sodium methoxide (1.13 g, 19.90 mmol) and then stirred at room temperature for about 1 hour. The mixture was added to cool water and was adjusted to have a pH of about 6 to 7 with 10% HCl and then extracted with ethyl acetate. A silica gel column chromatography (10% EtOAc/Hexane) was performed on the resulting residue and 370 mg (83%) of 2-methoxy-4-methyl-6-phenyl-nicotinonitrile was obtained in white solid.

$^1$H NMR(300 MHz, CDCl$_3$) δ 8.06-8.03(m, 2H), 7.48-7.46 (m, 3H), 7.30(s, 1H), 4.14(s, 3H), 2.65(s, 3H).

Example 70

Synthesis of (3-cyano-2-methoxy-6-phenyl-pyridine-4-yl)-acetic acid methyl ester 770 mg (90%) of (3-cyano-2-methoxy-6-phenyl-pyridine-4-yl)-acetic acid methyl ester was obtained in colorless oil using the method same as in Example 1 except that 680 mg of 2-methoxy4-methyl-6-phenyl-nicotinonitrile was used instead of 4-methyl-nicotinonitrile.

$^1$H NMR(300 MHz, CDCl$_3$) δ 8.06-8.03(m, 2H), 7.49-7.40 (m, 3H), 7.40(s, 1H), 4.16(s, 3H), 3.89(s, 2H), 3.76(s, 3H).

Example 71

Synthesis of 4-(2-hydroxy-ethyl)-2-methoxy-6-phenyl-nicotinonitrile 414 mg (95%) of 4-(2-hydroxy-ethyl)-2-methoxy-6phenyl-nicotinonitrile was obtained in white solid using the method same as in Example 2 except that 550 mg of (3-cyano-2-methoxy-6-phenyl-pyridine-4-yl)-acetic acid methyl ester was used instead of (3-cyano-pyridine-4yl)-acetic acid methyl ester.

$^1$H NMR(300 MHz, CDCl$_3$) δ 8.06-8.03(m, 2H), 7.48-7.46 (m, 3H), 7.39(s, 1H), 4.14(s, 3H), 4.00(t, J=6.0 Hz, 2H), 3.09(t, J=6.0 Hz, 2H).

Example 72

Synthesis of 8-hydroxy-6-phenyl-3,4-dihydro-pyrano[3,4-c]pyridine-1-on 360 mg (95%) of 8-hydroxy-6-phenyl-3,4-dihydro-pyrano[3,4-c]pyridine-1-on was obtained using the method same as in Example 3 except that 400 mg of 4-(2-hydroxy-ethyl)-2-methoxy-6-phenyl-nicotinonitrile was used instead of 4-(2-hydroxy-ethyl)-nicotinonitrile.

$^1$H NMR(300 MHz, CDCl$_3$) δ 7.88-7.84(m, 2H), 7.54-7.51 (m, 3H), 7.17 (s, 1H), 4.39(t, J=6.0 Hz, 2H), 2.97 (t, J=6.0 Hz, 2H).

Example 73

Synthesis of 8-chloro-6-phenyl-3,4-dihydro-pyrano[3,4-c]pyridine-1-on 230 mg (82%) of 8-hydroxy-6-phenyl-3,4-dihydro-pyrano[3,4A]pyridine-1-on was obtained in white solid using the method same as in Example 20 except-that 300 mg of 8-hydroxy-6-phenyl-3,4-dihydro-pyrano[3,4-c]pyridine-1-on HCl salt was used instead of 8-hydroxy-6-methyl-3,4-dihydro-pyrano[3,4-c]pyridine-1-on.

$^1$H NMR(300 MHz, CDCl$_3$) δ 8.05-8.02(m, 2H), 7.56(s, 1H), 7.50-7.47(m, 3H), 4.50(t, J=6.0 Hz, 2H), 3.12(t, J=6.0 Hz, 2H).

Example 74

Synthesis of 2,4-dimethyl-6-phenyl-nicotinonitrile

Copper bromide (2.56 g, 17.49 mmol) was suspended in 20 mL of anhydrous THF, dropwisely added with magnesium bromide (3.0M ether, 11.66 mL, 34.99 mmol) at −78° C. and stirred for about 20 minutes. A 10 mL of anhydrous TNF was dropwisely added with a solution, wherein 2 chloro-6-phenyl-4-methyl-nicotinonitrile was dissolved, at the above temperature and then stirred for about 1 hour at room temperature. The mixture was added with a saturated solution of ammonium hydroxide and adjusted its pH to 10 with 1 N NaOH. Then, it was extracted with ethyl acetate, dried with anhydrous sodium sulfate, filtered and concentrated under reduced pressure. A silica gel column chromatography (5% EtOAc/Hexane) was performed on the resulting residue and 550 mg (55%) of 2,4-dimethyl-6-phenyl-nicotinonitrile was obtained in white solid.

$^1$H NMR(300 MHz, CDCl$_3$) δ 8.03-8.00(m, 2H), 7.50-7.47 (m, 3H), 2.82(s, 3H), 2.59(s, 3H).

Example 75

Synthesis of (3-cyano-2-methyl-6-phenyl-pyridine-4-yl)-acetic acid methyl ester 610 mg (95%) of (3-cyano-2-methyl-6-phenyl-pyridine-4-yl)-acetic acid methyl ester was obtained in white solid using the method same as in Example 1 except that 500 mg of 2,4-dimethyl-6-phenyl-nicotinonitrile was used instead of 4-methyl-nicotinonitrile.

$^1$H NMR(300 MHz, CDCl$_3$) δ 8.04-8.01(m, 2H), 7.61(s, 1H), 7.50-7.47(m, 3H), 3.91(s, 2H), 3.77 (s, 3H), 2.85(s, 3H).

Example 76

Synthesis of 4-(2-hydroxy-ethyl)-2-methyl-6-phenyl-nicotinonitrile 465 mg (95%) of 4-(2-hydroxy-ethyl)-2-methyl-6-phenyl-nicotinonitrile was obtained in white solid using the method same as in Example 2 except that 550 mg of (3-cyano-2-methyl-6-phenyl-pyridine-4-yl)-acetic acid methyl ester was used instead of (3-cyano-pyridine-4-yl)-acetic acid methyl ester.

$^1$H NMR(300 MHz, CDCl$_3$) δ 8.04-8.01(m, 2H), 7.60(s, 1H), 7.49-7.47(m, 3H), 3.99(t, J=6.0 Hz, 2H), 3.12(t, J=6.0 Hz, 2H), 2.83(s, 3H).

Example 77

Synthesis of 8-methyl-6-phenyl-3,4-dihydro-pyrano[3,4-c]pyridine-1-on 440 mg (99%) of 8-methyl-6-phenyl-3,4-dihydro-pyrano[3,4-c]pyridine-1-on was obtained in white solid using the method same as in Example 3 except that 444 mg of 4-(2-hydroxy-ethyl)-2-methyl-6-phenyl-nicotinonitrile was used instead of 4-(2-hydroxy-ethyl)-nicotinonitrile.

$^1$H NMR(300 MHz, CDCl$_3$) δ 8.07-8.04(m, 2H), 7.49-7.47 (m, 3H), 4.50(t, J=5.7 Hz, 2H), 3.08(t, J=5.7 Hz, 2H), 2.97 (s, 3H).

Example 78

Synthesis of 1-oxo-6phenyl-3,4-dihydro-1H-pyrano[3,4-c]pyridine-8-yl acetic ester 255 mg (84%) of 1-oxo-6-phenyl-3,4-dihydro-1H-pyrano[3,4-c]pyridine-8-yl acetic ester was obtained in white solid using the method same as in Example 21 except that 300 mg of 8-hydroxy-6-phenyl-3,4-dihydro-pyrano[3,4-c]pyridine-1-on was used instead of 8-hydroxy-6-methyl-3,4-dihydro-pyrano[3,4-c]pyridine-1-on.

$^1$H NMR(300 MHz, CDCl$_3$) δ 8.03-8.00(m, 2H), 7.57 (s, 1H), 7.49-7.46(m, 3H), 4.53(t, J=6.0 Hz, 2H), 3.12(t, J=6.0 Hz, 2H), 2.43(s, 3H).

Example 79

Synthesis of 8-methoxy-6-phenyl-3,4-dihydro-pyrano[3,4-c]pyridine-1-on 8-hydroxy-6-phenyl-3,4-dihydro-pyrano[3,4-c]pyridine-1-on HCl salt (300 mg, 1.080 mmol), iodo methane (3.68 g, 25.92 mmol), silver oxide (936 mg, 4.04 mmol) and calcium sulfate (239.7 mg, 1.76 mmol) were dissolved in 20 mL of anhydrous and then stirred overnight at room temperature. The mixture was evaporated under reduced pressure. A silica gel column chromatography (30% EtOAc/Hexane) was performed on the resulting residue and 193 mg (70%) of 8-methoxy-6-phenyl-3,4-dihydro-pyrano[3,4-c]pyridine-1-on was obtained in white solid.

$^1$H NMR(300 MHz, CDCl$_3$) δ 8.05-8.02(m, 2H), 7.45-7.43 (m, 3H), 7.21(s, 1H), 4.44(t, J=6.0 Hz, 2H), 4.15(s, 3H), 3.01(t, J=6.0 Hz, 2H).

Example 80

Synthesis of 8-methylamino-6-phenyl-3,4-dihydro-pyrano[3,4-c]pyridine-1-on 101 mg (45%) of 8-methylamino-6-phenyl-3,4-dihydro-pyrano[3,4-c]pyridine-1-on was obtained in white solid using the method same as in Example 35 except that 230 mg of 8-chloro-6-phenyl-3,4-dihydro-pyrano[3,4-c]pyridine-1-on was added with methyl amine instead of 4-fluoro-aniline.

$^1$H NMR(300 MHz, CDCl$_3$) δ 8.17 (s, 1H), 8.11-8.06(m, 2H), 7.51-7.44(m, 3H), 6.83(s, 1H), 4.50(t, J=6.0 Hz, 2H), 3.18(d, J=4.8 Hz, 3H), 2.98(t, J=6.0 Hz, 2H).

Example 81

Synthesis of 8-dimethylamino-6-phenyl-3,4-dihydro-pyrano[3,4-c]pyridine-1-on 140 mg (99%) of 8-dimethylamino-6-phenyl-3,4-dihydro-pyrano[3,4-c]pyridine-1-on was obtained in white solid using the method same as in Example 35 except that 137 mg of 8-chloro-6-phenyl-3,4-dihydro-pyrano[3,4-c]pyridine-1-on was added with dimethyl amine instead of 4-fluoro-aniline.

$^1$H NMR(300 MHz, CDCl$_3$) δ 8.07-8.05(m, 2H), 7.46-7.44 (m, 3H), 6.95(s, 1H), 4.47 (t, J=6.0 Hz, 2H), 3.18(s, 6H), 3.01(t, J=6.0 Hz, 2H).

Example 82

Synthesis of 6-phenyl-8-piperidine-1-yl-3,4-dihydro-pyrano[3,4-c]pyridine-1-on 127 mg (98%) of 6-phenyl-8-piperidine-1-yl-3,4-dihydro-pyrano[3,4-c]pyridine-1-on was obtained in white solid using the method same as in Example 35 except that 110 mg of 8-chloro-6-phenyl-3,4-dihydro-pyrano[3,4-c]pyridine-1-on was added with piperidine instead of 4-fluoro-aniline.

$^1$H NMR(300 MHz, CDCl$_3$) δ 8.05-8.01(m, 2H), 7.45-7.42 (m, 3H), 6.93(s, 1H), 4.45(t, J=6.0 Hz, 2H), 3.58(m, 4), 2.98(t, J=6.0 Hz, 2H), 1.70(s, 6H).

Example 83

Synthesis of 8-morpholine-4-yl-6-phenyl-3,4-dihydro-pyrano[3,4-c]pyridine-1-on 128 mg (98%) of 8-morpholine-4-yl-6-phneyl-3,4-dihydro-pyrano[3,4-c]pyridine-1-on was obtained in white solid using the method same as in Example 35 except that 110 mg of 8-chloro-6-phenyl-3,4-dihydro-pyrano[3,4-c]pyridine-1-on was added with morpholine instead of 4-fluoro-aniline.

$^1$H NMR(300 MHz, CDCl$_3$) δ 8.03-8.00(m, 2H), 7.46-7.43 (m, 3H), 7.02(s, 1H), 4.45(t, J=6.0 Hz, 2H), 3.85(t, J=5.1 Hz, 4H), 3.63(t, J=5.1 Hz, 4H), 2.99(t, J=6.0 Hz, 2H).

Example 84

Synthesis of 6-phenyl-8-pyrolidine-1-yl-3,4-dihydro-pyrano[3,4-c]pyridine-1-on 120 mg (97%) of 6-phenyl-8-pyrolidine-1-yl-3,4-dihydro-pyrano[3,4-c]pyridine-1-on was obtained in white solid using the method same as in Example 35 except that 110 mg of 8-chloro-6-phenyl-3,4-dihydro-pyrano[3,4c]pyridine-1-on was added with pyrolidine instead of 4-fluoro-aniline.

$^1$H NMR(300 MHz, CDCl$_3$) δ 8.07-8.04(m, 2H),7.45-7.43 (m, 3H), 6.93(s, 1H), 4.46(t, J=6.0 Hz, 2H), 3.57 (s, 4H), 3.00(t, J=6.0 Hz, 2H), 1.99-1.95(m, 4H).

Example 85

Synthesis of 8-(4-fluoro-phenylamino)-6-phenyl-3,4-dihydro-pyrano[3,4-c]pyridine-1-on 134 mg (95%) of 8-(4-fluoro-phenylamino)-6-phenyl-3,4-dihydro-pyrano[3,4-c]pyridine-1-on was obtained in pale yellow solid using the method same as in Example 35 except that 110 mg of 8-chloro-6-phenyl-3,4-dihydro-pyrano[3,4-c]pyridine-1-on was used instead of 8-chloro-6-methyl-3,4-dihydro-pyrano[3,4-c]pyridine-1-on.

$^1$H NMR(300 MHz, CDCl$_3$) δ 10.42(s, 1H), 8.04-8.01(m, 2H), 7.77-7.72(m, 2H), 7.49-7.46(m, 3H), 7.10-7.03(m, 3H), 4.57 (t, J=6.0 Hz, 2H), 3.07 (t, J=6.0 Hz, 2H).

Example 86

Synthesis of 8-(4-methoxy-benzylamino)-6-phenyl-3,4-dihydro-pyrano[3,4-c]pyridine-1-on 2.03 g (98%) of 8-(4-methoxy-benzylamino)-6-phenyl-3,4-dihydro-pyrano[3,4-c]pyridine-1-on was obtained in pale yellow solid using the method same as in Example 35 except that 1.5 g of 8-chloro-6-phenyl-3,4-dihydro-pyrano[3,4-c]pyridine-1-on was added with 4-methoxy-benzylamine instead of 4-fluoro-aniline.

$^1$H NMR(300 MHz, CDCl$_3$) δ 2.98(t, 2H, J=6.0 Hz), 3.79 (s, 3H), 4.49(t, 2H, J=6.0 Hz), 4.82(d, 2H, J=5.4 Hz), 6.84-6.89(m, 3H), 7.32-7.37(m, 2H), 7.42-7.47(m, 3H), 8.02-8.05 (m, 2H), 8.57(brs, 1H).

Example 87

Synthesis of 8-amino-6-phenyl-3,4-dihydro-pyrano[3,4-c]pyridine-1-on 1.30 g (96%) of 8-amino-6-phenyl-3,4-dihydro-pyrano[3,4-c]pyridine-1-on was obtained in white solid using the method same as in Example 53 except that 2.03 g of 8-(4methoxy-benzylamino)-6-phenyl-3,4-dihydro-pyrano[3,4-c]pyridine-1-on was used instead of 8-(4methoxy-benzylamino)-6-methyl-3,4-dihydro-pyrano[3,4-c]pyridine-1-on.

$^1$H NMR(300 MHz, CDCl$_3$) δ 3.01(t, 2H, J=6.0 Hz), 4.52 (t, 2H, J=6.0 Hz), 6.91(s, 1H), 7.44-7.50(m, 3H), 7.95-7.99 (m, 2H).

Example 88

Synthesis of N-(1-oxo-6-phenyl-3,4-dihydro-pyrano[3,4-c]pyridine-8-yl)-acetamide 212 mg (90%) of N-(1-oxo-6-phenyl-3,4-dihydro-pyrano[3,4-c]pyridine-8-yl)-acetamide was obtained in white solid using the method same as in Example 54 except that 200 mg of 8-amino-6-phenyl-3,4-dihydro-pyrano[3,4-c]pyridine-1-on was used instead of 8-amino-6-methyl-3,4-dihydro-pyrano[3,4-c]pyridine-1-on.

$^1$H NMR(300 MHz, CDCl$_3$) δ 2.60(s, 3H), 3.12(t, 2H, J=6.3 Hz), 4.57 (t, 2H, J=6.3 Hz), 7.33(s, 1H), 7.47-7.52(m, 3H), 8.05-8.10(m, 2H), 10.99(brs, 1H).

Example 89

Synthesis of N-(1-oxo-phenyl-3,4-dihydro-pyrano[3,4-c]pyridine-8-yl)-benzamide 260 mg (83%) of N-(1-oxo-6-phenyl-3,4-dihydro-pyrano[3,4-c]pyridine-8-yl)-benzamide was obtained in white solid using the method same as in Example 55 except that 220 mg of 8-amino-6-phenyl-3,4-dihydro-pyrano[3,4-c]pyridine-1-on was used instead of 8-amino-6-methyl-3,4-dihydro-pyrano[3,4-c]pyridine-1-on.

$^1$H NMR(300 MHz, CDCl$_3$) δ 3.16(t, 2H, J=6.0 Hz), 4.62 (t, 2H, J=6.0 Hz), 7.41(s, 1H), 7.47-7.61(m, 6H), 8.08-8.12 (m, 2H), 8.21-8.25(m, 2H), 12.02(brs, 1H).

Example 90

Synthesis of 2,6-dichloro-4-methyl-nicotinonitrile 2,6-dihydroxy-4-methyl-nicotinonitrile (6 g, 39.96 mmol) and benzyltriethyl ammonium chloride (18.20 g, 79.92 mmol) were added with phosphorous oxychloride (30.63 g, 199.8 mmol) and stirred overnight at 120° C. The mixture was slowly added to cool water and the resulting solid was filtered to obtain 6.64 g (89%) of 2,6-dichloro-4-methyl-nicotinonitrile.

$^1$H NMR(300 MHz, CDCl$_3$) δ 7.29(s, 1H), 2.59(s, 3H).

Example 91

Synthesis of 2-chloro-6-methoxy-4-methyl-nicotinonitrile 2,6-dichloro-4-methyl-nicotinonitrile (3.70 g, 19.83 mmol) was dissolved in 30 mL of methanol, added with 4.28 mL of methanol containing 25% sodium methoxide and then stirred for about 3 hours at room temperature. The mixture was added to cool water, adjusted to have a pH of about 6 to 7 with 10% HCl and extracted using methylene chloride. The extract was dried with anhydrous sodium sulfate, filtered and evaporated under reduced pressure. A silica gel column chromatography (10% EtOAc/Hexane) was performed to obtain 1.8 g (50%) of 2-chloro-6-methoxy-4-methyl-nicotinonitrile in pale yellow solid.

$^1$H NMR(300 MHz, CDCl$_3$) δ 7.42(s, 1H), 4.29(s, 3H), 2.60(s, 3H).

Example 92

Synthesis of 6-methoxy-2,4-dimethyl-nicotinonitrile 266 mg (60%) of 6-methoxy-2,4-dimethyl-nicotinonitrile was obtained in white solid using the method same as in Example 74 except that 500 mg of 2-chloro-6-methoxy4-methyl-nicotinonitrile was used instead of 2-chloro-6-phenyl-4-methyl-nicotinonitrile.

$^1$H NMR(300 MHz, CDCl$_3$) δ 6.47 (s, 1H), 3.94(s, 3H), 2.64(s, 3H), 2.43(s, 3H).

Example 93

Synthesis of (3-cyano-6-methoxy-2-methyl-pyridine-4-yl)-acetic acid methyl ester 1.0 g (93%) of (3-cyano-6-methoxy-2-methyl-pyridine-fyl)-acetic acid methyl ester was obtained in white solid using the method same as in Example 1 except that 786 mg of 6-methoxy-2,4-dimethyl-nicotinonitrile was used instead of 4-methyl-nicotinonitrile.

$^1$H NMR(300 MHz, CDCl$_3$) δ 6.58(s, 1H), 3.96(s, 3H), 3.76(s, 2H), 3.75(s, 3H), 2.67 (s, 3H).

Example 94

Synthesis of 4-(2-hydroxy-ethyl)-6-methoxy-2-methyl-nicotnonitrile 862 mg (98%) of 4-(2-hydroxy-ethyl)-6-methoxy-2-methyl-nicotnonitrile was obtained in colorless oil using the method same as in Example 2 except that 1 g of (3-cyano-6-methoxy-2-methyl-pyridine-4-yl)-acetic acid methyl ester was used instead of (3-cyano-pyridine-4-yl)-acetic acid methyl ester.

$^1$H NMR(300 MHz, CDCl$_3$) δ 6.58(s, 1H), 3.94(s, 3H), 3.97 (t, J=6.0 Hz, 2H), 3.09(t, J=6.0 Hz, 2H), 2.64(s, 3H).

Example 95

Synthesis of 6-hydroxy-8-methyl-3,4-dihydro-pyrano[3,4-c]pyridine-1-on HCl salt 1.17 g (100%) of 6-hydroxy-8-methyl-3,4-dihydro-pyrano[3,4-c]pyridine-1-on HCl salt was obtained using the method same as in Example 3 except that 860 mg of 4-(2-hydroxy-ethyl)-6-methoxy-2-methyl-nicotnonitrile was used instead of 4(2-hydroxy-ethyl)-nicotinonitrile.

$^1$H NMR(300 MHz, CDCl$_3$) δ 7.14(s, 1H), 4.50(t, J=6.0 Hz, 2H), 3.00(t, J=6.0 Hz, 2H), 2.87 (s, 3H).

Example 96

Synthesis of 6-chloro-8-methyl-3,4-dihydro-pyrano[3,4-c]pyridine-1-on 196 mg (89%) of 6-chloro-8-methyl-3,4-dihydro-pyrano[3,4-c]pyridine-1-on was obtained using the method same as in Example 20 except that 200 mg of 6-hydroxy-8-methyl-3,4-dihydro-pyrano[3,4-c]pyridine-1-on was used instead of 8-hydroxy-6-methyl-3,4dihydro-pyrano[3,4-c]pyridine-1-on.

$^1$H NMR(300 MHz, CDCl$_3$) δ 7.12(s, 1H), 4.46(t, J=6.0 Hz, 2H), 3.01(t, J=6.0 Hz, 2H), 2.86(s, 3H).

Example 97

Synthesis of 8-methyl-6-(thiophene-2-yl)-3,4-dihydro-pyrano[3,4-c]pyridine-1-on 2-(tributylstannyl)thiophene (940 mg, 2.52 mmol) was dropwisely added to a toluene solution of 6-chloro-8-methyl-3,4-dihydro-pyrano[3,4-c]pyridine-1-on (250 mg, 1.26 mmol) and Pd(PPh$_3$)$_4$ (146 mg, 0.13 mmol), and then stirred overnight at 100° C. The solution was cooled down to room temperature, added with 15 mL of 0.4M KF solution and then extracted with methylene chloride. The resulting organic layer was dried with anhydrous sodium sulfate, filtered and then concentrated under reduced pressure. A silica gel column chromatography (33% EtOAC/Hexanes) was performed on the resulting residue and obtained 298 mg (96%) of 8-methyl-6-(thiophene-2-yl)-3,4-dihydro-pyrano[3,4-c]pyridine-1-on in yellow solid.

¹H NMR(300 MHz, CDCl₃) δ 7.6 8(dd, J=1.1 Hz, 3.75 Hz, 1H), 7.49(dd, J=1.1 Hz, 3.75, 1H), 7.36(s, 1H), 7.14(dd, J=3.9 Hz, 5.1 Hz, 1H), 4.48(t, J=6.0 Hz, 2H), 3.04(t, J=5.9 Hz, 2H), 2.91(s, 3H).

Example 98

Synthesis of 6-(furan-2-yl)-8-methyl-3,4-dihydro-pyrano[3,4-c]pyridine-1-on 251 mg (87%) of 6-(furan-2-yl)-8-methyl-3,4-dihydro-pyrano[3,4-c]pyridine-1-on was obtained in pink solid using the method same as in Example 97 except that 6-chloro-8-methyl-3,4-dihydro-pyrano[3,4-c]pyridine-1-on (250 mg, 1.26 mmol) was added with 2-(tributylstannyl)furan instead of 2-(tributylstannyl)thiophene.

¹H NMR(300 MHz, CDCl₃) δ 7.58(d, J=0.9 Hz, 1H), 7.42 (s, 1H), 7.23(d, J=3.3 Hz, 1H), 6.57 (q, J=1.8 Hz, 1H), 4.48(t, J=6.0 Hz, 2H), 3.05(t, J=5.9 Hz, 2H), 2.92(s, 1H).

Example 99

Synthesis of 6-(benzo[d][1,3]dioxol-6-yl)-8methyl-3,4-dihydro-pyrano[3,4c]pyridine-1-on An orange-colored THF/NMP(6 mL/0.6 mL) solution of 6-chloro-8-methyl-3,4-dihydro-pyrano[3,4-c]pyridine-1-on (250 mg, 1.26 mmol) and Fe (acac)₃ (22 mg, 0.06 mmol) was slowly added with 3,4-(methylenedeoxy)phenyl magnesium bromide (1M solution in toluene/THF=1/1, 2.5 mL, 2.5 mmol) solution and then stirred at room temperature for about 10 minutes. The above mixture was dropwisely added with 50 mL of a saturated ammonium chloride solution, added with 20 mL of water and then extracted with 100 mL of ethylacetate 100 mL. The resulting organic layer was dried with anhydrous sodium sulfate, filtered and then concentrated under reduced pressure. A silica gel column chromatography (33% EtOAC/Hexanes) was performed on the resulting residue and obtained 214 mg (59%) of 6-(benzo[d][1,3]dioxol-6-yl)-8-methyl-3,4-dihydro-pyrano[3,4-c]pyridine-1-and it was recrystallized with MC/Ether to obtain 116 mg of the same in white powder.

¹H NMR(300 MHz, CDCl₃) δ 7.61(s, 1H), 7.58(d, J=1.8 Hz, 1H), 6.91(d, J=8.7 Hz, 1H), 6.04(s, 2H), 4.49(t, J=5.7 Hz, 2H), 3.36(t. J=5.7 Hz, 2H), 2.94(s, 3H).

Example 100

Synthesis of 6-(4-(dimethylamino)phenyl)-8-methyl-3,4-dihydro-pyrano[3,4-c]pyridine-1-on 160 mg (45%) of 6-(4-(dimethylamino)phenyl)-8-methyl-3,4-dihydro-pyrano[3,4-c]pyridine-1-on was obtained in pale yellow solid using the method same as in Example 99 except that 6chloro-8-methyl-3,4-dihydro-pyrano[3,4-c]pyridine-1-on (250 mg, 1.26 mmol) was added with 4-(N,N-dimethyl) aniline magnesium bromide instead of 3,4-(methylenedeoxy) phenyl magnesium bromide.

¹H NMR(300 MHz, CDCl₃) δ 8.00-8.03(m, 2H), 7.34(s, 1H), 6.76-6.79(m, 2H), 4.47 (t, J=5.7 Hz, 2H), 3.01-3.05(m, 8H), 2.93(s, 3H).

Example 101

Synthesis of 2-methoxymethyl-6-propyl-nicotinonitrile

A transparent red-colored THF/NMP(50 mL/5 mL) solution of 6-chloro-2-methoxy-4-methyl-nicotinonitrile (2.00 g, 11.0 mmol) and Fe (acac)₃ (387 mg, 1.1 mmol) was slowly added with 11 mL of n-propylmagnesium bromide (2M solution in diethyl ether) and then stirred for about 20 minutes. The mixture was then added with 10 mL of 1M HCl solution 10 mL and diluted with 300 mL of ethylacetate. The resulting organic layer was washed with water and a saturated solution of sodium chloride, dried with anhydrous sodium sulfate and then filtered. A silica gel column chromatography (10% EtOAc/Hexane) was performed on the residue obtained by concentrating the above filtrate under reduced pressure and obtained 2.23 g (88%) of 2-methoxy4-methyl-6-propyl-nicotinonitrile in colorless oil.

¹H NMR(300 MHz, CDCl₃) δ 6.77 (s, 1H), 4.01(s, 3H), 2.77 (t, J=7.5 Hz, 2H), 2.46(s, 3H), 1.80-1.73(m, 2H), 0.99(t, J=7.5 Hz, 3H).

Example 102

Synthesis of (3-cyano-2-methoxy-6-propyl-pyridine-4-yl)-acetic acid methyl ester 2.2 g (89%) of (3-cyano-2-methoxy-6-propyl-pyridine-4-yl)-acetic acid methyl ester was obtained in colorless oil using the method same as in Example 1 except that 1.9 g of 2-methoxy-4-methyl-6-propyl-nicotinonitrile was used instead of 4-methyl-nicotinonitrile ¹H NMR(300 MHz, CDCl₃) δ 6.79(s, 1H), 4.03(s, 3H), 3.79(s, 2H), 3.74(s, 3H), 2.69(t, J=7.5 Hz, 2H), 1.77-1.72(m, 2H), 0.96(t, J=7.5 Hz, 3H).

Example 103

Synthesis of 4-(2-hydroxy-ethyl)-2-methoxy-6-propyl-nicotinonitrile 1.8 g (94%) of 4-(2-hydroxy-ethyl)-2-methoxypropyl-nicotinonitrile was obtained in colorless oil using the method same as in Example 2 except that 2.15 g of (3-cyano-2-methoxy-6-propyl-pyridine-4-yl)-acetic acid methyl ester was used instead of (5-cyano-pyridine-4-yl)-acetic acid methyl ester.

¹H NMR(300 MHz, CDCl₃) δ 6.75(s, 1H), 4.02(s, 3H), 3.95(t, J=6.6 Hz, 2H), 3.00(t, J=6.6 Hz, 2H), 2.68(t, J=7.2 Hz, 2H), 1.78-1.71(m, 2H), 0.96(t, J=7.2 Hz, 2H).

Example 104

Synthesis of 8-hydroxy-6-propyl-3,4-dihydro-pyrano [3,4-c]pyridine-1-on HCl salt and 6-hydroxy-8-propyl-3,4-dihydro-pyrano[3,4-c]pyridine-1-on HCl salt 8-hydroxy-6-propyl-3,4-dihydro-pyrano[3,4-c]pyridine-1-on HCl salt and 6-hydroxy-1-on HCl salt and 6-hydroxy-8-propyl-3,4-dihydro-pyrano[3,4-c]pyridine-1-on HCl 1.8 g (90%) and 1.7 g (85%), respectively, in white solid using the method same as in Example 3 except that 1.8 g of 4-(2-hydroxy-ethyl)-2-methoxy-6-propyl-nicotinonitrile and 4-(2-hydroxy-ethyl)-6-methoxy-2-propyl-nicotinonitrile were respectively used instead of 4-(2-hydroxy-ethyl)-nicotinonitrile.

¹H NMR(300 MHz, CDCl₃) δ 7.01(s, 1H), 4.48(t, J=6.0 Hz, 2H), 3.03(t, J=6.0 Hz, 2H), 2.77 (t, J=7.2 Hz, 2H), 1.81-1.76(m, 2H), 0.96(t, J=7.2 Hz, 3H).

¹H NMR(300 MHz, CDCl₃) δ 7.08(s, 1H), 4.46(t, J=6.0 Hz, 2H), 3.20-3.14(m, 2H), 3.01(t, J=6.0 Hz, 2H), 1.77-1.69 (m, 2H), 0.99(t, J=7.5 Hz, 3H).

Example 105

Synthesis of 8-chloro-6-propyl-3,4-dihydro-pyrano[3,-c]pyridine-1-on and 8-propyl-6-chloro-3,4-dihydro-pyrano[3,4-c]pyridine-1-on 8-chloro-6-propyl-3,4-dihydro-pyrano[3,4-c]pyridine-1-on and 8-propyl-6 chloro-3,4-dihydro-pyrano[3,4-c]pyridine-1-on were obtained 450 mg (97%) and 400 mg (86%), respectively, in white solid using the method same as in Example 3 except that 500 mg of 8-hydroxy-6-propyl-3,4-dihydro-pyrano[3,4-c]pyridine-1-on HCl salt and 6-hydroxy-8-propyl-3,4-dihydro-pyrano[3,4-c]pyridine-1-on HCl salt were respectively used instead of 8-hydroxy-6-methyl-3,4-dihydro-pyrano[3,4-c]pyridine-1-on.

$^1$H NMR(300 MHz, CDCl$_3$) δ 7.00(s, 1H), 4.48(t, J=6.0 Hz, 2H), 3.04(t, J=6, 2H) 2.77 (t, J=7.2 Hz, 2H), 1.80-1.73(m, 2H), 0.98(t, J=7.2 Hz, 3H).

$^1$H NMR(300 MHz, CDCl$_3$) δ 7.09(s, 1H), 4.44(t, J=6.0 Hz, 2H), 3.17 (t, J=7.2 Hz, 2H), 3.00(t, J=6.0 Hz, 2H), 1.77-1.72(m, 2H), 0.99(t, J=7.2 Hz, 3H).

Example 106

Synthesis of 8-morpholine-4-yl-6-propyl-3,4-dihydro-pyrano[3,4-c]pyridine-1-on 367 mg (90%) of 8-morpholine-4-yl-6-propyl-3,4-dihydro-pyrano[3,4-c]pyridine-1-on was obtained in white solid using the method same as in Example 35 except that 300 mg of 8-chloro-6-propyl-3,4-dihydro-pyrano[3,4-c]pyridine-1-on was added with morpholine instead of 4-fluoro-aniline.

$^1$H NMR(300 MHz, CDCl$_3$) δ 7.02(s, 1H), 4.49(t, J=6.0 Hz, 2H), 3.88(t, J=5.4 Hz, 4H), 3.64(t, J=5.4 Hz, 4H), 3.05(t, J=6.2 Hz, 2H), 2.77 (t, J=7.2 Hz, 2H), 1.80-1,73(m, 2H), 0.98(t, J=7.2 Hz, 3H).

Example 107

Synthesis of 1-oxo-6-propyl-3,4-dihydro-1H-pyrano[3,4-c]pyridine-8-yl acetic ester 500 mg (87%) of 1-oxo-6-propyl-3,4-dihydro-1H-pyrano[3,4-c]pyridine-8-yl acetic ester was obtained in white solid using the method same as in Example 21 except that 564 mg of 8-hydroxy-6-propyl-3,4-dihydro-pyrano[3,4-c]pyridine-1-on HCl salt was used instead of 4-fluoro-aniline-8-hydroxy-6-methyl-3,4-dihydro-pyrano[3,4-c]pyridine-1-on.

$^1$H NMR(300 MHz, CDCl$_3$) δ 7.02(s, 1H), 4.51(t, J=6.0 Hz, 2H), 3.05(t, J=6.0 Hz, 2H), 2.77 (t, J=7.5 Hz, 2H), 2.74(s, 3H), 1.80-1.73(m, 2H), 0.98(t, J=7.5 Hz, 3H).

Example 108

Synthesis of 8-(4-methoxy-benzylamino)-6-propyl-3,4-dihydro-pyrano[3,4-c]pyridine-1-on 450 mg of 8-(4-methoxy-benzylamino)-6-propyl-3,4-dihydro-pyrano[3,4-c]pyridine-1-on was obtained in colorless oil using the method same as in Example 32 except that 335 mg of 8chloro-6-propyl-3,4-dihydro-pyrano[3,4-c]pyridine-1-on was added with 4-methoxy-benzylamine instead of piperidine.

$^1$H NMR(300 MHz, CDCl$_3$) δ 8.50(s, 1H), 7.33-7.28(m, 2H), 688-6.83(m, 2H), 7.01(s, 1H), 4.69(d, J=5.7 Hz, 2H), 4.50(t, J=6.0 Hz, 2H), 3.05(t, J=6.0 Hz, 2H), 2.77 (t, J=7.5 Hz, 2H), 1.80-1.73(m, 2H), 0.98(t, J=7.5 Hz, 3H).

Example 109

Synthesis of 8-amino-6-propyl-3,4-dihydro-pyrano[3,4-c]pyridine-1-on 200 mg (80%) of 8-amino-6-propyl-3,4-dihydro-pyrano[3,4-c]pyridine-1-on was obtained in white solid using the method same as in Example 53 except that 400 mg of 8-(4-methoxy-benzylamino)-6-propyl-3,4-dihydro-pyrano[3,4-c]pyridine-1-on was used instead of 8-(4-methoxy-benzylamino)-6-methyl-3,4-dihydro-pyrano[3,4-c]pyridine-1-on.

$^1$H NMR(300 MHz, CDCl$_3$) δ 7.02(s, 1H), 4.52(t, J=6.0 Hz, 2H), 3.05(t, J=6.0 Hz, 2H), 2.77 (t, J=7.5 Hz, 2H), 1.80-1.73(m, 2H), 0.97 (t, J=7.5 Hz, 3H).

Example 110

Synthesis of N-(1-oxo-propyl-3,4-dihydro-1H-pyrano[3,4-c]pyridine-8-yl)-acetamide 220 mg (92%) of N-(1-oxo-6-propyl-3,4-dihydro-1H-pyrano[3,4-c]pyridine-8-yl)-acetamide was obtained in white solid using the method same as in Example 54 except that 200 mg of 8-amino-6-propyl-3,4-dihydro-pyrano[3,4-c]pyridine-1-on was used instead of 8-amino-6-methyl-3,4-dihydro-pyrano[3,4-c]pyridine-1-on.

$^1$H NMR(300 MHz, CDCl$_3$) δ 10.9(s, 1H), 7.00(s, 1H), 4.50(t, J=6.0 Hz, 2H), 3.04(t, J=2 Hz, 2H), 2.77 (t, J=7.5 Hz, 2H), 2.60(s, 3H), 1.81-1.74(m, 2H), 0.99(t, J=7.5 Hz, 3H).

Example 111

Synthesis of 4-(2-methoxy-ethyl)-quinoline-3-carbonitrile 4-methyl-quinoline-3-carbonitrile (600 mg, 3.567 mmol) was dissolved in 10 mL of anhydrous THF, added with LHMDS (1M solution in THF, 3.9 mL, 3.924 mmol) at −78° C. under the nitrogen atmosphere and then stirred for about 1 hour at the same temperature. The mixture was dropwisely added with chloromethyl methyl ether (0.30 mL, 3.924 mmol) and then stirred for about 1 hour at −50° C., and then for about 1 hour at 0° C. The above mixture, while being stirred at 0° C., was added with 5 mL of a saturated solution of ammonium chloride and 10 mL of distilled water and then extracted twice with 50 mL of EtOAc. The resulting organic layer was washed with a saturated solution of sodium chloride, dried with anhydrous sodium sulfate and filtered. A silica gel column chromatography (30% EtOAc/Hexanes) was performed on the residue resulted by concentration of the above filtrate and obtained 305 mg (40%) of 4-(2-methoxy-ethyl)-quinoline-3-carbonitrile in pale yellow solid.

$^1$H NMR(300 MHz, CDCl$_3$) δ 3.34(s, 3H), 3.62(t, 2H, J=6.6 Hz), 3.78(t, 2H, J=6.6 Hz), 7.67-7.73(m, 1H), 7.84-7.89(m, 1H), 8.15-8.19(m, 2H), 8.98(s, 1H).

Example 112

Synthesis of 3,4-dihydro-2-oxa-9-aza-phenanthrene-1-on 4-(2-methoxy-ethyl)-quinoline-3-carbonitrile (250 mg, 1.178 mmol) was dissolved in 10 mL of conc. HCl and heated to reflux for about 15 hours. The mixture was concentrated under reduced pressure, dissolved in 10 mL of distilled water, neutralized with a saturated solution of sodium hydrogen carbonate and extracted twice with 50 mL of methylene chloride. The resulting organic layer was dried with anhydrous sodium sulfate, filtered and concentrated. A silica gel column chromatography (3% MeOH/MC) was performed on the residue resulted by concentration of the above filtrate and obtained 216 mg (92%) of 3,4-dihydro-2-oxa-9-aza-phenanthrene-1-on in white solid.

$^1$H NMR(300 MHz, CDCl$_3$) δ 3.49(t, 2H, J=6.3 Hz), 4.73 (t, 2H, J=6.3 Hz), 7.68-7.74(m, 1H), 7.86-7.92(m, 1H), 8.03 (d, 1H, J=8.1 Hz), 8.21(d, 1H, J=8.1 Hz), 9.48(s, 1H).

Example 113

Synthesis of 3,4-dihydro-pyrano[3,4-c]pyridine-1-thione 3,4-dihydro-pyrano[3,4-c]pyridine-1-on (250 mg, 1.676 mmol) was dissolved in anhydrous toluene and stirred overnight at room temperature after adding Lawesson reagent (420 mg, 1.005 mmol). The mixture was evaporated under reduced pressure and a silica gel column chromatography (70% EtOAc/Hexane) was performed on the resulting residue and obtained 200 mg (72%) of 3,4-dihydro-pyrano[3,4-c]pyridine-1-thione in yellow solid.

$^1$H NMR(300 MHz, CDCl$_3$) δ 9.50(s, 1H), 8.68(d, J=4.8 Hz, 1H), 7.15(d, J=4.8 Hz, 1H), 4.60(t, J=6.3 Hz, 2H), 3.08(t, J=6.3 Hz, 2H).

Example 114

Synthesis of 4-(2-hydroxy-ethyl)-N-(4-methoxy-benzyl)-nicotinamide 3,4-dihydro-pyrano[3,4-c]pyridine-1-on (1.5 g, 10.06 mmol) was dissolved in 40 mL of anhydrous THF, dropwisely added with 4-methoxybenzylamine (13 mL, 100.56 mmol) and then heated to reflux for about 45 hours under the nitrogen atmosphere. The mixture, while being stirred at 0° C., neutralized by adding 1N HCl and extracted three times with 100 mL of methylene chloride. The resulting organic layer was dried with anhydrous sodium sulfate, filtered and concentrated. A silica gel column chromatography (7% MeOH/MC) was performed on the resulting residue and obtained 2.24 g (78%) of 3,4-dihydro-pyrano[3,4-c]pyridine-1-thione in colorless oil.

$^1$H NMR(300 MHz, DMSO-d$_6$) δ 2.87 (t, 2H, J=6.6 Hz), 3.62(brt, 2H, J=6.6 Hz), 3.74(s, 3H), 4.40(d, 2H, J=5.7 Hz), 4.84(brs, 1H), 6.88-6.92(m, 2H), 7.24-7.29(m, 2H), 7.34(d, 1H, J=5.1 Hz), 8.50(d, 1H, J=5.1 Hz), 8.51(s, 1H), 9.03(brt, 1H, J=5.7 Hz).

Example 115

Synthesis of 2-(4methoxy-benzyl)-3,4-dihydro-2H-[2,7]naphtyridine-1-on 4-(2-hydroxy-ethyl)-N-(4-methoxy-benzyl)-nicotinamide (2.2 g, 7.683 mmol) and triphenylphosphine (4.03 g, 15.37 mmol) were dissolved in 50 mL of anhydrous THF. The mixture, while being stirred at 0° C. under the nitrogen atmosphere, dropwisely added with diethyl azocarboxylate (1.4 mL, 9.220 mmol) and stirred for about 1 hour at room temperature. The mixture was then concentrated under reduced pressure and a silica gel column chromatography (3% MeOH/MC) was performed on the resulting residue and obtained 1.88 g (91%) of 2-(4-methoxy-benzyl)-3,4-dihydro-2H-[2,7]naphtyridine-1-on in white solid.

$^1$H NMR(300 MHz, CDCl$_3$) δ 2.92(t, 2H, J=6.6 Hz), 3.49(t, 2H, J=6.6 Hz), 3.80(s, 3H), 4.72(s, 2H), 6.85-6.90(m, 2H), 7.10(d, 1H, J=5.1 Hz), 7.24-7.29(m, 2H), 8.61(d, 1H, J=5.1 Hz), 9.27 (s, 1H).

Example 116

Synthesis of 3,4-dihydro-2H-[2,7]naphtyridine-1-on 2-(4-methoxy-benzyl)-3,4-dihydro-2H-[2,7]naphtyridine-1-on (1.63 g, 6.075 mmol) was suspended in 30 mL of anhydrous toluene, added with p-toluene sulfonic acid monohydrate (4.62 g, 24.30 mmol) and heated to reflux for about 6 hours under the nitrogen atmosphere. The mixture, while being stirred at 0° C., neutralized by adding a saturated solution of sodium carbonate and extracted seven times with 150 mL of 15% MeOH/MC. The resulting organic layer was dried with anhydrous sodium sulfate, filtered and then concentrated. A silica gel column chromatography (7% MeOH/MC) was performed on the resulting residue an dbtained 550 mg (61%) of 3,4-dihydro-2H-[2,7]naphtyridine-1-on in white solid.

$^1$H NMR(300 MHz, CDCl$_3$) δ 2.93(t, 2H, J=6.6 Hz), 3.38-3.43(m, 2H), 7.35(d, 1H, J=5.1 Hz), 8.08(brs, 1H), 8.59(d, 1H, J=5.1 Hz), 8.90(s, 1H).

Example 117

Synthesis of 2-benzyl-3,4-dihydro-2H-[2,7]naphtyridine-1-on 193 mg (52%) of 2-benzyl-3,4-dihydro-2H-[2,7]naphtyridine-1-on was obtained in colorless oil using the method same as in Example 2 except that 3,4-dihydro-2H-[2,7]naphtyridine-1-on(230 mg, 1.552 mmol) was used instead of 2H-[2,7]naphtyridine-1-on.

$^1$H NMR(300 MHz, CDCl$_3$) δ 2.94(t, 2H, J=6.6 Hz), 3.52(t, 2H, J=6.6 Hz), 4.79(s, 2H), 7.11(d, 1H, J=5.1 Hz), 7.27-7.36 (m, 5H), 8.62(d, 1H, J=5.1 Hz), 9.28(s, 1H).

Example 118

Synthesis of 4-(2-hydroxy-2-phenyl-ethyl)-nicotinonitrile 4-methyl-nicotinonitrile (2.0 g, 16.93 mmol) was dissolved in20 mL of anhydrous THF(20 mL), added with LHMDS (1M solution in THF, 34 mL, 33.86 mmol) at −78° C. under the nitrogen atmosphere and then stirred for about 1 hour at the same temperature. The mixture was dropwisely added with benzaldehyde (2.1 mL, 20.32 mmol) and stirred at −50° C. for about 1 hour. The mixture, while being stirred at 0° C., added with 30 mL of saturated solution of ammonium chloride and 50 ML of distilled water, and then extracted twice with 100 ML of EtOAc. The resulting organic layer was washed with a saturated solution of sodium chloride, dried with anhydrous sodium sulfate, filtered and concentrated. A silica gel column chromatography (2% MeOH/MC) was performed on the resulting residue and obtained 3.46 g (91%) of 4-(2-hydroxy-2-phenyl-ethyl)-nicotinonitrile in pale yellow solid.

$^1$H NMR(300 MHz, CDCl$_3$) δ 2.16(d, 1H, J=3.3 Hz), 3.22-3.24(m, 2H), 5.03-5.08(m, 1H), 7.29(d, 1H, J=5.4 Hz), 7.32-7.38(m, 5H), 8.64(d, 1H, J=5.4 Hz), 8.80(s, 1H).

Example 119

Synthesis of 4styryl-nicotinamide

4(2-hydroxy-2-phenyl-ethyl)-nicotinonitrile (2.0 g, 8.92 mmol) was dissolved in KOH (1M solution in MeOH, 36 mL, 35.67 mmol) and then stirred at room temperature for about 4 hours under the nitrogen atmosphere. The mixture was added with 100 mL of distilled water and extracted twice with 150 mL of methylene chloride. The resulting organic layer was dried with anhydrous sodium sulfate, filetered, and then concentrated. A silica gel column chromatography (10% MeOH/MC) was performed on the resulting residue and obtained 1.66 g (83%) of 4-styryl-nicotinamide in white solid.

$^1$H NMR(300 MHz, DMSO-$d_6$)δ 7.33-7.60(m, 7H), 7.68 (brs, 1H), 7.82(d, 1H, J=5.4 Hz), 8.10(brs, 1H), 8.59(d, 1H, J=5.4 Hz), 8.62(s, 1H).

Example 120

Synthesis of 3-phenyl-3,4-dihydro-pyrano[3,4-c]pyridine-1-on(a) and 3-phenyl-3,4-dihydro-2H-[2,7]naphtyridine-1-on(b)

Styryl-nicotinamide (1.2 g, 5.35 mmol) was dissolved in 10 mL of phosphoric acid and then stirred at 120° C. for about 8 hours. The mixture was added to 200 mL of distilled water, neutralized by adding a saturated solution of sodium carbonate, while stirring it at 0° C., and then extracted twice with 200 mL of methylene chloride. The resulting organic layer was dried with anhydrous sodium sulfate, filtered and then concentrated. A silica gel column chromatography (5% MeOH/MC) was performed on the resulting residues and obtained 408 mg (34%) of 3-phenyl-3,4-dihydro-pyrano[3,4-c]pyridine-1-on(a) and 160 mg (13%) of 3-phenyl-3,4dihydro-2H-[2,7]naphtyridine-1-on(b), respectively, in white solid.

3-phenyl-3,4-dihydro-pyrano[3,4-c ]pyridine-1-on $^1$H NMR(300 MHz, CDCl$_3$) δ 3.13-3.40(m, 2H), 5.57-5.62 (m, 1H), 7.25(d, 1H, J=5.1 Hz), 7.37-7.49(m, 5H), 8.76(d, 1H, J=5.1 Hz), 9.31(s, 1H).

3-phenyl-3,4-dihydro-2H-[2,7]naphtyridine-1-on $^1$H NMR(300 MHz, CDCl$_3$) δ 3.10-3.26(m, 2H), 4.86-4.92 (m, 1H), 6.06(brs, 1H), 7.14(d, 1H, J=5.1 Hz), 7.34-7.45(m, 5H), 8.66(d, 1H, J=5.1 Hz), 9.26(s, 1H).

Example 121

Synthesis of 2-H-[2,7]naphtyridine-1-on 4-methyl-nicotinonitrile (2.0 g, 16.93 mmol) was dissolved in 20 mL of anhydrous DMF, dropwisely added with N,N-dimethylformamide dimethyl acetal (4.5 mL, 33.86 mmol) and then stirred at 120° C. under the nitrogen atmosphere for about 2 hours. The mixture was concentrated under reduced pressure, added with distilled water and then extracted twice with 100 mL EtOAc. The resulting organic layer was washed with a saturated solution of sodium chloride, dried with anhydrous sodium sulfate, and then concentrated. The concentrated residue was dissolved in a mixed solution of 10 mL of acetic acid and 10 mL of sulfuric acid and stirred at 110° C. for about 1 hour. The mixture was then cooled down to room temperature, added to 200 mL of distilled water and neutralized by slowly adding potassium carbonate while stirring it at 0° C. Then, it was extracted 6 times with 150 mL of 20% MeOH/MC. The resulting organic layer was dried with anhydrous sodium sulfate, filtered, and concentrated. A silica gel column chromatography (10% MeOH/MC) was performed on the resulting residue and obtained 1.49 g (60%) of 2H-[2,7]naphtyridine-1-on in pale yellow solid.

$^1$H NMR(300 MHz, DMSO-$d_6$) δ 6.55(d, 1H, J=7.2 Hz), 7.43(d, 1H, J=7.2 Hz), 7.57 (d, 1H, J=5.4 Hz), 8.69(d, 1H, J=5.4 Hz), 9.30(s, 1H), 11.59(brs, 1H).

Example 122

Synthesis of 2-benzyl-2H-[2,7]naphtyridine-1-on

2H-[2,7]naphtyridine-1-on (200 mg, 1.368 mmol) was suspended in 6 mL of anhydrous DMF, and added with NaH (60% dispersion in mineral oil, 82 mg, 2.053 mmol) while stirring it at 0° C. under the nitrogen atmosphere. The mixture was cooled down at room temperature for about 2 hours, dropwisely added with benzyl chloride (0.19 mL, 1.642 mmol) at 0° C. and then stirred at room temperature for about 2 hours. The mixture was added with 5 mL of a saturated solution of ammonium chloride and 5 mL of distilled water, while stirring it at 0° C., and extracted twice with 30 mL of EtOAc. The resulting organic layer was washed with a saturated solution of sodium chloride, dried with anhydrous sodium sulfate, filtered and then concentrated. A silica gel column chromatography (5% MeOH/MC) was performed on thus obtained concentrated residue and obtained 288 mg (89%) of 2-benzyl-2H-[2,7]naphtyridine-1-on in white solid.

$^1$H NMR(300 MHz, CDCl$_3$) δ 5.22(s, 2H), 6.42(d, 1H, J=7.2 Hz), 7.26-7.39(m, 7H), 8.72(d, 1H, J=5.1 Hz), 9.65(s, 1H).

Example 123

Synthesis of 8-methyl-6-methyl-2H-[2,7]naphtyridine-1-on 1.91 g (56%) of 8-methyl-6-phenyl-2H-[2,7]naphtyridine-1-on was obtained in pale yellow solid using the method same as in Example 121 except that 2,4-dimethyl-6-phenyl-nicotinonitrile (3.01 g, 14.45 mmol) was used instead of 4-methyl-nicotinonitrile.

$^1$H NMR(300 MHz, DMSO-$d_6$) δ 3.02(s, 3H), 6.53(d, 1H, J=6.9 Hz), 7.36(d, 1H, J=6.9 Hz), 7.44-7.55(m, 3H), 7.98(s, 1H), 8.16-8.20(m, 2H), 11.35(brs, 1H).

Example 124

Synthesis of 8methyl-6-phenyl-3,4-dihydro-2H-[2,7]naphtyridine-1-on 8-methyl-6-phenyl-2H-[2,7]naphtyridine-1-on (500 mg, 2.116 mmol) was suspended in anhydrou ethanol, added with 5% Pd/C (400 mg) and then stirred at room temperature under the hydrogen atmosphere for about 72 hours. The mixture was filtered and then concentrated under reduced pressure. A silica gel column chromatography (2% MeOH/MC) was performed on the resulting residue and obtained 462 mg (92%) of 8-methyl-6-phenyl-3,4-dihydro-2H-[2,7]naphtyridine-1-on in white solid.

$^1$H NMR(300 MHz, DMSO-$d_6$) δ 2.83(s, 3H), 2.95(t, 2H, J=6.3 Hz), 3.31-3.70(m, 2H), 7.43-7.54(m, 3H), 7.79(s, 1H), 8.01(brs, 1H), 8.11-8.14(m, 2H).

Example 125

Synthesis of
2,8-dimethyl-6-phenyl-2H-[2,7]naphtyridine-1-on 320 mg (86%) of 2,8-dimethyl-6-phenyl-2-H-[2,7]naphtyridine-1-on 320 mg (86%) was obtained in pale yellow solid using the method same as in Example 122 except that 8-methyl-6-phenyl-2 H-[2,7]naphtyridine-1-on (350 mg, 1.481 mmol) and iodo methane (0.11 mL, 1.777 mmol) were used instead of 2H-[2,7]naphtyridine-1-on and benzyl chloride.

$^1$H NMR(300 MHz, CDCl$_3$) δ 3.20(s, 3H), 3.58(s, 3H), 6.42(d, 1H, J=7.2 Hz), 7.24(d, 1H, J=7.2 Hz), 7.41-7.52(m, 3H), 7.57 (s, 1H), 8.08-8.12(m, 2H).

Example 126

Synthesis of 2,8-dimethyl-6-phenyl-3,4-dihydro-2H-[2,7]naphtyridine-1-on 195 mg (87%) of 2,8-dimethyl-6-phenyl-3,4-dihydro-2H-[2,7]naphtyridine-1-on was obtained in white solid using the method same as in Example 124 except that 2,8-dimethyl-6-phenyl-2H-[2,7]naphtyridine-1-on(220 mg, 0.879 mmol) was used instead of 8-methyl-6-phenyl-2H-[2,7]naphtyridine-1-on.

$^1$H NMR(300 MHz, CDCl$_3$) δ 3.00(s, 3H), 3.01(t, 2H, J=6.3 Hz), 3.18(s, 3H), 3.57 (t, 2H, J=6.3 Hz), 7.38(s, 1H), 7.42-7.50(m, 3H), 8.02-8.05(m, 2H).

Example 127

Synthesis of 2-benzyl-8-methyl-6-phenyl-2H-[2,7]naphtyridine-1-on 265 mg (96%) of 2-benzyl-8-methyl-6-phenyl-2H-[2,7]naphtyridine-1-on was obtained in white solid using the method same as in Example 122 except that 8-methyl-6-phenyl-2H-[2,7]naphtyridine-1-on(200 mg, 0.846 mmol) was used instead of 2H-[2,7]naphtyridine-1-on.

$^1$H NMR(300 MHz, CDCl$_3$) δ 3.21(s, 3H), 5.19(s, 2H), 6.41(d, 1H, J=7.5 Hz), 7.24(d, 1H, J=7.5 Hz), 7.27-7.39(m, 5H), 7.40-7.52(m, 3H), 7.56(s, 1H), 8.08-8.12(m, 2H).

Example 128

Synthesis of 2-benzyl-8-methyl-6-phenyl-3,4-dihydro-2H-[2,7]naphtyridine-1-on 295 mg (82%) of 2-benzyl-8-methyl-6-phenyl-3,4-dihydro-2H-[2,7]naphtyridine-1-on was obtained in white solid using the method same as in Example 122 except that 8-methyl-6-phenyl-3,4-dihydro-2H-[2,7]naphtyridine-1-on(260 mg, 1.091 mmol) was used instead of 2H-[2,7]naphtyridine-1-on.

$^1$H NMR(300 MHz, CDCl$_3$) δ 2.92(t, 2H, J=6.3 Hz), 3.03 (s, 3H), 3.49(t, 2H, J=6.3 Hz), 4.80(s, 2H), 7.27-7.37(m, 6H), 7.39-7.50(m, 3H), 8.01-8.05(m, 2H).

Example 129

Synthesis of
6-cyclohexyl-2-methoxy-4-methyl-nicotinonitrile 2.23 g (88%) of 6cyclohexyl-2-methoxy-4-methyl-nicotinonitrile was obtained using the method same as in Example 101 except that 2.0 g of 6-chloro-2-methoxy-4-methyl-nicotinonitrile was added with cyclohexyl magnesium chloride instead of n-propyl magnesium bromide.

$^1$H NMR(300 MHz, CDCl$_3$) δ 6.68(s, 1H), 4.04(s, 3H), 2.55-2,64(m, 1H), 2.48(s, 3H), 1.71-1.94(m, 5H), 1.26-1.57 (m, 5H).

Example 130

Synthesis of (3-cyano-6-cyclohexyl-2-methoxy-pyridine-4-yl)-acetic acid methyl ester 2.43 g (87%) of (3-cyano-6-cyclohexyl-2-methoxy-pyridine-4-yl)-acetic acid methyl ester was obtained in yellow oil using the method same as in Example 1 except that 2.23 g of 6-cyclohexyl-2-methoxy-4-methyl-nicotinonitrile was used instead of 4-methyl-nicotinonitrile.

$^1$H NMR(300 MHz, CDCl$_3$) δ 6.77 (s, 1H), 4.04(s, 3H), 3.78(d, J=3.0 Hz, 2H), 3.75(s, 3H), 2.57-2.67(m, 1H), 1.71-1.93(m., 5H), 1.26-1.57 (m.5H).

Example 131

Synthesis of 6-cyclohexyl-4-(2-hydroxy-ethyl)-2-methoxy-nicotinonitrile 2.11 g (96%) of 6-cyclohexyl4-(2-hydroxy-ethyl)-2-methoxy-nicotinonitrile was obtained in colorless oil using the method same as in Example 2 except that 2.43 g of (3-cyano-6-cyclohexyl-2-methoxy-pyridine-4-yl)-acetic acid methyl ester was used instead of (3-cyano-pyridine-4-yl)-acetic acid methyl ester.

$^1$H NMR(300 MHz, CDCl$_3$) δ 6.75(s, 1H), 4.02(s, 3H), 3.91-3,96(m, 3H), 3.00(t, J=6.5 Hz, 2H), 2.55-2.65(m, 1H), 1.69-1.92(m, 5H), 1.26-1.57(m, 5H).

Example 132

Synthesis of 6-cyclohexyl-8-hydroxy-3,4-dihydro-pyrano[3,4-c]pyridine-1-on 1.80 g (90%) of 6-cyclohexyl-8-hydroxy-3,4-dihydro-pyrano[3,4-c]pyridine-1-on was obtained in pale yellow solid using the method same as in Example 3 except that 2.10 g of 6-cyclohexyl-4-(2-hydroxy-ethyl)-2-methoxy-nicotinonitrile was used instead of 4-(2-hydroxy-ethyl)-nicotinonitrile.

$^1$H NMR(300 MHz, DMSO-d$_6$) δ 1.85(s, 1H), 6.09(s, 1H), 4.29(t, J=5.9 Hz, 2H), 2.83(t, J=5.9 Hz, 2H), 2.42-2.51(m, 1H), 1.65-1.82(m, 5H), 1.16-1.47(m, 5H).

Example 133

Synthesis of 6-cyclohexyl-1-oxo-3,4-dihydro-1H-pyrano[3,4-c]pyridine-8-yl acetic acid methyl ester 307 mg (88%) of 6-cyclohexyl-1-oxo-3,4-dihydro-1H-pyrano[3,4c]pyridine-8-yl acetic acid methyl ester was obtained in white solid using the method same as in Example 21 except that 300 mg of 6-cyclohexyl-8-hydroxy-3,4-dihydro-pyrano[3,4-c]pyridine-1-on was used instead of 8-hydroxy-6-methyl-3,4-dihydro-pyrano[3,4-c]pyridine-1-on.

$^1$H NMR(300 MHz, CDCl$_3$) δ 7.02(s, 1H), 4.51(t, J=6.0 Hz, 2H), 3.05(t, J=5.9 Hz, 2H), 2.66-2.76(m, 1H), 2.4(s, 3H), 1.74-2.04(m, 5H), 1.23-1.55(m, 5H).

Example 134

Synthesis of 8-chloro-6-cyclohexyl-3,4-dihydro-pyrano[3,4-c]pyridine-1-on 814 mg (76%) of 8chloro-6-cyclohexyl-3,4-dihydro-pyrano[3,4-c]pyridine-1-on was obtained in white solid using the method same as in Example 20 except that 1.0 g of 6-cyclohexyl-8-hydroxy-3,4-dihydro-pyrano[3,4-c]pyridine-1-on was used instead of 8-hydroxy-6-methyl-3,4-dihydro-pyrano[3,4-c]pyridine-1-on.

$^1$H NMR(300 MHz, CDCl$_3$) δ 7.01(s, 1H), 4.48(t, J=5.9 Hz, 2H), 3.05(t, J=5.9 Hz, 2H), 2.68-2.78(m, 1H), 1.75-1.94 (m, 5H), 1.24-1.63(m, 5H).

Example 135

Synthesis of 6-cyclohexyl-8-piperidine-1-yl-3,4-dihydro-pyrano[3,4-c]pyridine-1-on 173 mg (98%) of 6-cyclohexyl-8-piperidine-1-yl-3,4-dihydro-pyrano[3,4-c]pyridine-1-on was obtained in white solid using the method same as in Example 32 except that 150 mg of 8-chloro-6-cyclohexyl-3,4-dihydro-pyrano[3,4-c]pyridine-1-on was used instead of 8-chloro-6-methyl-3,4-dihydro-pyrano[3,4-c]pyridine-1-on.

$^1$H NMR(300 MHz, CDCl$_3$) δ 6.31(s, 1H), 4.39(t, J=5.7 Hz, 2H), 3.51(br s, 4H), 2.87 (t, J=5.9 Hz, 2H), 2.46-2.55(m, 1H), 1.81-1.92(m, 4H), 1.59-1.66(m, 7H), 1.18-1.55(m, 5H).

Example 136

Synthesis of 6-cyclohexyl-8-(4-methoxy-benzylamino)-3,4-dihydro-pyrano[3,4-c]pyridine-1-on 498 mg (90%) of 6-cyclohexyl-8-(4-methoxy-benzylamino)-3,4-dihydro-pyrano[3,4-c]pyridine-1-on was obtained in white solid using the method same as in Example 32 except that 400 mg of 8-chloro-6-cyclohexyl-3,4-dihydro-pyrano[3,4-c]pyridine-1-on and 4-methoxy-benzylamine were used instead of 8-chloro-6-methyl-3,4-dihydro-pyrano[3,4-c]pyridine-1-on and piperidine.

$^1$H NMR(300 MHz, CDCl$_3$) δ 8.46(br s, 1H), 7.31(d, J=8.4 Hz, 2H), 6.82-6.87(m, 2H), 6.22(s, 1H), 4.71(d, J=5.7 Hz, 2H), 3.79(s, 3H), 2.87 (t, J=5.9 Hz, 2H), 2.48-2.55(m, 1H), 1.72-1.90(m, 5H), 1.18-1.57(m, 5H).

Example 137

Synthesis of 8-amino-6-cyclohexyl-3,4-dihydro-pyrano[3,4-c]pyridine-1-on 190 mg (92%) of 8-amino-6-cyclohexyl-3,4-dihydro-pyrano[3,4-c]pyridine-1-on was obtained in white solid using the method same as in Example 53 except that 307 mg of 6-cyclohexyl-8-(4-methoxy-benzylamino)-3,4-dihydro-pyrano[3,4-c]pyridine-1 was used instead of 8-(4-methoxy-benzyl-amino)-6-methyl-3,4-dihydro-pyrano[3,4-c]pyridine-1-on.

$^1$H NMR(300 MHz, CDCl$_3$) δ 6.32(s, 1H), 4.62(t, J=6.0 Hz, 2H), 2.90(t, J=5.9 Hz, 2H), 2.44-2.52(m, 5H), 1.72-1.91 (m, 5H), 1.19-1.57(m, 5H).

Example 138

Synthesis of 6-isopropyl-2-methoxy-4-methyl-nicotinonitrile 1.01 g (65%) of 6-isopropyl-2-methoxy-4-methyl-nicotinonitrile was obtained in colorless oil using the method same as in Example 101 except that 1.5 g of 6-chloro-2-methoxy-4-methyl-nicotinonitrile was added with magnesium chloride instead of ii-propylmagnesium bromide.

$^1$H NMR(300 MHz, CDCl$_3$) δ 6.68(s, 1H), 4.02(s, 3H), 2.93(quintet, J=6.8 Hz, 1H), 2.46(s, 3H), 1.26(d, J=6.9 Hz, 6H).

Example 139

Synthesis of (3-cyano-6-isopropyl-2-methoxy-pyridine-4-yl)-acetic acid methyl ester 1.41 g (83%) of (3-cyano-6-isopropyl-2-methoxy-pyridine-4-yl)-acetic acid methyl ester was obtained in yellow solid using the method same as in Example 1 except that 1.29 g of 6-isopropyl-2-methoxy-nicotinonitrile was used instead of 4-methyl-nicotinonitrile.

$^1$H NMR(300 MHz, CDCl$_3$) δ 6.78(s, 1H), 4.05(s, 3H), 3.79(s, 2H), 3.75(s, 3H), 2.97 (quintet, J=6.8 Hz, 1H), 2.17 (s, 3H), 1.28(d, J=6.9 Hz. 6H).

Example 140

Synthesis of 4-(2-hydroxy-ethyl)-6-isopropyl-2-methoxy-nicotinonitrile 1.89 g (97%) of 4-(2-hydroxy-ethyl)-6-isopropyl-2-methoxy-nicotinonitrile was obtained in pale yellow oil using the method same as in Example 2 except that 2.20 g of (3-cyano-6-isopropyl-2-methoxy-pyridine-4-yl)-acetic acid methyl ester was used instead of (3-cyano-pyridine-4-yl)-acetic acid methyl ester.

$^1$H NMR(300 MHz, CDCl$_3$) δ 6.77 (s, 1H), 4.04(s, 3H), 3.96(t, J=5.3 Hz, 2H), 2.91-3.04(m, 3H), 1.27 (d, J=6.6 Hz, 6H).

Example 141

Synthesis of 8-hydroxy-6-isopropyl-3,4-dihydro-pyrano[3,4-c]pyridine-1-on 1.20 g (80%) of 8-hydroxy-6-isopropyl-3,4-dihydro-pyrano[3,4-c]pyridine-1-on was obtained in white solid using the method same as in Example 3 except that 1.60 g of (4-(2-hydroxy-ethyl)-6-isopropyl-2-methoxy-nicotinonitrile was used instead of 4-(2-hydroxy-ethyl)-nicotinonitrile.

$^1$H NMR(300 MHz, DMSO-d$_6$) δ 11.89(br s, 1H), 6.12(s, 1H), 4.29(t, J=6.2 Hz, 2H), 2.74-2.86(m, 3H), 1.19(d, J=6.9 Hz, 6H).

Example 142

Synthesis of 6-isopropyl-1-oxo-3,4-dihydro-1-H-pyrano[3,4-c]pyridine-8-yl acetic acid methyl ester 208 mg (87%) of 6-isopropyl-1-oxo-3,4-dihydro-1H-pyrano[3,4-c]pyridine-8-yl acetic acid methyl ester was obtained in white solid using the method same as in Example 21 except that 200 mg of 8-hydroxy-6-isopropyl-3,4-dihydro-pyrano[3,4-c]pyridine-1-on was used instead of 8-hydroxy-6-methyl-3,4dihydro-pyrano[3,4-c]pyridine-1-on.

$^1$H NMR(300 MHz, CDCl$_3$) δ 7.04(s, 1H), 4.51(t, J=6.0 Hz, 2H), 3.02-3.11(m, 3H), 2.41(s, 3H), 1.31(d, J=6.6 Hz, 6H).

Example 143

Synthesis of 8-chloro-6-isopropyl-3,4-dihydro-pyrano[3,4-c]pyridine-1-on 740 mg (85%) of 8-chloro-6-isopropyl-3,4-dihydro-pyrano[3,4-c]pyridine-1-on was obtained in white solid using the method same as in Example 20 except that 800 mg of 8-hydroxy-6-isopropyl-3,4-dihydro-pyrano[3,4-c]pyridine-1-on was used instead of 8-hydroxy-6-methyl-3,4-dihydro-pyrano[3,4-c]pyridine-1-on.

$^1$H NMR(300 MHz, CDCl$_3$) δ 7.03(s, 1H), 4.49(t, J=6.2 Hz, 2H), 3.03-3.12(m, 3H), 1.32(d, J=6.6 Hz, 6H).

Example 144

Synthesis of 6-isopropyl-8-(4-methoxy-benzylamino)-3,4-dihydro-pyrano[3,4-c]pyridine-1-on 481 mg (95%) of 6-isopropyl-8-(4-methoxy-benzylamino)-3,4-dihydro-pyrano[3,4-c]pyridine-1-on was obtained in white solid using the method same as in Example 32 except that 350 mg of 8-chloro-6-isopropyl-3,4-dihydro-pyrano[3,4-c]pyridine-1-on and 4-methoxy-benzylami were used instead of 8-chloro-6-methyl-3,4-dihydro-pyrano[3,4-c]pyridine-1-on and piperidine.

$^1$H NMR(300 MHz, CDCl$_3$) δ 8.48(br s, 1H), 7.29-7.33(m, 2H), 6.83-6.87(m, 2H), 6.23(s, 1H), 4.71(d, J=6.0 Hz, 2H), 4.44(t, J=6.3 Hz, 2H), 3.79(s, 3H), 2.84-2.86(m, 3H), 1.24(d, J=6.0 Hz, 6H).

Meanwhile, the compounds of the above formula 1 of the present invention can be manufactured in various forms of preparations depending on purposes. The followings are only a few of exemplary methods manufacturing preparations comprising the compounds of the above formula 1 as an active component and therefore it should not be construed as limiting the scope of this invention.

Preparation 1: Production of Tablets (Direct Compression)

5.0 mg of active component was sieved and then mixed with 14.1 mg of lactose, 0.8 mg of Crospovidone USNF and 0.1 mg of magnesium stearate. The mixture was pressed and prepared in tablets.

Preparation 2: Production of Tablets (Wet Granulation)

5.0 mg of active component was sieved and then mixed with 16.0 mg of lactose and 4.0 mg of starch. 0.3 mg of polysolvate 80 was dissolved in water and then added to the above mixture to be micronized. After drying, 2.7 mg of colloidal silicon dioxide was mixed with 2.0 mg of magnesium stearate. The micronized mixture was pressed and prepared in tablets.

Preparation 3: Production of Powders and Capsules 5.0 mg of active component was sieved and then mixed with 14.8 mg of lactose, 10.0 mg of polyvinyl pyrolidone and 0.2 mg of magnesium stearate to obtain a mixed powder. The powder was filled into No. 5 gelatin capsules using a suitable apparatus.

Test Example 1

Experiment on Cytokine Inhibitory Activity

1) Cytokine Inhibitory Activity in Human Whole Blood 20 mL of venous whole blood collected respectively from 5 healthy volunteers of men or women, who had never been medicated with anti-inflammatory drugs within the last two weeks, and was added with heparin. 1 mL each of the above blood was respectively collected, and transferred into test tubes in which it was mixed with test material. The above mixture was precultured at 37° C. for about 1 hour. Then it was added with 1 μg/mL of LPS (lipopolysaccharide), allowed to react at the same temperature for about 4 to about 12 hours and then centrifuged at 4° C. at the rate of 3000 rpm for about 10 minutes. Thus produced plasma was respectively collected and its TNF-α in each plasma was quantitated using human TNF-α ELISA kit based on the amount of recombinant TNF-α in humans. The plate used was coated with anti-human TNF-α monoclone IgG antibodies. Likewise, for the test of IL-1α, IL-1α in each plasma was quantitated using the above plasma and human IL-1α ELISA kit based on the amount of recombinant IL-1α in humans. The plate used was coated with anti-human IL-1α monoclone IgG antibodies. Further, for the test of PGE$_2$, PGE$_2$ in each plasma was quantitated using the above plasma and PGE$_2$ ELISA kit based on the amount of recombinant PGE$_2$ in humans. The plate used was coated with anti-human PGE$_2$ monoclone IgG antibodies. From the above tests, inhibitory rates on the expression of each cytokine were obtained and they were compared to that of Indomethacin. The results are shown in the following table 1.

TABLE 1

| Test compound | TNF-α Inhibition rate (conc.) | IL-1α Inhibition rate (conc.) | PGE$_2$ Inhibition rate (conc.) |
|---|---|---|---|
| Indomethacin | 37% (200 μg/mL) | 25% (200 μg/mL) | 37% (200 μg/mL) |
| Compound of Ex. 3 | 90% (100 ng/mL) | 95% (100 ng/mL) | 24% (300 μg/mL) |
| Compound of Ex. 6 | 84% (100 ng/mL) | 90% (100 ng/mL) | 23% (300 μg/mL) |
| Compound of Ex. 9 | 82% (100 ng/mL) | 93% (100 ng/mL) | 38% (300 μg/mL) |

As shown in the above table 1, the pyridine compounds prepared according to the present invention, showed superiorities in cytokine inhibition activities in human whole blood over to those of Indomethacin, a commercially available anti-inflammatory and analgesic agent, in particular, about two to three times greater in inhibitory activities on its production of TNF-α and IL-1α. Further, the compound of Example 9 showed a similar level of inhibitory activity to that of Indomethancin on the production of PGE$_2$.

2) Cytokine Inhibitory Activity in Animal Model

Sprague Dawley (SD) rats with body weights of about 180 to about 200 g were fasted (free drinking) and then tested. Test compounds were administered orally at 40 mg/kg and then abdominally administered with LPS 1 μg/mL after 1 hour. After 2 hours, the rats were sacrificed and bloods were collected from abdominal vein, stored at room temperature for about 2 hours, and then centrifuged at 12,000 rpm for about 2 minutes. Thus produced plasma was respectively collected and its TNF-α in each plasma was quantitated using mouse TNF-α ELISA kit based on the amount of recombinant TNF-α in rats. The plate used was coated with anti-rat TNF-α monoclone IgG antibodies. Likewise, for the test of IL-1α, IL-1α in each plasma was quantitated using the above plasma and mouse IL-1α ELISA kit based on the amount of recombinant IL-1α in rats. The plate used was coated with anti-rat IL-1α monoclone IgG antibodies. Further, for the test of IL-6, IL-6 in each plasma was quantitated using the above plasma and mouse IL-6 ELISA kit based on the amount of recombinant IL-6 in rats. Further, for the test of INF-γ, INF-γ in each plasma was quantitated using the above plasma and mouse INF-γ ELISA kit based on the amount of recombinant INF-γ in rats. The plate used was coated with anti-rat INF-γ monoclone IgG antibodies. From the above tests, inhibitory rates on the expression of each cytokine were obtained and they were compared to that of Indomethacin. The results are shown in the following tables 2 and 3.

TABLE 2

| Test compound | TNF-α Inhibition Rate (Conc.) |
| --- | --- |
| Indomethacin | 46% (200 mg/kg) |
| Compound of Ex. 3 | 75% (40 mg/kg) |
| Compound of Ex. 6 | 39% (40 mg/kg) |
| Compound of Ex. 9 | 59% (40 mg/kg) |
| Compound of Ex. 21 | 93% (40 mg/kg) |
| Compound of Ex. 30 | 79% (40 mg/kg) |
| Compound of Ex. 32 | 74% (40 mg/kg) |
| Compound of Ex. 33 | 90% (40 mg/kg) |
| Compound of Ex. 53 | 53% (40 mg/kg) |
| Compound of Ex. 77 | 66% (40 mg/kg) |
| Compound of Ex. 78 | 68% (40 mg/kg) |
| Compound of Ex. 79 | 78% (40 mg/kg) |
| Compound of Ex. 115 | 43% (40 mg/kg) |
| Compound of Ex. 117 | 69% (40 mg/kg) |

TABLE 3

| Test compound | IL-α Inhibition rate (conc.) | IL-6 Inhibition rate (conc.) | INF-γ Inhibition rate (conc.) |
| --- | --- | --- | --- |
| Indomethacin | 24% (200 mg/kg) | 60% (200 mg/kg) | 13% (200 mg/kg) |
| Compound of Ex. 3 | 65% (40 mg/kg) | 71% (40 mg/kg) | 48% (40 mg/kg) |
| Compound of Ex. 6 | 52% (40 mg/kg) | 78% (40 mg/kg) | 51% (40 mg/kg) |
| Compound of Ex. 9 | 62% (40 mg/kg) | 43% (40 mg/kg) | 45% (40 mg/kg) |

As shown in the above tables 2 and 3, the pyridine compounds prepared according to the present invention, showed superiorities in cytokine inhibition activities in rat model over to those of Indomethacin, in particular, about at least two times greater in inhibitory activities on its production of TNF-α, IL-α, IL-6 and INF-γ. Further, the compounds of Examples 21, 30, 32, 33, and 79 showed a 1.5 or 2 times greater inhibitory activities compared to that of Indomethancin on the production of TNF-α.

3) Cytokine Inhibitory Activity in Cells

General reagents used were purchased from Sigma-Aldrich chem. Co. and cytokine inhibitory activities were tested as follows. Mediums and reagents used in cell culture were purchased from GIBCO BRL (USA), and mouse TNF-α ELISA kit was purchased from R&D system (USA). The apparatus used ELISA reader (Spectra max-Plus 384, Molecular Device, USA).

Murine macrophage cell line RAW 264.7 was kindly provided by Korean Tissue Culture Center (KTCC). The cell line was cultured in DMEM medium containing 10% FBS, in a cell culturing device at the condition of 37° C., 5% $CO_2$. First, murine RAW 264.7 was cultured in DMEM medium containing 10% FBS for about 24 hours, and cells were planted 200 μL each in 96 well plates at the concentration of $5 \times 10^5$/mL and cultured for about 24 hours. Then, test compounds were treated at various concentrations and then reacted at 37° C. for about 1 hour, wherein 1 μg/mL of lipopolysaccharide (LPS) was added thereto and reacted at 37° C. for about 12 hours. The supernatant was recovered and the amount of murine TNF-α on the medium was quantitated using ELISA kit. Thalidomide was respectively used as a positive and a negative control to compare the activities and the results are shown in the following tables 4a -4c.

TABLE 4a

| Test Compounds | Test Conc. | TNF-α Inhibition Rate (%) | Test Compounds | Test Conc. | TNF-α Inhibition Rate (%) |
| --- | --- | --- | --- | --- | --- |
| Thalidomide | 1 mM | 21 | Ex. 3 | 1 mM | 44 |
|  | 100 μM | 20 |  | 100 μM | 43 |
|  | 10 μM | 12 |  | 10 μM | 35 |
|  | 1 μM | 8 |  | 1 μM | 34 |
| Ex. 6 | 1 mM | 38 | Ex. 9 | 1 mM | 41 |
|  | 100 μM | 36 |  | 100 μM | 39 |
|  | 10 μM | 35 |  | 10 μM | 38 |
|  | 1 μM | 30 |  | 1 μM | 37 |
| Ex. 20 | 1 mM | 41 | Ex. 21 | 1 mM | 77 |
|  | 100 μM | 31 |  | 100 μM | 34 |
|  | 10 μM | 21 |  | 10 μM | 15 |
|  | 1 μM | 15 |  | 1 μM | 9 |
| Ex. 22 | 1 mM | 30 | Ex. 26 | 1 mM | 28 |
|  | 100 μM | 17 |  | 100 μM | 17 |
|  | 10 μM | 10 |  | 10 μM | 6 |
|  | 1 μM | — |  | 1 μM | — |

TABLE 4a-continued

| Test Compounds | Test Conc. | TNF-α Inhibition Rate (%) | Test Compounds | Test Conc. | TNF-α Inhibition Rate (%) |
|---|---|---|---|---|---|
| Ex. 27 | 1 mM | 81 | Ex. 28 | 1 mM | 59 |
| | 100 μM | 68 | | 100 μM | 37 |
| | 10 μM | 43 | | 10 μM | 27 |
| | 1 μM | 30 | | 1 μM | 8 |
| Ex. 29 | 1 mM | 30 | Ex. 30 | 1 mM | 100 |
| | 100 μM | 18 | | 100 μM | 100 |
| | 10 μM | 15 | | 10 μM | 100 |
| | 1 μM | 10 | | 1 μM | 100 |
| Ex. 31 | 1 mM | 100 | Ex. 32 | 1 mM | 100 |
| | 100 μM | 100 | | 100 μM | 89 |
| | 10 μM | 100 | | 10 μM | 78 |
| | 1 μM | 100 | | 1 μM | 69 |
| Ex. 33 | 1 mM | 29 | Ex. 34 | 1 mM | 80 |
| | 100 μM | 18 | | 100 μM | 70 |
| | 10 μM | 9 | | 10 μM | 62 |
| | 1 μM | — | | 1 μM | 58 |
| Ex. 35 | 1 mM | 32 | Ex. 37 | 1 mM | 89 |
| | 100 μM | 26 | | 100 μM | 78 |
| | 10 μM | 17 | | 10 μM | 69 |
| | 1 μM | 9 | | 1 μM | 54 |
| Ex. 39 | 1 mM | 40 | Ex. 46 | 1 mM | 29 |
| | 100 μM | 31 | | 100 μM | 19 |
| | 10 μM | 22 | | 10 μM | 9 |
| | 1 μM | 9 | | 1 μM | 3 |

TABLE 4b

| Test Compounds | Test Conc. | TNF-α Inhibition Rate (%) | Test Compounds | Test Conc. | TNF-α Inhibition Rate (%) |
|---|---|---|---|---|---|
| Ex. 50 | 1 mM | 25 | Ex. 51 | 1 mM | 30 |
| | 100 μM | 19 | | 100 μM | 21 |
| | 10 μM | 9 | | 10 μM | 15 |
| | 1 μM | 5 | | 1 μM | 9 |
| Ex. 53 | 1 mM | 100 | Ex. 60 | 1 mM | 78 |
| | 100 μM | 100 | | 100 μM | 56 |
| | 10 μM | 100 | | 10 μM | 48 |
| | 1 μM | 85 | | 1 μM | 39 |
| Ex. 61 | 1 mM | 100 | Ex. 62 | 1 mM | 100 |
| | 100 μM | 100 | | 100 μM | 89 |
| | 10 μM | 100 | | 10 μM | 78 |
| | 1 μM | 87 | | 1 μM | 60 |
| Ex. 68 | 1 mM | 76 | Ex. 73 | 1 mM | 80 |
| | 100 μM | 65 | | 100 μM | 72 |
| | 10 μM | 58 | | 10 μM | 63 |
| | 1 μM | 50 | | 1 μM | 56 |
| Ex. 77 | 1 mM | 100 | Ex. 78 | 1 mM | 100 |
| | 100 μM | 89 | | 100 μM | 98 |
| | 10 μM | 76 | | 10 μM | 85 |
| | 1 μM | 68 | | 1 μM | 79 |
| Ex. 79 | 1 mM | 100 | Ex. 96 | 1 mM | 63 |
| | 100 μM | 94 | | 100 μM | 56 |
| | 10 μM | 8 | | 10 μM | 46 |
| | 1 μM | 76 | | 1 μM | 38 |
| Ex. 97 | 1 mM | 100 | Ex. 98 | 1 mM | 87 |
| | 100 μM | 93 | | 100 μM | 72 |
| | 10 μM | 84 | | 10 μM | 64 |
| | 1 μM | 75 | | 1 μM | 56 |
| Ex. 99 | 1 mM | 35 | Ex. 100 | 1 mM | 29 |
| | 100 μM | 22 | | 100 μM | 18 |
| | 10 μM | 19 | | 10 μM | 9 |
| | 1 μM | 9 | | 1 μM | — |
| Ex. 112 | 1 mM | 35 | Ex. 113 | 1 mM | 42 |
| | 100 μM | 33 | | 100 μM | 28 |
| | 10 μM | 28 | | 10 μM | 19 |
| | 1 μM | 24 | | 1 μM | 10 |
| Ex. 115 | 1 mM | 78 | Ex. 116 | 1 mM | 29 |
| | 100 μM | 65 | | 100 μM | 18 |
| | 10 μM | 59 | | 10 μM | 10 |
| | 1 μM | 50 | | 1 μM | — |

TABLE 4c

| Test Compounds | Inhibition Test Conc. | TNF-α Rate (%) |
|---|---|---|
| Ex. 117 | 1 mM | 35 |
| | 100 μM | 29 |
| | 10 μM | 18 |
| | 1 μM | 10 |
| Ex. 120a | 1 mM | 85 |
| | 100 μM | 66 |
| | 10 μM | 54 |
| | 1 μM | 43 |
| Ex. 120b | 1 mM | 42 |
| | 100 μM | 32 |
| | 10 μM | 30 |
| | 1 μM | 26 |

As shown in the above tables 4a-4c, the pyridine compounds of the present invention in general showed superior inhibitory activities in RAW 264.7 cell line on the production of TNF-α. In particular, the compounds of Examples 30, 31, 53, 61, 62, 77, 78, 79 and 97 showed superiorities over to the control compounds.

Test Example 2

Anti-inflammatory and Analgesic Effect in Animal Model

1) Croton Oil-induced Ear Edema Test

Male ICR (Institute of Cancer Research) mouse with body weight of about 20 to 30 g were tested wherein each group had 6 mouses. After 1 hour of the oral administration of a test compound, Croton oil (in acetone solution) was coated on one of the ears. After 4 hours, the thickness of the swollen ear in treated group was compared with the other unswollen ear and obtained the average increase rate in thickness of ear by the treatment. The above increase rate was compared with that of placebo treated group and the result is shown in the following table 5.

TABLE 5

| Test Compounds | Treatment (mg/kg) | Inhibition Rate (%) |
|---|---|---|
| Celecoxib | 100 | 35 |
| Ex. 3 | 2 | 33 |
| | 10 | 56 |
| | 50 | 57 |
| Ex. 6 | 2 | 17 |
| | 10 | 39 |
| | 50 | 69 |
| Ex. 9 | 2 | 25 |
| | 10 | 44 |
| | 50 | 37 |

2) Arachidonic Acid-induced Ear Edema Test

Male ICR (Institute of Cancer Research) mouse with body weight of about 20 to 30 g were tested wherein each group had 6 mouses. After 1 hour of the oral administration of a test compound, Arachidonic acid (in acetone solution) was coated on one of the ears. After 1 hour, the thickness of the swollen ear in treated group was compared with the other unswollen ear and obtained the average increase rate in thickness of ear by the treatment. The above increase rate was compared with that of placebo treated group and the result is shown in the following table 6.

TABLE 6

| Test Compounds | Treatment (mg/kg) | Inhibition Rate (%) |
|---|---|---|
| Celecoxib | 100 | 33 |
| Ex. 3 | 2 | 33 |
| | 10 | 51 |
| | 50 | 46 |
| Ex. 6 | 2 | 21 |
| | 10 | 36 |
| | 50 | 41 |
| Ex. 9 | 2 | 21 |
| | 10 | 29 |
| | 50 | 39 |

3) Analgesic Test

Male ICR (Institute of Cancer Research) mouse with body weight of about 20 to 30 g were tested wherein each group had 6 mouses. After 1 hour of the oral administration of a test compound, acetic acid (in distilled water) was abdominally administered. For the duration of 10 minutes, the animals were observed regarding the number of stretchings and the number was compared with that of placebo treated group and the result is shown in the following table 7.

TABLE 7

| Test Compounds | Treatment (mg/kg) | Inhibition Rate (%) |
|---|---|---|
| Celecoxib | 100 | 81 |
| Ex. 3 | 10 | 76 |
| | 50 | 92 |
| Ex. 6 | 10 | 76 |
| | 50 | 75 |
| Ex. 9 | 10 | 73 |
| | 50 | 76 |

As shown in the above tables 5 and 6, in animal models, the anti-inflammatory effects of the pyridine compounds of the present invention were comparable to that of the commercially available Celecoxib (100 mg/kg) at the concentration of 2 mg/kg and 10 mg/kg, respectively. However, the anti-inflammatory effects of the pyridine compounds of the present invention were all greater than that of Celecoxib at the concentration of 50 mg/kg. Further, in the analgesic test in the above table 7, the pyridine compounds of the present invention showed a bit lower but similar level of analgesic effect as compared to that of Celecoxib (100 mg/kg) and the compound of Example 9 showed a similar level of analgesic effect as compared to that of Celecoxib.

INDUSTRIAL APPLICABILITY

As stated above, the pyridine derivatieves of the above formula 1 of the present invention have shown excellent inhibitory effects on the production of cytokines which are involved in inflammatory responses, more specifically they have shown excellent inhibitory effects on the production of TNF-α, IL-1α, IL-6, INF-γ, $PGE_2$. Further, they have also shown superiorities in anti-inflammatory and analgesic effects over the commercially available Indomethacin or Celecoxib. Therefore, the pyridine derivatieves of the above formula 1 of the present invention are useful as therapeutic agents for treating diseases related to inflammation, immune, chronic inflammation as well as an agent having an anti-inflammatory and analgesic effect.

What is claimed is:

1. A compound or pharmaceutically acceptable salt of the following formula 1,

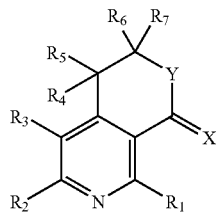

(1)

wherein $R_1$, $R_2$, $R_4$, $R_5$, $R_6$ and $R_7$ are independently selected from the group consisting of a hydrogen atom, a halo, a cyano, a nitro, an acyl, a hydroxy, an amino, a $C_1$-$C_6$ low alkyl, a $C_2$-$C_6$ low alkenyl, a $C_1$-$C_6$ low alkoxy, a $C_1$-$C_6$ alkylthio, a $C_1$-$C_{10}$ alkylamino, a $C_4$-$C_9$ cycloalkylamino, a $C_4$-$C_9$ heterocycloalkylamino, a $C_1$-$C_{10}$ aralkylamino, an arylamino, an acylamino, a saturated heterocyclic, an acyloxy, a $C_1$-$C_6$ alkylsulfinyl, a $C_1$-$C_6$ alkylsulfonyl, a $C_1$-$C_6$ alkylsulfonylamino, an arylsulfinyl, an arylsulfonyl, an arylsulfonylamino, an aryl, a heteroaryl, a $C_1$-$C_{10}$ aralkyl, a $C_1$-$C_{10}$ heteroaralkyl, an aryloxy and a heteroaryloxy group;

$R_3$ is selected from the group consisting of a hydrogen atom, a halo, a cyano, a nitro, an acyl, a hydroxy, an amino, a $C_1$-$C_6$ low alkyl, a $C_1$-$C_6$ low alkoxy, a $C_1$-$C_6$ alkylthio, a $C_1$-$C_{10}$ alkylamino, a $C_4$-$C_9$ cycloalkylamino, a $C_4$-$C_9$ heterocycloalkylamino, a $C_1$-$C_{10}$ aralkylamino, an arylamino, an acylamino, a saturated heterocyclic, an acyloxy, a $C_1$-$C_6$ alkylsulfinyl, a $C_1$-$C_6$ alkylsulfonyl, a $C_1$-$C_6$ alkylsulfonylamino, an arylsulfinyl, an arylsulfonyl, an arylsulfonylamino, an aryl, a heteroaryl, a $C_1$-$C_{10}$ aralkyl, a $C_1$-$C_{10}$ heteroaralkyl, an aryloxy and a heteroaryloxy group;

or $R_1$, $R_2$, $R_3$, $R_4$, $R_5$, $R_6$ and $R_7$ independently form a ring by binding with a neighboring substitution group;

$R_3$ is

X is an oxygen or sulfur atom;

Y is an oxygen atom or N—$R_8$, wherein $R_8$ is selected from the group consisting of a hydrogen atom, a $C_1$-$C_6$ low alkyl, an acyl, an aryl, a heteroaryl, a $C_1$-$C_{10}$ aralkyl and a $C_1$-$C_{10}$ heteroaralkyl group; or forms a ring by binding with a neighboring substitution group of $R_6$ or $R_7$;

said aryl group is selected from a phenyl, a naphthyl and a fused phenyl group;

said heteroaryl and saturated heterocyclic groups are a heterocyclic ring with a pentagonal or hexagonal shape having 1 to 3 heteroatoms selected from an oxygen, a nitrogen, and a sulfur atom; or a fused heterocyclic ring; and said aryl and heteroaryl groups are such that 1 to 4 substitution groups selected from the group consisting of a halo, a hydroxy, a $C_1$-$C_6$ low alkyl, a $C_1$-$C_6$ low alkoxy, an amino, a cyano, a nitro, a carbonyl and a carboxyl group are substituted.

2. The compound or pharmaceutically acceptable salt of claim 1, wherein said X and Y are independently an oxygen atom.

3. The compound or pharmaceutically acceptable salt of claim 1, wherein said $R_1$, $R_2$ and $R_3$ are independently selected from the group consisting of a hydrogen atom, a halo, a hydroxy, a $C_1$-$C_6$ low alkyl, a $C_2$-$C_6$ low alkenyl, a $C_1$-$C_6$ low alkoxy, an aryloxy, an amino, a $C_1$-$C_6$ alkylamino, a $C_1$-$C_{10}$ aralkylamino, an arylamino, an acylamino, a saturated heterocyclic, an aryl, a heteroaryl, and a $C_1$-$C_{10}$ heteroaralkyl group; or neighboring $R_2$ and $R_3$ form a ring by binding with each other;

said $R_4$, $R_5$, $R_6$ and $R_7$ are independently selected from the group consisting of a hydrogen atom, a $C_1$-$C_6$ low alkyl and an aryl group; or $R_4$, $R_5$, $R_6$ and $R_7$ independently form a ring by binding with a neighboring substitution group;

X is an oxygen or sulfur atom;

Y is an oxygen atom or N—$R_8$, wherein $R_8$ is selected from the group consisting of a hydrogen atom, a $C_1$-$C_6$ low alkyl, an aryl, and a $C_1$-$C_{10}$ aralkyl group;

said aryl group is a phenyl group;

said heteroaryl and saturated heterocyclic groups are selected from furan, thiophene, pyridine, piperidine, piperazine, morpholine, pyrolidine and benzodioxol; and said aryl and heteroaryl groups are such that 1 to 4 substitution groups selected from the group consisting of a halo, a hydroxy, a $C_1$-$C_6$ low alkyl, a $C_1$-$C_6$ low alkoxy, an amino, a cyano, a nitro, a carbonyl and a carboxyl group are substituted.

4. The compound or pharmaceutically acceptable salt of claim 1, wherein said compound of formula 1 is selected from the group consisting of 3,4-dihydro-pyrano[3,4-c]pyridine-1-on,
6-methyl-3,4-dihydro-pyrano[3,4-c]pyridine-1-on,
5-vinyl-3,4-dihydro-pyrano[3,4-c]pyridine-1-on,
6,8-dichloro-3,4-dihydro-pyrano[3,4-c]pyridine-1-on,
6,8-dihydroxy-3,4-dihydro-pyrano[3,4-c]pyridine-1-on,
8-hydroxy-6-methyl-3,4-dihydro-pyrano[3,4-c]pyridine-1-on,
8-chloro-6-methyl-3,4-dihydro-pyrano[3,4-c]pyridine-1-on,
6-methyl-1-oxo-3,4-dihydro-1H-pyrano[3,4-c]pyridine-8-yl acetic ester,
8-methoxy-6-methyl-3,4-dihydro-pyrano[3,4-c]pyridine-1-on,
6,8-dimethyl-3,4-dihydro-pyrano[3,4-c]pyridine-1-on,
6-methyl-8-furan-2-yl-3,4-dihydro-pyrano[3,4-c]pyridine-1-on,
6-methyl-8-thiophene-2-yl-3,4-dihydro-pyrano[3,4-c]pyridine-1-on,
6-methyl-8-pyridine-2-yl-3,4-dihydro-pyrano[3,4-c]pyridine-1-on,
8-(4-fluoro-phenyl)-6-methyl-3,4-dihydro-pyrano[3,4-c]pyridine-1-on,
8-(4-chloro-phenyl)-6-methyl-3,4-dihydro-pyrano[3,4-c]pyridine-1-on,
6-methyl-8-piperidine-1-yl-3,4-dihydro-pyrano[3,4-c]pyridine-1-on,
6-methyl-8-morpholine-4-yl-3,4-dihydro-pyrano[3,4-c]pyridine-1-on,
6-methyl-8-(4-methyl-piperazine-1-yl)-3,4-dihydro-pyrano[3,4-c]pyridine-1-on,
6-methyl-8-(4-pyrimidine-2-yl-piperazine-1-yl)-3,4-dihydro-pyrano[3,4-c]pyridine-1-on,
8-(4-fluoro-phenylamino)-6-methyl-3,4-dihydro-pyrano[3,4-c]pyridine-1-on,
8-(4-chloro-phenylamino)-6-methyl-3,4-dihydro-pyrano[3,4-c]pyridine-1-on,
8-(4-trifluoromethyl-phenylamino)-6-methyl-3,4-dihydro-pyrano[3,4-c]pyridine-1-on,
6-methyl-8-p-tolylamino-3,4-dihydro-pyrano[3,4-c]pyridine-1-on,

- 6-methyl-8-phenylamino-3,4-dihydro-pyrano[3,4-c]pyridine-1-on,
- 6-methyl-8-phenetylamino-3,4-dihydro-pyrano[3,4-c]pyridine-1-on,
- 8-[(benzo[1,3]dioxol-5-ylmethyl)-amino]-6-methyl-3,4-dihydro-pyrano[3,4-c]pyridine-1-on,
- 6-methyl-8-phenyl-3,4-dihydro-pyrano[3,4-c]pyridine-1-on,
- 6-methyl-8-phenoxy-3,4-dihydro-pyrano[3,4-c]pyridine-1-on,
- 8-benzylamino-6-methyl-3,4-dihydro-pyrano[3,4-c]pyridine-1-on,
- 8-(4-methoxy-benzylamino)-6-methyll-3,4-dihydro-pyrano[3,4-c]pyridine-1-on,
- 8-amino-6-methyl-3,4-dihydro-pyrano[3,4-c]pyridine-1-on,
- 8-acetamido-6-methyl-3,4-dihydro-pyrano[3,4-c]pyridine-1-on,
- 8-benzamindo-6-methyl-3,4-dihydro-pyrano[3,4-c]pyridine-1-on,
- 8-hydroxy-6-methyl-5-phenyl-3,4-dihydro-pyrano[3,4-c]pyridine-1-on,
- 8-chloro-6-methyl-5-phenyl-3,4-dihydro-pyrano[3,4-c]pyridine-1-on,
- 6-methyl-5-phenyl-3,4-dihydro-pyrano[3,4-c]pyridine-1-on,
- 6-phenyl-3,4-dihydro-pyrano[3,4-c]pyridine-1-on,
- 8-hydroxy-phenyl-3,4-dihydro-pyrano[3,4-c]pyridine-1-on,
- 8-chloro-6-phenyl-3,4-dihydro-pyrano[3,4-c]pyridine-1-on,
- 8-methyl-6-phenyl-3,4-dihydro-pyrano[3,4-c]pyridine-1-on,
- 1-oxo-6-phenyl-3,4-dihydro-1H-pyrano[3,4-c]pyridine-8-yl acetic ester,
- 8-methoxy-6-phenyl-3,4-dihydro-pyrano[3,4c]pyridine-1-on,
- 8-methylamino-6-phenyl-3,4-dihydro-pyrano[3,4-c]pyridine-1-on,
- 8-dimethylamino-6-phenyl-3,4-dihydro-pyrano[3,4-c]pyridine-1-on,
- 6-phenyl-8-piperidine-1-yl-3,4-dihydro-pyrano[3,4-c]pyridine-1-on,
- 8-morpholine-4-yl-6-phenyl-3,4-dihydro-pyrano[3,4-c]pyridine-1-on,
- 6-phenyl-8-pyrolidine-1-yl-3,4-dihydro-pyrano[3,4-c]pyridine-1-on,
- 8-(4-fluoro-phenylamino)-6-phenyl-3,4-dihydro-pyrano[3,4-c]pyridine-1-on,
- 8-(4-methoxy-benzylamino)-6-phenyl-3,4-dihydro-pyrano[3,4-c]pyridine-1-on,
- 8-amino-6-phenyl-3,4-dihydro-pyrano[3,4-c]pyridine-1-on,
- 8-acetamido-6-phenyl-3,4-dihydro-pyrano[3,4-c]pyridine-1-on,
- 8-benzamido-6-phenyl-3,4-dihydro-pyrano[3,4-c]pyridine-1-on,
- 6-hydroxy-8-methyl-3,4-dihydro-pyrano[3,4-c]pyridine-1-on,
- 6-chloro-8-methyl-3,4-dihydro-pyrano[3,4-c]pyridine-1-on,
- 8-methyl-6-(thiophene-2-yl)-3,4-dihydro-pyrano[3,4-c]pyridine-1-on,
- 6-(furan-2-yl)-8-methyl-3,4-dihydro-pyrano[3,4-c]pyridine-1-on,
- 6-(benzo[d][1,3]dioxol-6-yl)-8-methyl-3,4-dihydro-pyrano[3,4-c]pyridine-1-on,
- 6-(4-(dimethylamino)phenyl)-8-methyl-3,4-dihydro-pyrano[3,4-c]pyridine-1-on,
- 8-hydroxy-6-propyl-3,4-dihydro-pyrano[3,4-c]pyridine-1-on,
- 8-chloro-6-propyl-3,4-dihydro-pyrano[3,4-c]pyridine-1-on,
- 8-propyl-6-chloro-3,4-dihydro-pyrano[3,4-c]pyridine-1-on,
- 8-morpholine-4-yl-6-propyl-3,4-dihydro-pyrano[3,4-c]pyridine-1-on,
- 1-oxo-6-propyl-3,4-dihydro-1H-pyrano[3,4-c]pyridine-8-yl acetic ester
- 8-(4-methoxy-benzylamino)-6-propyl-3,4-dihydro-pyrano[3,4-c]pyridine-1-on,
- 8-amino-6-propyl-3,4-dihydro-pyrano[3,4-c]pyridine-1-on,
- N-(1-oxo-6-propyl-3,4-dihydro-1H-pyrano[3,4-c]pyridine-8-yl)-acetamide,
- 3,4-dihydro-2-oxa-aza-phenanthrene-1-on,
- 3,4-dihydro-pyrano[3,4-c]pyridine-1-thione,
- 2-(4-methoxy-benzyl)-3,4-dihydro-2H-[2,7]naphthyridine-1-on,
- 3,4-dihydro-2H-[2,7]naphthyridine-1-on,
- 2-benzyl-3,4-dihydro-2H-[2,7]naphthyridine-1-on,
- 3-phenyl-3,4-dihydro-pyrano[3,4-c]pyridine-1-on,
- 3-phenyl-3,4-dihydro-2H-[2,7]naphthyridine-1-on,
- 8-methyl-6-phenyl-3,4-dihydro-2H-[2,7]naphthyridine-1-on,
- 2,8-dimethyl-6-phenyl-3,4-dihydro-2H-[2,7]naphthyridine-1-on,
- 2-benzyl-8-methyl-6-phenyl-3,4-dihydro-2H-[2,7]naphthyridine-1-on,
- 6-cyclohexyl-8-hydroxy-3,4-dihydro-pyrano[3,4-c]pyridine-1-on,
- 6-cyclohexyl-1-oxo-3,4-dihydro-1H-pyrano[3,4-c]pyridine-8-yl acetic acid methyl ester,
- 8-chloro-6-cyclohexyl-3,4-dihydro-pyrano[3,4-c]pyridine-1-on,
- 6-cyclohexyl-8-piperidine-1-yl-3,4-dihydro-pyrano[3,4c]pyridine-1-on,
- 6-cyclohexyl-8-(4-mthoxy-benzylamino)-3,4-dihydro-pyrano[3,4-c]pyridine-1-on,
- 8-amino-6-cyclohexyl-3,4-dihydro-pyrano[3,4-c]pyridine-1-on,
- 8-hydroxy-6-isopropyl-3,4-dihydro-pyrano[3,4-c]pyridine-1-on,
- 6-isopropyl-1-oxo-3,4dihydro-1H-pyrano[3,4-c]pyridine-8-yl acetic acid methyl ester,
- 8-chloro-6-isopropyl-3,4-dihydro-pyrano[3,4-c]pyridine-1-on,
- 6-isopropyl-8-(4-methoxy-benzylamino)-3,4-dihydro-pyrano[3,4-c]pyridine-1-on; and their pharmaceutically acceptable salts.

5. A method for preparing a compound of the following formula 1 comprising:
(a) reacting a compound of the following formula 2 with an alkylester compound containing the variable $R_6$ in the presence of a base to obtain a compound of the following formula 3;
(b) reacting said compound of the following formula 3 with a reducing agent or a metal reagent containing the variable $R_7$ at 0° C. or room temperature to obtain an alcohol compound of the following formula 4; and
(c) performing a cyclization of said alcohol compound of the following formula 4 to obtain a compound of the following formula 1, (2)

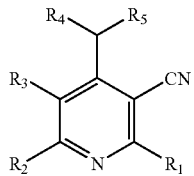

(3)

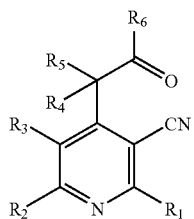

(4)

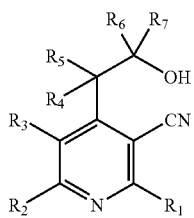

(1)

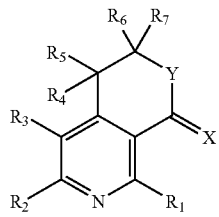

wherein $R_1$, $R_2$, $R_3$, $R_4$, $R_5$, $R_6$, and $R_7$ are the same as defined in claim 1, and X and Y individually represent an oxygen atom.

6. A method for preparing a compound of the following formula 1 comprising:
   (a) reacting a compound of the following formula 2 with an alkylcarbonyl compound represented by $R_6COR_7$ in the presence of a base to obtain a compound of the following formula 4; and
   (b) performing a cyclization of said alcohol compound of the following formula 4 to obtain a compound of the following formula 1, (2)

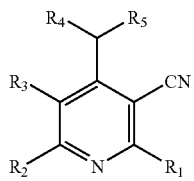

-continued (4)

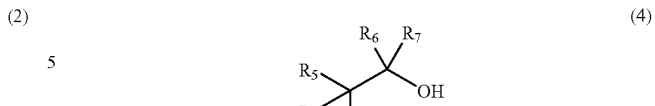

(1)

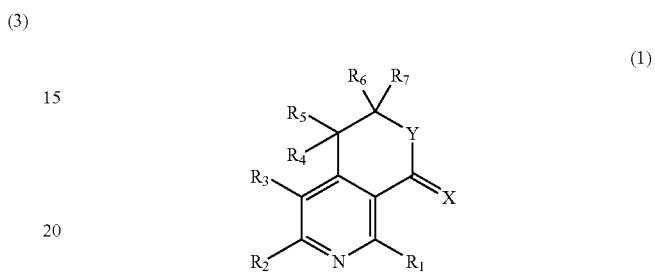

wherein $R_1$, $R_2$, $R_3$, $R_4$, $R_5$, $R_6$, and $R_7$ are the same as defined in claim 1, and X and Y individually represent an oxygen atom.

7. The method of claim 5, wherein said alkylester compound containing the variable $R_6$ is represented by $R_6COOCH_3$.

8. The method of claim 5, wherein said metal reagent containing the variable $R_7$ is a Grignard reagent of $R_7M$, wherein M is an alkali metal, or $R_7MgX^1$, wherein X is a halogen atom).

9. The method of claim 5, wherein said base is selected from the group consisting of lithium bis(trimethylsilyl) amide, potassium bis(trimethylsilyl)amide, lithium diisopropylamide, sodium hydride, potassium hydride and lithium hydride.

10. The method of claim 5, wherein said cyclization is performed by using a strong acid reagent of conc. HCl.

11. A method for preparing a compound of the following formula 1 comprising:
   (a) reacting a compound of the following formula 1, wherein X and Y are individually an oxygen atom, with an amine compound represented by $R_8NH_2$ to obtain a compound of the following formula 8; and
   (b) performing a cyclization of said compound of the following formula 8 to obtain a compound of the following formula 1, wherein X is an oxygen atom and Y is N—$R_8$, (1)

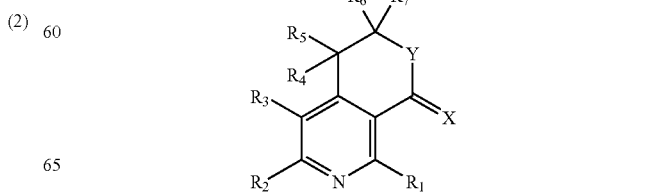

-continued

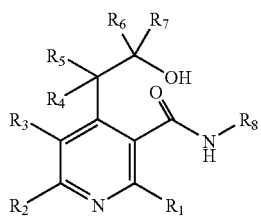
(8)

wherein $R_1$, $R_2$, $R_3$, $R_4$, $R_5$, $R_6$, $R_7$, $R_8$, X and Y are the same as defined in claim 1.

12. The method of claim 11, wherein said cyclization is performed by using diethyl azodicarboxylate and triphenylphosphine.

13. A pharmaceutical composition wherein said composition comprises a compound of the following formula 1 or its pharmaceutically acceptable salt,

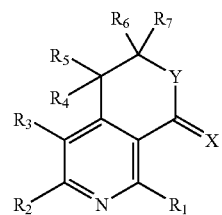
(1)

wherein $R_1$, $R_2$, $R_3$, $R_4$, $R_6$, $R_7$, X and Y are the same as defined in claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,601,736 B2 | Page 1 of 1 |
| APPLICATION NO. | : 10/585029 | |
| DATED | : October 13, 2009 | |
| INVENTOR(S) | : Kim et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 221 days.

Signed and Sealed this

Fifth Day of October, 2010

David J. Kappos
*Director of the United States Patent and Trademark Office*